US010639359B2

(12) United States Patent
Morgan et al.

(10) Patent No.: US 10,639,359 B2
(45) Date of Patent: *May 5, 2020

(54) BCMA CHIMERIC ANTIGEN RECEPTORS

(71) Applicant: bluebird bio, Inc., Cambridge, MA (US)

(72) Inventors: Richard Morgan, Center Harbor, NH (US); Kevin Friedman, Melrose, MA (US)

(73) Assignee: bluebird bio, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/504,853

(22) Filed: Jul. 8, 2019

(65) Prior Publication Data

US 2019/0388527 A1    Dec. 26, 2019

Related U.S. Application Data

(63) Continuation of application No. 15/535,365, filed as application No. PCT/US2015/064269 on Dec. 7, 2015, now Pat. No. 10,383,929.

(60) Provisional application No. 62/200,505, filed on Aug. 3, 2015, provisional application No. 62/091,419, filed on Dec. 12, 2014.

(51) Int. Cl.
| | |
|---|---|
| *A61K 39/00* | (2006.01) |
| *C12N 15/86* | (2006.01) |
| *C12N 5/0783* | (2010.01) |
| *C07K 16/28* | (2006.01) |
| *C07K 14/705* | (2006.01) |
| *C07K 14/725* | (2006.01) |

(52) U.S. Cl.
CPC ...... *A61K 39/0011* (2013.01); *C07K 14/7051* (2013.01); *C07K 14/70517* (2013.01); *C07K 14/70578* (2013.01); *C07K 16/2878* (2013.01); *C12N 5/0636* (2013.01); *C12N 15/86* (2013.01); *A61K 2039/5156* (2013.01); *A61K 2039/5158* (2013.01); *A61K 2039/585* (2013.01); *C07K 2317/622* (2013.01); *C07K 2319/32* (2013.01); *C12N 2740/15043* (2013.01); *C12N 2830/15* (2013.01)

(58) Field of Classification Search
None
See application file for complete search history.

(56) References Cited

U.S. PATENT DOCUMENTS

| | | |
|---|---|---|
| 5,585,089 A | 12/1996 | Queen et al. |
| 5,827,642 A | 10/1998 | Riddell et al. |
| 5,858,358 A | 1/1999 | June et al. |
| 5,883,223 A | 3/1999 | Gray |
| 5,994,136 A | 11/1999 | Naldini et al. |
| 6,005,079 A | 12/1999 | Casterman et al. |
| 6,013,516 A | 1/2000 | Verma et al. |
| 6,040,177 A | 3/2000 | Riddell et al. |
| 6,352,694 B1 | 3/2002 | June et al. |
| 6,534,055 B1 | 3/2003 | June et al. |
| 6,682,907 B1 | 1/2004 | Charneau et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,754,482 B2 | 7/2010 | Riley et al. |
| 7,977,095 B2 | 7/2011 | Bonyhadi et al. |
| 9,034,324 B2 | 5/2015 | Kalled et al. |
| 9,402,865 B2 | 8/2016 | Powell et al. |
| 9,765,342 B2 | 9/2017 | Kochenderfer |
| 10,479,975 B2 | 11/2019 | Friedman |
| 2002/0058019 A1 | 5/2002 | Berenson et al. |
| 2002/0115214 A1 | 8/2002 | June et al. |
| 2002/0177125 A1 | 11/2002 | Kamb et al. |
| 2003/0095955 A1 | 5/2003 | Noessner et al. |
| 2003/0147869 A1 | 8/2003 | Riley et al. |
| 2006/0121005 A1 | 6/2006 | Berenson et al. |
| 2008/0274091 A1 | 11/2008 | Selpushkin et al. |
| 2009/0137017 A1 | 5/2009 | Bonyhadi et al. |
| 2013/0004471 A1 | 1/2013 | Denaro et al. |
| 2013/0280220 A1 | 10/2013 | Ahmed et al. |
| 2013/0288368 A1 | 10/2013 | June et al. |
| 2013/0309193 A1 | 11/2013 | Weinschenk et al. |

(Continued)

FOREIGN PATENT DOCUMENTS

| | | |
|---|---|---|
| AU | 2013204923 A1 | 1/2014 |
| CN | 103442768 A | 12/2013 |

(Continued)

OTHER PUBLICATIONS

"Proleukin for Injection (Chiron)" 2000. 14 pages, downloaded from https://theodora.com/drugs/proleukin_for_injection_chiron.html on Apr. 28, 2018.

Ali, et al., "T cells expressing an anti-B-cell maturation antigen chimeric antigen receptor cause remissions of multiple myeloma." Blood (2016); 128 (13): 1688-1700. Prepublished online Jul. 13, 2016.

Alt and Caselmann. "Liver-directed gene therapy: molecular tools and current preclinical and clinical studies", Journal of Hepatology (1995); 23: 746-758.

Asheuer, M. et al., "Human CD34+ Cells Differentiate into Microglia and Express Recombinant Therapeutic Protein", Proceedings of the National Academy of Sciences USA (2004); 101.10: 3557-3562.

(Continued)

*Primary Examiner* — Christopher M Babic
*Assistant Examiner* — Kimberly A. Aron
(74) *Attorney, Agent, or Firm* — Cooley LLP

(57) ABSTRACT

The invention provides improved compositions for adoptive T cell therapies for B cell related conditions.

21 Claims, 23 Drawing Sheets

Specification includes a Sequence Listing.

(56) References Cited

U.S. PATENT DOCUMENTS

| | | |
|---|---|---|
| 2014/0004132 A1 | 1/2014 | Brenner et al. |
| 2014/0086889 A1 | 3/2014 | Battaglia et al. |
| 2014/0087462 A1 | 3/2014 | Scheffold et al. |
| 2014/0322183 A1 | 10/2014 | Milone et al. |
| 2015/0024482 A1 | 1/2015 | Frigault et al. |
| 2016/0002601 A1 | 1/2016 | Kokundkar et al. |
| 2016/0046724 A1 | 2/2016 | Brogdon et al. |
| 2017/0049819 A1 | 2/2017 | Friedman et al. |
| 2017/0051252 A1 | 2/2017 | Morgan et al. |
| 2017/0051308 A1 | 2/2017 | Morgan et al. |
| 2017/0218337 A1 | 8/2017 | Friedman |
| 2017/0226216 A1 | 8/2017 | Morgan et al. |
| 2019/0194615 A1 | 6/2019 | Friedman |

FOREIGN PATENT DOCUMENTS

| | | |
|---|---|---|
| EP | 0 324 154 A2 | 7/1989 |
| EP | 0404097 A2 | 12/1990 |
| EP | 2094837 A2 | 9/2009 |
| JP | 2013-522286 | 6/2013 |
| WO | WO 1993/001161 A1 | 1/1993 |
| WO | WO 1994/004678 A1 | 3/1994 |
| WO | WO 1994/025591 A1 | 11/1994 |
| WO | WO 1995/028407 | 10/1995 |
| WO | WO 1997/032970 A1 | 9/1997 |
| WO | WO 2003/057171 A2 | 7/2003 |
| WO | WO 2004/035768 A1 | 4/2004 |
| WO | WO 2004/104185 A1 | 12/2004 |
| WO | WO 2006/010834 A1 | 2/2006 |
| WO | WO 2006/090291 A2 | 8/2006 |
| WO | WO 2007/018318 A1 | 2/2007 |
| WO | WO 2008/153742 A2 | 12/2008 |
| WO | WO 2009/091826 A2 | 7/2009 |
| WO | WO 2010/104949 A2 | 9/2010 |
| WO | WO 2011/057124 A1 | 5/2011 |
| WO | WO 2011/114275 A1 | 9/2011 |
| WO | WO 2012/099973 A2 | 7/2012 |
| WO | WO 2012/129514 A1 | 9/2012 |
| WO | WO 2012/140130 A1 | 10/2012 |
| WO | WO 2012/170911 A2 | 12/2012 |
| WO | WO 2013/070468 A1 | 5/2013 |
| WO | WO 2013/126712 A1 | 8/2013 |
| WO | WO 2013/154760 A1 | 10/2013 |
| WO | WO 2014/011996 A1 | 1/2014 |
| WO | WO 2014/031687 A1 | 2/2014 |
| WO | WO 2014/039523 A1 | 3/2014 |
| WO | WO 2014/055442 A1 | 4/2014 |
| WO | WO 2014/055668 A1 | 4/2014 |
| WO | WO 2014/055771 A1 | 4/2014 |
| WO | WO 2014/059173 A2 | 4/2014 |
| WO | WO 2014/089335 A2 | 6/2014 |
| WO | WO 2014/099671 A1 | 6/2014 |
| WO | WO 2014/130635 A1 | 8/2014 |
| WO | WO 2015/123527 A1 | 8/2015 |
| WO | WO 2015/158671 A1 | 10/2015 |
| WO | WO 2015/164739 A1 | 10/2015 |
| WO | WO 2015/164745 A1 | 10/2015 |
| WO | WO 2015/164759 A2 | 10/2015 |
| WO | WO 2015/188119 A1 | 12/2015 |
| WO | WO 2016/014789 A2 | 1/2016 |
| WO | WO 2016/094304 A2 | 6/2016 |
| WO | WO 2016/164429 A1 | 10/2016 |
| WO | WO 2017/099712 A1 | 6/2017 |
| WO | WO 2018/085690 A1 | 5/2018 |

OTHER PUBLICATIONS

Ashwood-Smith, "Preservation of Mouse Bone Marrow at −79° C. with Dimethyl Sulphoxide." Nature (1961); 190: 1204-1205.

Avery, Danielle T., et al. "BAFF selectively enhances the survival of plasmablasts generated from human memory B cells." The Journal of Clinical Investigation (2003); 112.2: 286-297.

Battaglia et al., "Rapamycin selectively expands CD4$^+$CD25$^+$ FoxP3$^+$ regulatory T cells", Blood (2005); 105(12): 4743-4748.

Bellucci, Roberto, et al. "Graft-versus-tumor response in patients with multiple myeloma is associated with antibody response to BCMA, a plasma-cell membrane receptor." Blood (2005); 105.10: 3945-3950.

Bird, Robert E., et al. "Single-chain antigen-binding proteins." Science (1988); 242.4877: 423-427.

Borden and Kabat, "Nucleotide sequence of the cDNAs encoding the variable region heavy and light chains of a myeloma protein specific for the terminal nonreducing end of alpha (1-6) dextran", Proc Natl Acad Sci U S A (1987); 84(8):2440-2443.

Brody and Crystal, "Adenovirus-mediated in vivo gene transfer", Ann. N. Y. Acad. Sci. (1994); 716: 90-101; discussion 101-3.

Carell, Thomas, et al. "A novel procedure for the synthesis of libraries containing small organic molecules." Angewandte Chemie International Edition in English (1994); 33.20: 2059-2061.

Carell, Thomas, et al. "A Solution-Phase Screening Procedure for the Isolation of Active Compounds from a Library of Molecules." Angewandte Chemie International Edition in English (1994); 33.20: 2061-2064.

Carpenito, Carmine, et al. "Control of large, established tumor xenografts with genetically retargeted human T cells containing CD28 and CD137 domains." Proceedings of the National Academy of Sciences USA (2009); 106.9: 3360-3365.

Carpenter, Robert O., et al. "B-cell maturation antigen is a promising target for adoptive T-cell therapy of multiple myeloma." Clinical Cancer Research (2013); 19.8: 2048-2060.

Challita, P. et al., "Multiple modifications in cis elements of the long terminal repeat of retroviral vectors lead to increased expression and decreased DNA methylation in embryonic carcinoma cells." J Virol. (1995); 69(2): 748-755.

Chan, W.K., et al. "Chimeric antigen receptor-redirected CD45RA-negative T cells have potent antileukemia and pathogen memory response without graft-versus-host activity." Leukemia (2015); 29(2): 387-395 (2015).

Chaudhary, Vijay K., et al. "A rapid method of cloning functional variable-region antibody genes in *Escherichia coli* as single-chain immunotoxins." Proceedings of the National Academy of Sciences (1990); 87.3: 1066-1070 (and correction).

Chiu, Apr., et al. "Hodgkin lymphoma cells express TACI and BCMA receptors and generate survival and proliferation signals in response to BAFF and APRIL." Blood (2007); 109.2: 729-739.

Cho, Charles Y., et al. "An unnatural biopolymer." Science (1993); 261: 1303-1304.

Chothia and Lesk, "Canonical structures for the hypervariable regions of immunoglobulins", J Mol Biol (1987); 196(4):901-917.

Chothia, C. et al., "Conformations of immunoglobulin hypervariable regions", Nature (1989); 342(6252):877-883.

Clever, J. et al., "RNA Secondary Structure and Binding Sites for gag Gene Products in the 5' Packaging Signal of Human Immunodeficiency Virus Type 1." J. of Virology (1995); 69(4): 2101-2109.

Cooper, Laurence JN, et al. "T-cell clones can be rendered specific for CD19: Toward the selective augmentation of the graft-versus-B-lineage leukemia effect." Blood (2003); 101.4: 1637-1644.

Cribbs, A.P., et al., "Simplified production and concentration of lentiviral vectors to achieve high transduction in primary human T cells." BMC Biotechnology (2013); 13(1): 98.

Cullen and Greene, "Regulatory Pathways Governing HIV-1 Replication", Cell (1989); 58: 423-426.

Cullen, B.R., "Human Immunodeficiency Virus as a Prototypic Complex Retrovirus", Journal of Virology (1991); 65(3): 1053-1056.

De Felipe, Pablo, and Ryan, Martin D. "Targeting of proteins derived from self-processing polyproteins containing multiple signal sequences." Traffic (2004); 5.8: 616-626.

De Oliveira, S.N., et al. "Modification of Hematopoietic Stem/Progenitor Cells with CD19-Specific Chimeric Antigen Receptors as a Novel Approach for Cancer Immunotherapy." Human Gene Therapy (2013); 24(10): 824-839.

De-Gang, S., et al., "In Vivo Persistence, Tumor Localization, and Antitumor Activity of CAR-Engineered T Cells Is Enhanced by Costimulatory Signaling through CD137 (4-1BB)." Cancer Research (2011), 71(13): 4617-4627.

(56) References Cited

OTHER PUBLICATIONS

Desjarlais, John R., and Berg, Jeremy M. "Length-encoded multiplex binding site determination: application to zinc finger proteins." Proceedings of the National Academy of Sciences (1994); 91.23: 11099-11103.
Desjarlais, John R., and Berg, Jeremy M. "Use of a zinc-finger consensus sequence framework and specificity rules to design specific DNA binding proteins." Proceedings of the National Academy of Sciences (1993); 90.6: 2256-2260.
DeWitt, S. Hobbs, et al. ""Diversomers": An approach to nonpeptide, nonoligomeric chemical diversity." Proceedings of the National Academy of Sciences USA (1993); 90.15: 6909-6913.
Donnelly, M. et al., "The 'cleavage' activities of foot-and-mouth disease virus 2A site-directed mutants and naturally occurring '2A-like' sequences." J Gen Virol. (2001); 82 (Pt 5): 1027-1041.
Dull et al., "A third-generation lentivirus vector with a conditional packaging system", Journal of Virology (1998); 72(11): 8463-8671.
Esser, et al., "NK cells engineered to express a GD2-specific antigen receptor display built-in ADCC-like activity against tumor cells of neuroectodermal origin." Journal of Cellular and Molecular Medicine (2012); 16(3): 569-581.
European Application No. EP 15782739.5, Extended European Search Report dated Nov. 9, 2017, 11 pages.
European Application No. EP 15783117.3, Extended European Search Report dated Aug. 22, 2017, 8 pages.
European Application No. EP 15783862.4, Extended European Search Report dated Sep. 22, 2017, 7 pages.
European Application No. EP 15802488.5, Extended European Search Report dated Dec. 19, 2017, 11 pages.
European Application No. EP 15802488.5, Third Party Observation dated Oct. 17, 2017, 3 pages.
European Application No. EP 15824299.0, Extended European Search Report dated Dec. 13, 2017, 11 pages.
European Application No. EP 15868392.0, Extended European Search Report dated Jun. 25, 2018, 5 pages.
Ferry and Heard, "Liver-directed gene transfer vectors", Hum Gene Ther. (1998); 9(14): 1975-1981.
Friedman et al., "Effective Targeting of Multiple B-Cell Maturation Antigen-Expressing Hematological Malignances by Anti-B-Cell Maturation Antigen Chimeric Antigen Receptor T Cells," Human Gene Therapy, vol. 29, No. 5, 585-601.
Gallop, Mark A., et al. "Applications of combinatorial technologies to drug discovery. 1. Background and peptide combinatorial libraries." Journal of Medicinal Chemistry (1994); 37.9: 1233-1251.
Garfall, A.L., "Immunotherapy with Chimeric Antigen Receptors for Multiple Myeloma." Discovery Medicine: Discovery Class of Medicine, Research Technology, and T. Solariz, Inc., (2014); 17(91): 37-46.
Garland, R. J., et al. "The use of Teflon cell culture bags to expand functionally active CD8+ cytotoxic T lymphocytes." Journal of Immunological Methods (1999); 227.1: 53-63.
Gattinoni, L., et al., "Adoptive immunotherapy for cancer: building on success." Nat Rev Immunol (2006); 6(5): 383-393, 25 pages.
GenBank Accession Reference # L09137.2, "Cloning vector pUC19c", Apr. 27, 1993, 3 pages.
Giannoni, F., et al., "Allelic Exclusion and Peripheral Reconstitution by TCR Transgenic T Cells Arising From Transduced Human Hematopoietic Stem/Progenitor Cells." Molecular Therapy (2013); 21(5): 1044-1054.
Guertin, David A., and Sabatini, David M. "Defining the role of mTOR in cancer." Cancer Cell (2007); 12.1: 9-22.
Haanen, John B.A.G., et al. "Selective expansion of cross-reactive CD8+ memory T cells by viral variants." Journal of Experimental Medicine (1999); 190.9: 1319-1328.
Halene, et al., "Improved Expression in Hematopoietic and Lymphoid Cells in Mice After Transplantation of Bone Marrow Transduced With a Modified Retroviral Vector." Blood (1999); 94(10): 3349-3357.

Hirai, et al., "MK-2206, an Allosteric Aid Inhibitor, Enhances Antitumor Efficacy by Standard Chemotherapeutic Agents or Molecular Targeted Drugs in vitro and in vivo." Molecular Cancer Therapeutics (2010); 9(7): 1956-1967.
Holliger, Philipp, et al. "Diabodies": small bivalent and bispecific antibody fragments. Proceedings of the National Academy of Sciences (1993); 90.14: 6444-6448.
Holt, L. et al., "Domain antibodies: proteins for therapy", Trends in Biotechnology (2003); 21(11): 484-490.
Huang and Yen, "Role of the hepatitis B virus posttranscriptional regulatory element in export of intronless transcripts", Molecular and Cellular Biology (1995); 15(7): 3864-3869.
Hudson, Peter J., and Souriau, Christelle. "Engineered antibodies." Nature medicine 9.1 (2003): 129-134.
Huye L.E. et al. "Combining mTor inhibitors with rapamycin-resistant T cells: a two-pronged approach to tumor elimination". Molecular Therapy, 2011, 19(12): 2239-2248.
Imren, S. et al., "High-level beta-globin expression and preferred intragenic integration after lentiviral transduction of human cord blood stem cells", J Clin Invest (2004); 114(7): 953-962.
International Application No. PCT/US2015/041722, International Preliminary Report on Patentability dated Jan. 24, 2017, 7 pages.
International Preliminary Report on Patentability for International Application No. PCT/US2015/027510, dated Oct. 25, 2016, 6 pages.
International Preliminary Report on Patentability for International Application No. PCT/US2015/027518, dated Oct. 25, 2016, 6 pages.
International Preliminary Report on Patentability for International Application No. PCT/US2015/027539, dated Oct. 25, 2016, 6 pages.
International Preliminary Report on Patentability for International Application No. PCT/US2015/034515, dated Dec. 5, 2016, 10 pages.
International Preliminary Report on Patentability for International Application No. PCT/US2015/064269, dated Jun. 22, 2017, 6 pages.
International Search Report and Written Opinion for International Application No. PCT/US2015/027510, dated Jul. 30, 2015, 10 pages.
International Search Report and Written Opinion for International Application No. PCT/US2015/027518, dated Jul. 30, 2015, 9 pages.
International Search Report and Written Opinion for International Application No. PCT/US2015/027539, dated Nov. 2, 2015, 6 pages.
International Search Report and Written Opinion for International Application No. PCT/US2015/034515, dated Sep. 14, 2015, 12 pages.
International Search Report and Written Opinion for International Application No. PCT/US2015/041722, dated Jan. 6, 2016, 11 pages.
International Search Report and Written Opinion for International Application No. PCT/US2015/064269, dated Feb. 23, 2016, 9 pages.
International Preliminary Report on Patentability for International Application No. PCT/US2015/064270, dated Jun. 12, 2018, 12 pages.
International Search Report and Written Opinion for International Application No. PCT/US2015/064270, dated Feb. 11, 2016, 11 pages.
International Search Report and Written Opinion for International Application No. PCT/US2017/059989, dated Feb. 5, 2018, 9 pages.
Irion, Stefan, et al. "Identification and targeting of the ROSA26 locus in human embryonic stem cells." Nature Biotechnology (2007); 25.12: 1477-1482.
Kalled, Susan L. "The role of BAFF in immune function and implications for autoimmunity." Immunological Reviews (2005); 204.1: 43-54.
Kay, M. A., "Adenoviral Vectors for Hepatic Gene Transfer in Animals." Chest (1997); 111: 138S-142S.
Kim, et al., "Role of P13K/Akt signaling in memory CD8 T cell differentiation." Frontiers in Immunology (2013); 4: 20, 11 pages.
Kim, Yang-Gyun, et al. "Hybrid restriction enzymes: zinc finger fusions to Fok I cleavage domain." Proceedings of the National Academy of Sciences (1996); 93.3: 1156-1160.

(56) References Cited

OTHER PUBLICATIONS

Kochenderfer, J.N., et al. "Adoptive Transfer of Syngeneic T Cells Transduced With a Chimeric Antigen Receptor That Recognizes Murine CD19 Can Eradicate Lymphoma and Normal B Cells." Blood (2010); 16(19): 3875-3886; Gen Bank Accession No. HM754222. 1, 25 pages.
Koch-Nolte, F., "Single domain antibodies from llama effectively and specifically block T cell ecto-ADP-ribosyltransferase ART2.2 in vivo", FASEB J (2007); 21(13):3490-3498.
Koldej, R.M., et al., "Comparison of Insulators and Promoters for Expression of the Wiskott-Aldrich Syndrome Protein Using Lentiviral Vectors" Human Gene Therapy Clinical Development (2013); 24: 77-85.
Kozak, M., "An analysis of 5'-noncoding sequences from 699 vertebrate messenger RNAs", Nucleic Acids Res. (1987); 15(20): 8125-8148.
Kozak, M., "Point mutations define a sequence flanking the AUG initiator codon that modulates translation by eukaryotic ribosomes", Cell (1986); 44(2): 283-292.
Kulemzin et al., "Engineering Chimeric Antigen Receptors," Acta Naturae, vol. 9, No. 1 (32) 2017, 6-14.
Kutner et al., "Production, concentration and titration of pseudotyped HIV-1-based lentiviral vectors", Nature Protocols (2009); 4: 495-505.
Laabi, Y., et al. "A new gene, BCM, on chromosome 16 is fused to the interleukin 2 gene by at (4; 16) (q26; p13) translocation in a malignant T cell lymphoma." The EMBO Journal (1992); 11.11: 3897-3904.
Laabi, Yacine, et al. "The BCMA gene, preferentially expressed during B lymphoid maturation, is bidirectionally transcribed." Nucleic Acids Research (1994); 22.7: 1147-1154.
Landau and Littman. "Packaging system for rapid production of murine leukemia virus vectors with variable tropism." Journal of Virology (1992); 66.8: 5110-5113.
Lanitis, et al., "Chimeric Antigen Receptor T Cells with Dissociated Signaling Domains Exhibit Focused Antitumor Activity with Reduced Potential for Toxicity in Vivo." Cancer Immunology Research (2013); 1(1): 43-53, published on line Apr. 7, 2013.
Larson, S.M., et al. "Anti-CD19 chimeric antigen receptor controlled by the suicide gene HSVsr39TK in hematopoietic stem cells for immunotherapy of B-lineage malignancies." Blood (2013); 122(21): 1659.
Lee, H. C. et al. "Remission in models of type 1 diabetes by gene therapy using a single-chain insulin analogue", Nature (2000); 408(6811): 483-488.
Levitt, "Definition of an efficient synthetic poly(A) site", Genes & Development (1989); 3: 1019-1025.
Li, et al., "Optimal promoter usage for lentiviral vector-mediated transduction of cultured central nervous system cells." Journal of Neuroscience Methods (2010); 189 (1): 56-64.
Li Qun, "Recent progress in the discovery of Akt inhibitors as anticancer agents." Expert Opinion on Therapeutic Patents (2007); 17(9): 1077-1130.
Liu and Mertz, "HnRNP L binds a cis-acting RNA sequence element that enables intron-dependent gene expression." Genes & Dev. (1995); 9: 1766-1780.
Liu, Lin, et al., "Adoptive T-cell therapy of B-cell malignancies: Conventional and physiological chimeric antigen receptors." Cancer Letters (2012); 316(1): 1-5.
Liu, Pixu, et al. "Targeting the phosphoinositide 3-kinase pathway in cancer." Nature Reviews Drug Discovery (2009); 8.8: 627-644.
Liu, Qiang, et al. "Design of polydactyl zinc-finger proteins for unique addressing within complex genomes." Proceedings of the National Academy of Sciences (1997); 94.11: 5525-5530.
Lovelock and Bishop, "Prevention of freezing damage to living cells by dimethyl sulphoxide", Nature (1959); 183(4672): 1394-1395.
MacKay, Fabienne, et al. "BAFF and APRIL: a tutorial on B cell survival." Annual Review of Immunology (2003); 21.1: 231-264.

Maier, Dawn, et al., "Development of a Simple and Robust Closed System Manufacturing Platform for T Cells Engineered With Chimeric Antigen Receptor (CAR) for Adoptive Immunotherapy." Molecular Therapy (2014); Supplement 1(22): S284.
Maldarelli et al., "Identification of posttranscriptionally active inhibitory sequences in human immunodeficiency virus type 1 RNA: novel level of gene regulation", Journal of Virology (1991); 65(11): 5732-5743.
Malim et al., "Immunodeficiency virus rev trans-activator modulates the expression of the viral regulatory genes", Nature (1988); 335: 181-183.
Meuer, Stefan C., et al. "An alternative pathway of T-cell activation: a functional role for the 50 kd T11 sheep erythrocyte receptor protein." Cell (1984); 36.4: 897-906.
Miller, A.D., "Human gene therapy comes of age." Nature (1992); 357: 455-460.
Milone, M. et al., "Chimeric receptors containing CD137 signal transduction domains mediate enhanced survival of T cells and increased antileukemic efficacy in vivo", Molecular Therapy (2009); 17(8):1453-1464.
Moreaux, Jérôme, et al. "BAFF and APRIL protect myeloma cells from apoptosis induced by interleukin 6 deprivation and dexamethasone." Blood (2004); 103.8: 3148-3157.
Movassagh, et al., "Retrovirus-Mediated Gene Transfer into T cells: 95% transduction efficiency without Further in Vitro Selection." Human Gene Therapy (2000); 11: 1189-1200.
Muyldermans, et al., "Nanobodies: Natural Single-Domain Antibodies," Annual Review of Biochemistry vol. 82:775-797 (Volume publication date Jun. 2013) First published online as a Review in Advance on Mar. 13, 2013 https://doi.org/10.1146/annurev-biochem-063011-092449.
Naldini L. et al., "Efficient transfer, integration, and sustained long-term expression of the transgene in adult rat brains injected with a lentiviral vector", Proc Natl Acad Sci USA (1996); 93(21): 11382-11388.
Naldini, L. et al., "In vivo gene delivery and stable transduction of nondividing cells by a lentiviral vector", Science (1996); 272(5259): 263-267.
Naldini, L., "Lentiviruses as gene transfer agents for delivery to non-dividing cells", Curr Opin Biotechnol. (1998); 5: 457-463.
Neri, Paola, et al. "Neutralizing B-Cell-Activating Factor Antibody Improves Survival and Inhibits Osteoclastogenesis in a Severe Combined Immunodeficient Human Multiple Myeloma Model." Clinical Cancer Research (2007); 13.19: 5903-5909.
Ng et al., "B Cell-Activating Factor Belonging to the TNF Family (BAFF)-R Is the Principal BAFF Receptor Facilitating BAFF Costimulation of Circulating T and B Cells." Journal of Immunology (2004); 173(2): 807-817.
Novak, Anne J., et al. "Expression of BCMA, TACI, and BAFF-R in multiple myeloma: a mechanism for growth and survival." Blood (2004); 103.2: 689-694.
Kochenderfer, J.N., et al., "Construction and Pre-clinical Evaluation of an Anti-CD19 Chimeric Antigen Receptor." J Immunother. (2009); 32 (7): 689-702.
O'Connor, Brian P., et al. "BCMA is essential for the survival of long-lived bone marrow plasma cells." Journal of Experimental Medicine (2004); 199.1: 91-98.
Oka, K. et al., "Recent advances in liver-directed gene therapy: implications for the treatment of dyslipidemia", Curr Opin Lipidol. (2000); 11(2): 179-186.
Orlandi, R. et al., "Cloning immunoglobulin variable domains for expression by the polymerase chain reaction", Proc Natl Acad Sci USA (1989); 86(10):3833-3737.
Patel, S. et al., "Impact of chimeric immune receptor extracellular protein domains on T cell function." Gene Ther (1999); 6(3): 412-419.
Perkins, et al., "Manufacturing an Enhanced CAR T Cell Product by Inhibition of the PI3K/Akt Pathway During T Cell Expansion Results in Improved in Vivo Efficacy of Anti-BCMA CAR T Cells." Blood (2015); 126(3): 1893.
Plückthun, A. "Antibodies from *Escherichia coli*." The Pharmacology of Monoclonal Antibodies. (eds. Rosenburg and Moore), Springer Berlin Heidelberg (1994); 113: 269-315.

(56) References Cited

OTHER PUBLICATIONS

Pomerantz, Joel L.,et al. "Structure-based design of transcription factors." Science (1995); 267.5194: 93-96.

Riechmann and Muyldermans, "Single domain antibodies: comparison of camel VH and camelised human VH domains", J Immunol Methods (1999); 231(1-2):25-38.

Rinfret, "Factors Affecting the Erythrocyte During Rapid Freezing and Thawing." Annals of the New York Academy of Sciences (1960); 85 (2): 576-594.

Ruella, M. and Kalos, M. "Adoptive immunotherapy for cancer." Immunological Reviews (2014); 257(1): 14-38.

Ryan, M. et al., "Virus-encoded proteinases of the picornavirus super-group." J Gen Virol. (1997); 78 (Pt 4): 699-723.

Sanchez, Eric, et al. "Serum B-cell maturation antigen is elevated in multiple myeloma and correlates with disease status and survival." British Journal of Haematology (2012); 158.6: 727-738.

Sather, B.B., et al. "Development of B-lineage Predominant Lentiviral Vectors for Use in Genetic Therapies for B Cell Disorders." Molecular Therapy (2011); 19(3): 515-525.

Schiemann, Barbara, et al. "An essential role for BAFF in the normal development of B cells through a BCMA-independent pathway." Science (2001); 293.5537: 2111-2114.

Shirasu and Kuroki, "Functional Design of Chimeric T-Cell Antigen Receptors for Adoptive Immunotherapy of Cancer: Architecture and Outcomes." Anticancer Research (2012); 32 (6): 2377-2383.

Shiratori, Y. et al., "Strategy of liver-directed gene therapy: present status and future prospects", Liver (1999); 19(4): 265-274.

Singh et al., "HER2-positive advanced breast cancer: optimizing patient outcomes and opportunities for drug development", British Journal of Cancer (2014); 111: 1888-1898.

Sloviter and Ravdin, "Recovery and Transfusion of Human Erythrocytes after freezing in Polyglycol Solutions." Nature (1962); 196: 899-900.

Smith-Arica and Bartlett, "Gene Therapy: Recombinant Adeno-associated Virus Vectors", Curr. Cardiol. Rep. (2001); 3: 43-49.

Somerville and Dudley, "Bioreactors get personal." OncoImmunology (2012); 1 (8): 1435-1437.

Soneoka, Yuko, et al. "A transient three-plasmid expression system for the production of high titer retroviral vectors." Nucleic Acids Research (1995); 23.4: 628-633.

Strayer, D.S., "Viral gene delivery", Expert Opinion on Investigational Drugs (1999); 8(12): 2159-2172.

Szymczak, Andrea L., et al. "Correction of multi-gene deficiency in vivo using a single 'self-cleaving' 2A peptide-based retroviral vector." Nature Biotechnology (2004); 22.5: 589-594.

Ten Berge, I. J. M., et al. "Selective expansion of a peripheral blood CD8+ memory T cell subset expressing both granzyme B and I-selectin during primary viral infection in renal allograft recipients." Transplantation Proceedings (1998); 30(8): 3975-3977.

Third Party Submission filed in U.S. Appl. No. 15/316,792, filed Feb. 23, 2018, 6 pages.

Thompson, Jeffrey S., et al. "BAFF binds to the tumor necrosis factor receptor-like molecule B cell maturation antigen and is important for maintaining the peripheral B cell population." Journal of Experimental Medicine (2000); 192.1: 129-136.

Thulé and Liu, "Regulated hepatic insulin gene therapy of STZ-diabetic rats", Gene Therapy (2000); 7: 1744-1752.

Tumaini, B., et al., "Simplified process for the production of anti-CD19-Car-engineered T cells." Cytotherapy (2013); 15: 1406-1415.

Uchibori, et al., "CD269 (BCMA)-Specific CAR-Expressing T Cells Dramatically Eradicate Myeloma Cells from Bone Marrow of an Orthotopic Multiple Myeloma Mouse Model." Molecular Therapy (2016); Abstract 400, 24 (Supplement 1): p. S158-S159.

Urak, et al., "Ex vivo Akt inhibition promotes the generation of potent CD19CAR T cells for adoptive immunotherapy." Journal for ImmunoTherapy of Cancer (2017); 5(1): 26, 13 pages.

Van Der Waart, A.B., et al., "Akt Signalling Inhibition Promotes the Ex Vivo generation of Minor Histocompatibility Antigen-Specific CD8+ Memory Stem T Cells." Blood (2013); 122(21): 3269.

Van Der Waart, A.B., et al., "Inhibition of Akt signaling promotes the generation of superior tumor-reactive T cells for adoptive immunotherapy." Blood (2014); 124(23): 3490-3500.

Van Der Waart, A.B., et al., "Time to Akt Superior tumor-reactive T cells for adoptive immunotherapy." OncoImmunology (2015); 4(5): e1003016, 3 pages.

Vera, Juan, et al. "T lymphocytes redirected against the κ light chain of human immunoglobulin efficiently kill mature B lymphocyte-derived malignant cells." Blood (2006); 108.12: 3890-3897.

Wang, et al., "CS-1 Re-Directed Central Memory T Cell Therapy for Multiple Myeloma." Blood (2014); 124 (21): 1114.

Ward, et al., "Binding activities of a repertoire of single immunoglobulin variable domains secreted from *Escherichia coli*." Nature (1989); 341 (6242): 544-546.

Weigelt, et al., "Genomic determinants of the PI3K pathway inhibitor response in cancer." Frontiers in Oncology (2012), 2: Article V 109, pp. 1-16.

Wu and Kabat, "An analysis of the sequences of the variable regions of Bence Jones proteins and myeloma light chains and their implications for antibody complementarity", J Exp Med. (1970); 132(2): 211-250.

Wu, et al., "Over-expressing Akt in T cells to resist tumor immunosuppression and increase anti-tumor activity." BMC Cancer (2015); 15(1): 603, 10 pages.

Xu, Shengli, and Lam, Kong-Peng. "B-cell maturation protein, which binds the tumor necrosis factor family members BAFF and APRIL, is dispensable for humoral immune responses." Molecular and Cellular Biology (2001); 21.12: 4067-4074.

Xu et al., "The development of CAR design for tumor CAR-T cell therapy," Oncotarget, 2018, vol. 9, No. 17, pp. 1 3991-1 4004.

Xue L. et al., "The role of the PI3K-AKT kinase pathway in T-cell development beyond the beta checkpoint". Eur J Immunol., 2008, 38(11):3200-7.

Yang, N.S., "Gene Transfer into Mammalian Somatic Cells in Vivo", Critical Reviews in Biotechnology (1992); 12(4): 335-356.

Yang, Soo Young, et al. "A common pathway for T lymphocyte activation involving both the CD3-Ti complex and CD2 sheep erythrocyte receptor determinants." The Journal of Immunology (1986); 137.4: 1097-1100.

Yap, et al., "Preclinical Pharmacology, Antitumor Activity, and Development of Pharmacodynamic Markers for the Novel, Potent AKT Inhibitor CCT128930." Molecular Cancer Therapeutics (2011); 10(2): 360-371, (Published on-line First Dec. 29, 2010).

Yee, Jiing-Kuan, et al. "A general method for the generation of high-titer, pantropic retroviral vectors: highly efficient infection of primary hepatocytes." Proceedings of the National Academy of Sciences USA. (1994); 91.20: 9564-9568.

Zennou, V. et al., "HIV-1 genome nuclear import is mediated by a central DNA flap." Cell (2000); 101(2): 173-185.

Zhang, et al., "An NKp30-Based Chimeric Antigen Receptor Promotes T cell Effector Functions and Antitumor Efficacy in Vivo." The Journal of Immunology (2012); 189: 2290-2299 (prepublished online Jul. 30, 2012).

Zhong, Shi, et al. "Retroviral transduction of T-cell receptors in mouse T-cells." JoVE (Journal of Visualized Experiments) (2010); 44: e2307, 4 pages.

Zuckermann, Ronald N., et al. "Discovery of nanomolar ligands for 7-transmembrane G-protein-coupled receptors from a diverse N-(substituted) glycine peptoid library." Journal of Medicinal Chemistry (1994); 37.17: 2678-2685.

Zufferey et al., "Multiply attenuated lentiviral vector achieves efficient gene delivery in vivo", Nat Biotechnol. (1997), 15(9): 871-875.

Zufferey, R. et al., "Woodchuck hepatitis virus posttranscriptional regulatory element enhances expression of transgenes delivered by retroviral vectors." J Virol. (1999); 73(4): 2886-2892.

Zufferey, R. et. al., "Self-Inactivating Lentivirus Vector for Safe and Efficient in Vivo Gene Delivery", J Virol (1998); 72(12): 9873-9880.

European Application No. EP 19193858.8, Extended European Search Report dated Feb. 21, 2020, 10 pages.

BCMA CHIMERIC ANTIGEN RECEPTORS

CROSS REFERENCE TO RELATED APPLICATIONS

This application is a continuation of U.S. application Ser. No. 15/535,365, filed Jun. 12, 2017, which is the National Stage of International Patent Application No. PCT/US2015/064269, filed Dec. 7, 2015, which claims the benefit under 35 U.S.C. § 119(e) of U.S. Provisional Application No. 62/200,505, filed Aug. 3, 2015, and U.S. Provisional Application No. 62/091,419, filed Dec. 12, 2014, where these applications are herein incorporated by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_043_05US_ST25.txt. The text file is 27 KB, was created on Jul. 3, 2019, and is being submitted electronically via EFS-Web, concurrent with the filing of the specification.

BACKGROUND

Technical Field

The present invention relates to improved compositions and methods for treating B cell related conditions. More particularly, the invention relates to improved chimeric antigen receptors (CARs) comprising murine anti-BCMA antibodies or antigen binding fragments thereof, immune effector cells genetically modified to express these CARs, and use of these compositions to effectively treat B cell related conditions.

Description of the Related Art

Several significant diseases involve B lymphocytes, i.e., B cells. Abnormal B cell physiology can also lead to development of autoimmune diseases including, but not limited to systemic lupus erythematosus (SLE). Malignant transformation of B cells leads to cancers including, but not limited to lymphomas, e.g., multiple myeloma and non-Hodgkins' lymphoma.

The large majority of patients having B cell malignancies, including non-Hodgkin's lymphoma (NHL) and multiple myeloma (MM), are significant contributors to cancer mortality. The response of B cell malignancies to various forms of treatment is mixed. Traditional methods of treating B cell malignancies, including chemotherapy and radiotherapy, have limited utility due to toxic side effects. Immunotherapy with anti-CD19, anti-CD20, anti-CD22, anti-CD23, anti-CD52, anti-CD80, and anti-HLA-DR therapeutic antibodies have provided limited success, due in part to poor pharmacokinetic profiles, rapid elimination of antibodies by serum proteases and filtration at the glomerulus, and limited penetration into the tumor site and expression levels of the target antigen on cancer cells. Attempts to use genetically modified cells expressing chimeric antigen receptors (CARs) have also met with limited success. In addition, the therapeutic efficacy of a given antigen binding domain used in a CAR is unpredictable: if the antigen binding domain binds too strongly, the CAR T cells induce massive cytokine release resulting in a potentially fatal immune reaction deemed a "cytokine storm," and if the antigen binding domain binds too weakly, the CAR T cells do not display sufficient therapeutic efficacy in clearing cancer cells.

BRIEF SUMMARY

The invention generally provides improved vectors for generating T cell therapies and methods of using the same.

In various embodiments, a chimeric antigen receptor (CAR) is provided comprising: an extracellular domain that comprises a murine anti-BCMA (B cell maturation antigen) antibody or antigen binding fragment thereof that binds one or more epitopes of a human BCMA polypeptide; a transmembrane domain, one or more intracellular co-stimulatory signaling domains, and a primary signaling domain.

In particular embodiments, the murine anti-BCMA antibody or antigen binding fragment that binds the human BCMA polypeptide is selected from the group consisting of: a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody).

In additional embodiments, the murine anti-BCMA antibody or antigen binding fragment that binds the human BCMA polypeptide is an scFv.

In some embodiments, the murine anti-BCMA antibody or antigen binding fragment thereof comprises one or more CDRs as set forth in any one of SEQ ID NOs: 1-3.

In particular embodiments, the murine anti-BCMA antibody or antigen binding fragment thereof comprises one or more CDRs as set forth in any one of SEQ ID NOs: 4-6.

In certain embodiments, the murine anti-BCMA antibody or antigen binding fragment thereof comprises a variable light chain sequence as set forth in SEQ ID NO: 7.

In particular embodiments, the variable light chain sequence comprises the CDR sequences set forth in SEQ ID NOs: 1-3.

In other embodiments, the murine anti-BCMA antibody or antigen binding fragment thereof comprises a variable heavy chain sequence as set forth in SEQ ID NO: 8.

In additional embodiments, the variable heavy chain sequence comprises the CDR sequences set forth in SEQ ID NOs: 4-6.

In further embodiments, the transmembrane domain is from a polypeptide selected from the group consisting of: alpha, beta or zeta chain of the T-cell receptor, CD3ε, CD3ζ, CD4, CD5, CD8α, CD9, CD16, CD22, CD27, CD28, CD33, CD37, CD45, CD64, CD80, CD86, CD134, CD137, CD152, CD154, and PD1.

In some embodiments, the transmembrane domain is from a polypeptide selected from the group consisting of: CD8α; CD4, CD45, PD1, and CD154.

In certain embodiments, the transmembrane domain is from CD8α.

In particular embodiments, the one or more co-stimulatory signaling domains are from a co-stimulatory molecule selected from the group consisting of: CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70.

In particular embodiments, the one or more co-stimulatory signaling domains are from a co-stimulatory molecule selected from the group consisting of: CD28, CD134, and CD137.

In additional embodiments, the one or more co-stimulatory signaling domains are from a co-stimulatory molecule selected from the group consisting of: CD28, CD134, and CD137.

In additional embodiments, the one or more co-stimulatory signaling domains is from CD28.

In particular embodiments, the one or more co-stimulatory signaling domains is from CD134.

In other embodiments, the one or more co-stimulatory signaling domains is from CD137.

In certain embodiments, a CAR comprises a hinge region polypeptide.

In further embodiments, the hinge region polypeptide comprises a hinge region of CD8α.

In some embodiments, a CAR comprises a spacer region.

In additional embodiments, the spacer region polypeptide comprises CH2 and CH3 regions of IgG1 or IgG4.

In particular embodiments, a CAR comprises a signal peptide.

In further embodiments, the signal peptide comprises an IgG1 heavy chain signal polypeptide, granulocyte-macrophage colony stimulating factor receptor 2 (GM-CSFR2) signal peptide, or a CD8α signal polypeptide.

In one embodiment, a CAR comprises an amino acid sequence as set forth in SEQ ID NO: 9.

In various embodiments, a polynucleotide encoding a CAR contemplated herein, is provided.

In various particular embodiments, a polynucleotide encoding a CAR is provided, wherein the polynucleotide sequence is set forth in SEQ ID NO: 10.

In various certain embodiments, a vector comprising a polynucleotide encoding a CAR contemplated herein or as set forth in SEQ ID NO: 10 is provided.

In certain embodiments, the vector is an expression vector.

In additional embodiments, the vector is an episomal vector.

In particular embodiments, the vector is a viral vector.

In further embodiments, the vector is a retroviral vector.

In other embodiments, the vector is a lentiviral vector.

In one embodiment, a vector encoding a BCMA CAR comprises the polynucleotide sequence set forth in SEQ ID NO: 36.

In additional embodiments, the lentiviral vector is selected from the group consisting essentially of: human immunodeficiency virus 1 (HIV-1); human immunodeficiency virus 2 (HIV-2), visna-maedi virus (VMV) virus; caprine arthritis-encephalitis virus (CAEV); equine infectious anemia virus (EIAV); feline immunodeficiency virus (FIV); bovine immune deficiency virus (BIV); and simian immunodeficiency virus (SIV).

In particular embodiments, a vector comprises a left (5') retroviral LTR, a Psi (Ψ) packaging signal, a central polypurine tract/DNA flap (cPPT/FLAP), a retroviral export element; a promoter operably linked to the polynucleotide encoding a CAR contemplated herein; and a right (3') retroviral LTR.

In other embodiments, a CAR comprises a heterologous polyadenylation sequence.

In some embodiments, a CAR comprises a hepatitis B virus posttranscriptional regulatory element (HPRE) or woodchuck post-transcriptional regulatory element (WPRE).

In certain embodiments, the promoter of the 5' LTR is replaced with a heterologous promoter.

In further embodiments, the heterologous promoter is a cytomegalovirus (CMV) promoter, a Rous Sarcoma Virus (RSV) promoter, or an Simian Virus 40 (SV40) promoter.

In particular embodiments, the 5' LTR or 3' LTR is a lentivirus LTR.

In particular embodiments, the 3' LTR comprises one or more modifications.

In some embodiments, the 3' LTR comprises one or more deletions.

In certain embodiments, the 3' LTR is a self-inactivating (SIN) LTR.

In some embodiments, the polyadenylation sequence is a bovine growth hormone polyadenylation or signal rabbit β-globin polyadenylation sequence.

In additional embodiments, a polynucleotide encoding a CAR contemplated herein comprises an optimized Kozak sequence.

In further embodiments, the promoter operably linked to the polynucleotide encoding a CAR contemplated herein is selected from the group consisting of: a cytomegalovirus immediate early gene promoter (CMV), an elongation factor 1 alpha promoter (EF1-α), a phosphoglycerate kinase-1 promoter (PGK), a ubiquitin-C promoter (UBQ-C), a cytomegalovirus enhancer/chicken beta-actin promoter (CAG), polyoma enhancer/herpes simplex thymidine kinase promoter (MC1), a beta actin promoter (β-ACT), a simian virus 40 promoter (SV40), and a myeloproliferative sarcoma virus enhancer, negative control region deleted, d1587rev primer-binding site substituted (MND) promoter.

In various embodiments, an immune effector cell is provided comprising a vector contemplated herein. In various embodiments, the immune effector cell is transduced with a vector contemplated herein.

In further embodiments, the immune effector cell is selected from the group consisting of: a T lymphocyte and a natural killer (NK) cell.

In some embodiments, the immune effector cell is transduced with the vector of any one of the embodiments described above and is activated and stimulated in the presence of an inhibitor of the PI3K pathway, thereby maintaining proliferation of the transduced immune effector cells compared to the proliferation of transduced immune effector cells that were activated and stimulated in the absence of the inhibitor of the PI3K pathway.

In particular embodiments, the immune effector cell activated and stimulated in the presence of the inhibitor of PI3K pathway has increased expression of i) one or more markers selected from the group consisting of: CD62L, CD127, CD197, and CD38 or ii) all of the markers CD62L, CD127, CD197, and CD38 compared to an immune effector cell activated and stimulated in the absence of the inhibitor of PI3K pathway.

In one embodiment, the PI3K inhibitor is ZSTK474.

In various embodiments, a composition is provided comprising an immune effector cell contemplated herein and a physiologically acceptable excipient.

In various embodiments, a method of generating an immune effector cell comprising a CAR contemplated herein is provided, comprising introducing into an immune effector cell a vector comprising a polynucleotide encoding the CAR.

In additional embodiments, the method further comprises stimulating the immune effector cell and inducing the cell to proliferate by contacting the cell with antibodies that bind CD3 and antibodies that bind to CD28; thereby generating a population of immune effector cells.

In particular embodiments, the immune effector cell is stimulated and induced to proliferate before introducing the vector.

In certain embodiments, the immune effector cells comprise T lymphocytes.

In particular embodiments, the immune effector cells comprise NK cells.

In particular embodiments, the cells are the activated and stimulated in the presence of an inhibitor of the PI3K pathway, thereby maintaining proliferation of the transduced immune effector cells compared to the proliferation of immune effector cells that are activated and stimulated in the absence of the inhibitor of the PI3K pathway In some embodiments, the immune effector cells activated and stimulated in the presence of the inhibitor of PI3K pathway have increased expression of i) one or more markers selected from the group consisting of: CD62L, CD127, CD197, and CD38 or ii) all of the markers CD62L, CD127, CD197, and CD38 compared to immune effector cells activated and stimulated in the absence of the inhibitor of PI3K pathway.

In one embodiment, the PI3K inhibitor is ZSTK474.

In various embodiments, a method of treating a B cell related condition in a subject in need thereof is provided, comprising administering to the subject a therapeutically effect amount of a composition comprising BCMA CAR T cells contemplated herein and optionally, a pharmaceutically acceptable excipient.

In other embodiments, the B cell related condition is multiple myeloma, non-Hodgkin's lymphoma, B cell proliferations of uncertain malignant potential, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis *nodosa*, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, or monoclonal gammopathy of undetermined significance.

In further embodiments, the B cell related condition is a B cell malignancy.

In certain embodiments, the B cell malignancy is multiple myeloma (MM) or non-Hodgkin's lymphoma (NHL).

In certain embodiments, the MM is selected from the group consisting of: overt multiple myeloma, smoldering multiple myeloma, plasma cell leukemia, non-secretory myeloma, IgD myeloma, osteosclerotic myeloma, solitary plasmacytoma of bone, and extramedullary plasmacytoma.

In some embodiments, the NHL is selected from the group consisting of: Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma.

In particular embodiments, the B cell related condition is a plasma cell malignancy.

In further embodiments, the B cell related condition is an autoimmune disease.

In additional embodiments, the autoimmune disease is systemic lupus erythematosus.

In certain embodiments, the B cell related condition is rheumatoid arthritis.

In particular embodiments, the B cell related condition is idiopathic thrombocytopenia purpura, or myasthenia gravis, or autoimmune hemolytic anemia.

BRIEF DESCRIPTION OF SEVERAL VIEWS OF THE DRAWINGS

FIG. 11A shows T cell populations were transduced with between $4 \times 10^8$ and $5 \times 10^7$ transducing units of a lentivirus encoding an anti-BCMA CAR molecule (MOI of 5 to 40). The resulting T cell populations were normalized to contain 26±4% anti-BCMA CAR-positive T cells. FIG. 11B shows MFI of the normalized anti-BCMA CAR T cells ranged from 885 to 1875 as assayed by flow cytometry. FIG. 11C shows K562 cells and K562-BCMA cells were co-cultured with normalized anti-BCMA CAR T cells at a 20:1 or 10:1 effector (E; T cell) to target (T; 1:1 mix of K562 and K562 BCMA cells) ratio showed comparable cytolytic activity.

FIG. 12A shows anti-BCMA CAR T cell products manufactured from PBMCs of 11 individual donors show comparable levels of expansion compared to a matched culture of untransduced donor T cells. FIG. 12B shows anti-BCMA CAR T cell products manufactured from the 11 donors showed comparable lentiviral transduction efficiency (VCN). FIG. 12C shows the frequency of anti-BCMA CAR positive T cells was measured by flow cytometry and BCMA expression was found to be comparable across all donors. FIG. 12D shows anti-BCMA CAR T cell products manufactured from the 11 donors showed therapeutically relevant levels of IFNγ release when exposed to BCMA-expressing K562 cells.

BRIEF DESCRIPTION OF THE SEQUENCE IDENTIFIERS

Figure 1:
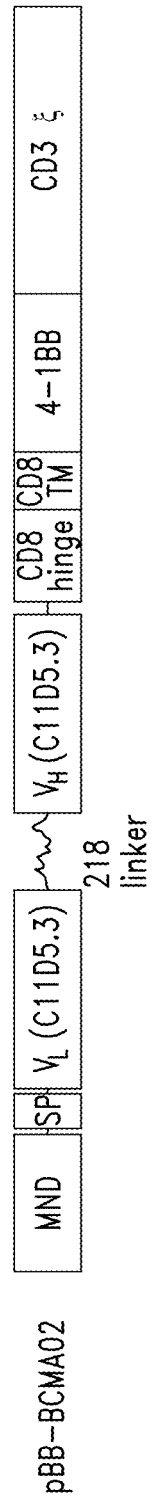
FIG. 1 shows a schematic of murine B cell maturation antigen (muBCMA) CAR constructs.

SEQ ID NOs: 1-3 set forth amino acid sequences of exemplary light chain CDR sequences for BCMA CARs contemplated herein.

SEQ ID NOs: 4-6 set forth amino acid sequences of exemplary heavy chain CDR sequences for BCMA CARs contemplated herein.

SEQ ID NO: 7 sets forth an amino acid sequence of an exemplary light chain sequences for BCMA CARs contemplated herein.

SEQ ID NO: 8 sets forth an amino acid sequence of an exemplary heavy chain sequences for BCMA CARs contemplated herein.

SEQ ID NO: 9 sets forth an amino acid sequence of an exemplary BCMA CAR contemplated herein.

SEQ ID NO: 10 set forth a polynucleotide sequence that encode an exemplary BCMA CAR contemplated herein.

SEQ ID NO: 11 sets forth the amino acid sequence of human BCMA.

SEQ ID NO: 12-22 set for the amino acid sequence of various linkers.

SEQ ID NOs: 23-35 set for the amino acid sequence of protease cleavage sites and self-cleaving polypeptide cleavage sites.

SEQ ID NO: 36 sets for the polynucleotide sequence of a vector encoding a BCMA CAR.

DETAILED DESCRIPTION

A. Overview

The invention generally relates to improved compositions and methods for treating B cell related conditions. As used herein, the term "B cell related conditions" relates to conditions involving inappropriate B cell activity and B cell malignancies.

In particular embodiments, the invention relates to improved adoptive cell therapy of B cell related conditions using genetically modified immune effector cells. Genetic approaches offer a potential means to enhance immune recognition and elimination of cancer cells. One promising strategy is to genetically engineer immune effector cells to express chimeric antigen receptors (CAR) that redirect cytotoxicity toward cancer cells. However, existing adoptive cell immunotherapies for treating B cell disorders present a serious risk of compromising humoral immunity because the cells target antigens expressed on all of, or the majority of, B cells. Accordingly, such therapies are not clinically desirable and thus, a need in the art remains for more efficient therapies for B cell related conditions that spare humoral immunity.

The improved compositions and methods of adoptive cell therapy disclosed herein, provide genetically modified immune effector cells that can readily be expanded, exhibit long-term persistence in vivo, and reduce impairment of humoral immunity by targeting B cells expression B cell maturation antigen (BCMA, also known as CD269 or tumor necrosis factor receptor superfamily, member 17; TNFRSF17).

BCMA is a member of the tumor necrosis factor receptor superfamily (see, e.g., Thompson et al., *J. Exp. Medicine*, 192(1): 129-135, 2000, and Mackay et al., *Annu. Rev.*

*Immunol*, 21: 231-264, 2003. BCMA binds B-cell activating factor (BAFF) and a proliferation inducing ligand (APRIL) (see, e.g., Mackay et al., 2003 and Kalled et al., *Immunological Reviews*, 204: 43-54, 2005). Among nonmalignant cells, BCMA has been reported to be expressed mostly in plasma cells and subsets of mature B-cells (see, e.g., Laabi et al., *EMBO J.*, 77(1): 3897-3904, 1992; Laabi et al., *Nucleic Acids Res.*, 22(7): 1147-1154, 1994; Kalled et al., 2005; O'Connor et al., *J. Exp. Medicine*, 199(1): 91-97, 2004; and Ng et al., *J. Immunol.*, 73(2): 807-817, 2004. Mice deficient in BCMA are healthy and have normal numbers of B cells, but the survival of long-lived plasma cells is impaired (see, e.g., O'Connor et al., 2004; Xu et al., *Mol. Cell. Biol*, 21(12): 4067-4074, 2001; and Schiemann et al., *Science*, 293(5537): 2 111-21 14, 2001). BCMA RNA has been detected universally in multiple myeloma cells and in other lymphomas, and BCMA protein has been detected on the surface of plasma cells from multiple myeloma patients by several investigators (see, e.g., Novak et al., *Blood*, 103(2): 689-694, 2004; Neri et al., *Clinical Cancer Research*, 73(19): 5903-5909, 2007; Bellucci et al., *Blood*, 105(10): 3945-3950, 2005; and Moreaux et al., *Blood*, 703(8): 3148-3157, 2004.

In various embodiments, CARs comprising murine anti-BCMA antibody sequences are highly efficacious compared to BCMA CARs comprising particular human antibody sequences; undergo robust in vivo expansion; and recognize human B cells expressing BMCA; show cytotoxic activity against the BCMA expressing B cells; and do not show signs of inducing a cytokine storm, a potentially fatal condition where the cytokines released by activated T cells create a sudden inflammatory response in the system that spurs a noninfectious fever.

In one embodiment, a CAR comprising a murine anti-BCMA antibody or antigen binding fragment, a transmembrane domain, and one or more intracellular signaling domains is provided.

In one embodiment, an immune effector cell is genetically modified to express a CAR contemplated herein is provided. T cells expressing a CAR are referred to herein as CAR T cells or CAR modified T cells.

In various embodiments, the genetically modified immune effector cells contemplated herein, are administered to a patient with a B cell related condition, e.g., an autoimmune disease associated with B cells or a B cell malignancy.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology Q*. E. Coligan, A. M. Kruisbeek, D. H. Margulies, E. M. Shevach and W. Strober, eds., 1991); *Annual Review of Immunology*; as well as monographs in journals such as Advances in Immunology.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length $\pm 15\%$, $\pm 10\%$, $\pm 9\%$, $\pm 8\%$, $\pm 7\%$, $\pm 6\%$, $\pm 5\%$, $\pm 4\%$, $\pm 3\%$, $\pm 2\%$, or $\pm 1\%$ about a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

C. Chimeric Antigen Receptors

In various embodiments, genetically engineered receptors that redirect cytotoxicity of immune effector cells toward B cells are provided. These genetically engineered receptors referred to herein as chimeric antigen receptors (CARs). CARs are molecules that combine antibody-based specificity for a desired antigen (e.g., BCMA) with a T cell receptor-activating intracellular domain to generate a chimeric protein that exhibits a specific anti-BCMA cellular immune activity. As used herein, the term, "chimeric," describes being composed of parts of different proteins or DNAs from different origins.

CARs contemplated herein, comprise an extracellular domain (also referred to as a binding domain or antigen-specific binding domain) that binds to BCMA, a transmembrane domain, and an intracellular signaling domain. Engagement of the anti-BCMA antigen binding domain of the CAR with BCMA on the surface of a target cell results in clustering of the CAR and delivers an activation stimulus to the CAR-containing cell. The main characteristic of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific co-receptors.

In various embodiments, a CAR comprises an extracellular binding domain that comprises a murine anti-BCMA-specific binding domain; a transmembrane domain; one or more intracellular co-stimulatory signaling domains; and a primary signaling domain.

In particular embodiments, a CAR comprises an extracellular binding domain that comprises a murine anti-BCMA antibody or antigen binding fragment thereof; one or more hinge domains or spacer domains; a transmembrane domain including; one or more intracellular co-stimulatory signaling domains; and a primary signaling domain.

1. Binding Domain

In particular embodiments, CARs contemplated herein comprise an extracellular binding domain that comprises a murine anti-BCMA antibody or antigen binding fragment thereof that specifically binds to a human BCMA polypeptide expressed on a B cell. As used herein, the terms, "binding domain," "extracellular domain," "extracellular binding domain," "antigen-specific binding domain," and "extracellular antigen specific binding domain," are used interchangeably and provide a CAR with the ability to specifically bind to the target antigen of interest, e.g., BCMA. The binding domain may be derived either from a natural, synthetic, semi-synthetic, or recombinant source.

The terms "specific binding affinity" or "specifically binds" or "specifically bound" or "specific binding" or "specifically targets" as used herein, describe binding of an anti-BCMA antibody or antigen binding fragment thereof (or a CAR comprising the same) to BCMA at greater binding affinity than background binding. A binding domain (or a CAR comprising a binding domain or a fusion protein containing a binding domain) "specifically binds" to a BCMA if it binds to or associates with BCMA with an affinity or $K_a$ (i.e., an equilibrium association constant of a particular binding interaction with units of 1/M) of, for example, greater than or equal to about $10^5$ $M^{-1}$. In certain embodiments, a binding domain (or a fusion protein thereof) binds to a target with a Ka greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" binding domains (or single chain fusion proteins thereof) refers to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater.

Alternatively, affinity may be defined as an equilibrium dissociation constant ($K_d$) of a particular binding interaction with units of M (e.g., $10^{-5}$ M to $10^{-13}$ M, or less). Affinities of binding domain polypeptides and CAR proteins according to the present disclosure can be readily determined using conventional techniques, e.g., by competitive ELISA (enzyme-linked immunosorbent assay), or by binding association, or displacement assays using labeled ligands, or using a surface-plasmon resonance device such as the Biacore T100, which is available from Biacore, Inc., Piscataway, N.J., or optical biosensor technology such as the EPIC system or EnSpire that are available from Corning and Perkin Elmer respectively (see also, e.g., Scatchard et al. (1949) Ann. N.Y. Acad. Sci. 51:660; and U.S. Pat. Nos. 5,283,173; 5,468,614, or the equivalent).

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

In particular embodiments, the extracellular binding domain of a CAR comprises an antibody or antigen binding fragment thereof. An "antibody" refers to a binding agent that is a polypeptide comprising at least a light chain or heavy chain immunoglobulin variable region which specifically recognizes and binds an epitope of an antigen, such as a peptide, lipid, polysaccharide, or nucleic acid containing an antigenic determinant, such as those recognized by an immune cell.

An "antigen (Ag)" refers to a compound, composition, or substance that can stimulate the production of antibodies or a T cell response in an animal, including compositions (such as one that includes a cancer-specific protein) that are injected or absorbed into an animal. An antigen reacts with the products of specific humoral or cellular immunity, including those induced by heterologous antigens, such as the disclosed antigens. In particular embodiments, the target antigen is an epitope of a BCMA polypeptide.

An "epitope" or "antigenic determinant" refers to the region of an antigen to which a binding agent binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation.

Antibodies include antigen binding fragments thereof, such as Camel Ig, Ig NAR, Fab fragments, Fab' fragments, F(ab)'$_2$ fragments, F(ab)'$_3$ fragments, Fv, single chain Fv proteins ("scFv"), bis-scFv, (scFv)$_2$, minibodies, diabodies, triabodies, tetrabodies, disulfide stabilized Fv proteins ("dsFv"), and single-domain antibody (sdAb, Nanobody) and portions of full length antibodies responsible for antigen binding. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, Ill.); Kuby, J., Immunology, 3rd Ed., W. H. Freeman & Co., New York, 1997.

As would be understood by the skilled person and as described elsewhere herein, a complete antibody comprises two heavy chains and two light chains. Each heavy chain consists of a variable region and a first, second, and third constant region, while each light chain consists of a variable region and a constant region. Mammalian heavy chains are classified as α, δ, ε, γ, and μ. Mammalian light chains are classified as λ or κ. Immunoglobulins comprising the α, δ, ε, γ, and μ heavy chains are classified as immunoglobulin (Ig)A, IgD, IgE, IgG, and IgM. The complete antibody forms a "Y" shape. The stem of the Y consists of the second and third constant regions (and for IgE and IgM, the fourth constant region) of two heavy chains bound together and disulfide bonds (inter-chain) are formed in the hinge. Heavy chains γ, α and δ have a constant region composed of three tandem (in a line) Ig domains, and a hinge region for added flexibility; heavy chains μ and ε have a constant region composed of four immunoglobulin domains. The second and third constant regions are referred to as "CH2 domain" and "CH3 domain", respectively. Each arm of the Y includes the variable region and first constant region of a single heavy chain bound to the variable and constant regions of a single light chain. The variable regions of the light and heavy chains are responsible for antigen binding.

Light and heavy chain variable regions contain a "framework" region interrupted by three hypervariable regions, also called "complementarity-determining regions" or "CDRs." The CDRs can be defined or identified by conventional methods, such as by sequence according to Kabat et al (Wu, T T and Kabat, E. A., *J Exp Med.* 132(2):211-50, (1970); Borden, P. and Kabat E. A., *PNAS,* 84: 2440-2443 (1987); (see, Kabat et al., *Sequences of Proteins of Immunological Interest,* U.S. Department of Health and Human Services, 1991, which is hereby incorporated by reference), or by structure according to Chothia et al (Choithia, C. and Lesk, A. M., *J Mol. Biol.,* 196(4): 901-917 (1987), Choithia, C. et al, *Nature,* 342: 877-883 (1989)).

The sequences of the framework regions of different light or heavy chains are relatively conserved within a species, such as humans. The framework region of an antibody, that is the combined framework regions of the constituent light and heavy chains, serves to position and align the CDRs in three-dimensional space. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, the CDRs located in the variable domain of the heavy chain of the antibody are referred to as CDRH1, CDRH2, and CDRH3, whereas the CDRs located in the variable domain of the light chain of the antibody are referred to as CDRL1, CDRL2, and CDRL3. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). Illustrative examples of light chain CDRs that are suitable for constructing humanized BCMA CARs contemplated herein include, but are not limited to the CDR sequences set forth in SEQ ID NOs: 1-3. Illustrative examples of heavy chain CDRs that are suitable for constructing humanized BCMA CARs contemplated herein include, but are not limited to the CDR sequences set forth in SEQ ID NOs: 4-6.

References to "V$_H$" or "VH" refer to the variable region of an immunoglobulin heavy chain, including that of an antibody, Fv, scFv, dsFv, Fab, or other antibody fragment as disclosed herein. References to "V$_L$" or "VL" refer to the variable region of an immunoglobulin light chain, including that of an antibody, Fv, scFv, dsFv, Fab, or other antibody fragment as disclosed herein.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a mouse. In particular preferred embodiments, a CAR contemplated herein comprises antigen-specific binding domain that is a chimeric antibody or antigen binding fragment thereof.

A "humanized" antibody is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor."

In particular embodiments, a murine anti-BCMA antibody or antigen binding fragment thereof, includes but is not limited to a Camel Ig (a camelid antibody (VHH)), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody).

"Camel Ig" or "camelid VHH" as used herein refers to the smallest known antigen-binding unit of a heavy chain antibody (Koch-Nolte, et al, FASEB J., 21: 3490-3498 (2007)). A "heavy chain antibody" or a "camelid antibody" refers to an antibody that contains two VH domains and no light chains (Riechmann L. et al, J. Immunol. Methods 231:25-38 (1999); WO94/04678; WO94/25591; U.S. Pat. No. 6,005,079).

"IgNAR" of "immunoglobulin new antigen receptor" refers to class of antibodies from the shark immune repertoire that consist of homodimers of one variable new antigen receptor (VNAR) domain and five constant new antigen receptor (CNAR) domains. IgNARs represent some of the smallest known immunoglobulin-based protein scaffolds and are highly stable and possess efficient binding characteristics. The inherent stability can be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulphide bridges, and patterns of intra-loop hydrogen bonds.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy-and one light-chain variable domain can be covalently linked by a flexible peptide linker such that the light and heavy chains can associate in a "dimeric" structure analogous to that in a two-chain Fv species. It is in this configuration that the three hypervariable regions (HVRs) of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., Nat. Med. 9:129-134 (2003); and Hollinger et al., PNAS USA 90: 6444-6448 (1993). Triabodies and tetrabodies are also described in Hudson et al., Nat. Med. 9:129-134 (2003).

"Single domain antibody" or "sdAb" or "nanobody" refers to an antibody fragment that consists of the variable region of an antibody heavy chain (VH domain) or the variable region of an antibody light chain (VL domain) (Holt, L., et al, Trends in Biotechnology, 21(11): 484-490).

"Single-chain Fv" or "scFv" antibody fragments comprise the VH and VL domains of antibody, wherein these domains are present in a single polypeptide chain and in either orientation (e.g., VL-VH or VH-VL). Generally, the scFv polypeptide further comprises a polypeptide linker between the VH and VL domains which enables the scFv to form the desired structure for antigen binding. For a review of scFv, see, e.g., Pluckthun, in The Pharmacology of Monoclonal Antibodies, vol. 113, Rosenburg and Moore eds., (Springer-Verlag, New York, 1994), pp. 269-315.

In preferred embodiments, a CAR contemplated herein comprises antigen-specific binding domain that is a murine scFv. Single chain antibodies may be cloned form the V region genes of a hybridoma specific for a desired target. The production of such hybridomas has become routine. A technique which can be used for cloning the variable region heavy chain ($V_H$) and variable region light chain ($V_L$) has been described, for example, in Orlandi et al., *PNAS,* 1989; 86: 3833-3837.

In particular embodiments, the antigen-specific binding domain that is a murine scFv that binds a human BCMA polypeptide. Illustrative examples of variable heavy chains that are suitable for constructing BCMA CARs contemplated herein include, but are not limited to the amino acid sequences set forth in SEQ ID NO: 8. Illustrative examples of variable light chains that are suitable for constructing BCMA CARs contemplated herein include, but are not limited to the amino acid sequences set forth in SEQ ID NO: 7.

BCMA-specific binding domains provided herein also comprise one, two, three, four, five, or six CDRs. Such CDRs may be nonhuman CDRs or altered nonhuman CDRs selected from CDRL1, CDRL2 and CDRL3 of the light chain and CDRH1, CDRH2 and CDRH3 of the heavy chain. In certain embodiments, a BCMA-specific binding domain comprises (a) a light chain variable region that comprises a light chain CDRL1, a light chain CDRL2, and a light chain CDRL3, and (b) a heavy chain variable region that comprises a heavy chain CDRH1, a heavy chain CDRH2, and a heavy chain CDRH3.

2. Linkers

In certain embodiments, the CARs contemplated herein may comprise linker residues between the various domains, e.g., added for appropriate spacing and conformation of the molecule. In particular embodiments the linker is a variable region linking sequence. A "variable region linking sequence," is an amino acid sequence that connects the $V_H$ and $V_L$ domains and provides a spacer function compatible with interaction of the two sub-binding domains so that the resulting polypeptide retains a specific binding affinity to the same target molecule as an antibody that comprises the same light and heavy chain variable regions. CARs contemplated herein, may comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers $(G)_n$; glycine-serine polymers $(G_{1-5}S_{1-5})_n$, where n is an integer of at least one, two, three, four, or five; glycine-alanine polymers; alanine-serine polymers; and other flexible linkers known in the art. Glycine and glycine-serine polymers are relatively unstructured, and therefore may be able to serve as a neutral tether between domains of fusion proteins such as the CARs described herein. Glycine accesses significantly more phi-psi space than even alanine, and is much less restricted than residues with longer side chains (see Scheraga, *Rev. Computational Chem.* 11173-142 (1992)). The ordinarily skilled artisan will recognize that design of a CAR in particular embodiments can include linkers that are all or partially flexible, such that the linker can include a flexible linker as well as one or more portions that confer less flexible structure to provide for a desired CAR structure.

Other exemplary linkers include, but are not limited to the following amino acid sequences: GGG; DGGGS (SEQ ID NO: 12); TGEKP (SEQ ID NO: 13) (see, e.g., Liu et al., PNAS 5525-5530 (1997)); GGRR (SEQ ID NO: 14) (Pomerantz et al. 1995, supra); (GGGGS)$_n$ wherein=1, 2, 3, 4 or 5 (SEQ ID NO: 15) (Kim et al., PNAS 93, 1156-1160 (1996.); EGKSSGSGSESKVD (SEQ ID NO: 16) (Chaudhary et al., 1990, Proc. Natl. Acad. Sci. U.S.A. 87:1066-1070); KESGSVSSEQLAQFRSLD (SEQ ID NO: 17) (Bird et al., 1988, Science 242:423-426), GGRRGGGS (SEQ ID NO: 18); LRQRDGERP (SEQ ID NO: 19); LRQKDGGGSERP (SEQ ID NO: 20); LRQKd(GGGS)$_2$ ERP (SEQ ID NO: 21). Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods. In one embodiment, the linker comprises the following amino acid sequence: GSTSGSGKPGSGEGSTKG (SEQ ID NO: 22) (Cooper et al., *Blood*, 101(4): 1637-1644 (2003)).

3. Spacer Domain

In particular embodiments, the binding domain of the CAR is followed by one or more "spacer domains," which refers to the region that moves the antigen binding domain away from the effector cell surface to enable proper cell/cell contact, antigen binding and activation (Patel et al., *Gene Therapy*, 1999; 6: 412-419). The hinge domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

In one embodiment, the spacer domain comprises the CH2 and CH3 domains of IgG1 or IgG4.

4. Hinge Domain

The binding domain of the CAR is generally followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region.

An "altered hinge region" refers to (a) a naturally occurring hinge region with up to 30% amino acid changes (e.g., up to 25%, 20%, 15%, 10%, or 5% amino acid substitutions or deletions), (b) a portion of a naturally occurring hinge region that is at least 10 amino acids (e.g., at least 12, 13, 14 or 15 amino acids) in length with up to 30% amino acid changes (e.g., up to 25%, 20%, 15%, 10%, or 5% amino acid substitutions or deletions), or (c) a portion of a naturally occurring hinge region that comprises the core hinge region (which may be 4, 5, 6, 7, 8, 9, 10, 11, 12, 13, 14, or 15, or at least 4, 5, 6, 7, 8, 9, 10, 11, 12, 13, 14, or 15 amino acids in length). In certain embodiments, one or more cysteine residues in a naturally occurring immunoglobulin hinge region may be substituted by one or more other amino acid residues (e.g., one or more serine residues). An altered immunoglobulin hinge region may alternatively or additionally have a proline residue of a wild type immunoglobulin hinge region substituted by another amino acid residue (e.g., a serine residue).

Other illustrative hinge domains suitable for use in the CARs described herein include the hinge region derived from the extracellular regions of type 1 membrane proteins such as CD8α, CD4, CD28 and CD7, which may be wild-type hinge regions from these molecules or may be altered. In another embodiment, the hinge domain comprises a CD8a hinge region.

5. Transmembrane (TM) Domain

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source. The TM domain may be derived from (i.e., comprise at least the transmembrane region(s) of) the alpha, beta or zeta chain of the T-cell receptor, CD3ε, CD3ζ, CD4, CD5, CD8α, CD9, CD16, CD22, CD27, CD28, CD33, CD37, CD45, CD64, CD80, CD86, CD134, CD137, CD152, CD154, and PD1. In a particular embodiment, the TM domain is synthetic and predominantly comprises hydrophobic residues such as leucine and valine.

In one embodiment, the CARs contemplated herein comprise a TM domain derived from CD8α. In another embodiment, a CAR contemplated herein comprises a TM domain derived from CD8α and a short oligo- or polypeptide linker, preferably between 1, 2, 3, 4, 5, 6, 7, 8, 9, or 10 amino acids in length that links the TM domain and the intracellular signaling domain of the CAR. A glycine-serine based linker provides a particularly suitable linker.

6. Intracellular Signaling Domain

In particular embodiments, CARs contemplated herein comprise an intracellular signaling domain. An "intracellular signaling domain," refers to the part of a CAR that participates in transducing the message of effective BCMA CAR binding to a human BCMA polypeptide into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function" refers to a specialized function of an immune effector cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or co-stimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and co-stimulatory signaling domains that act in an antigen-independent manner to provide a secondary or co-stimulatory signal. In preferred embodiments, a CAR contemplated herein comprises an intracellular signaling domain that comprises one or more "co-stimulatory signaling domain" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs.

Illustrative examples of ITAM containing primary signaling domains that are of particular use in the invention include those derived from TCRζ, FcRγ, FcRβ, CD3γ, CD3δ, CD3ε, CD3ζ, CD22, CD79a, CD79b, and CD66d. In particular preferred embodiments, a CAR comprises a CD3ζ primary signaling domain and one or more co-stimulatory signaling domains. The intracellular primary signaling and co-stimulatory signaling domains may be linked in any order in tandem to the carboxyl terminus of the transmembrane domain.

CARs contemplated herein comprise one or more co-stimulatory signaling domains to enhance the efficacy and expansion of T cells expressing CAR receptors. As used herein, the term, "co-stimulatory signaling domain," or "co-stimulatory domain", refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70. In one embodiment, a CAR comprises one or more co-stimulatory signaling domains selected from the group consisting of CD28, CD137, and CD134, and a CD3ζ primary signaling domain.

In another embodiment, a CAR comprises CD28 and CD137 co-stimulatory signaling domains and a CD3ζ primary signaling domain.

In yet another embodiment, a CAR comprises CD28 and CD134 co-stimulatory signaling domains and a CD3ζ primary signaling domain.

In one embodiment, a CAR comprises CD137 and CD134 co-stimulatory signaling domains and a CD3ζ primary signaling domain.

In particular embodiments, CARs contemplated herein comprise a murine anti-BCMA antibody or antigen binding fragment thereof that specifically binds to a BCMA polypeptide expressed on B cells.

In one embodiment, a CAR comprises a murine anti-BCMA scFv that binds a BCMA polypeptide; a transmembrane domain derived from a polypeptide selected from the group consisting of: alpha, beta or zeta chain of the T-cell receptor, CD3ε, CD3ζ, CD4, CD5, CD8α, CD9, CD16, CD22, CD27, CD28, CD33, CD37, CD45, CD64, CD80, CD86, CD134, CD137, CD152, CD154, and PD1; and one or more intracellular co-stimulatory signaling domains from a co-stimulatory molecule selected from the group consisting of: CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70; and a primary signaling domain from TCRζ, FcRγ, FcRβ, CD3γ, CD3δ, CD3ε, CD3ζ, CD22, CD79a, CD79b, and CD66d.

In one embodiment, a CAR comprises a murine anti-BCMA scFv that binds a BCMA polypeptide; a hinge domain selected from the group consisting of: IgG1 hinge/CH2/CH3, IgG4 hinge/CH2/CH3, and a CD8a hinge; a transmembrane domain derived from a polypeptide selected from the group consisting of: alpha, beta or zeta chain of the T-cell receptor, CD3ε, CD3ζ, CD4, CD5, CD8α, CD9, CD16, CD22, CD27, CD28, CD33, CD37, CD45, CD64, CD80, CD86, CD134, CD137, CD152, CD 154, and PD1; and one or more intracellular co-stimulatory signaling domains from a co-stimulatory molecule selected from the group consisting of: CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70; and a primary signaling domain from TCRζ, FcRγ, FcRβ, CD3γ, CD3δ, CD3ε, CD3ζ, CD22, CD79a, CD79b, and CD66d.

In one embodiment, a CAR comprises a murine anti-BCMA scFv that binds a BCMA polypeptide; a hinge domain selected from the group consisting of: IgG1 hinge/CH2/CH3, IgG4 hinge/CH2/CH3, and a CD8α hinge; a transmembrane domain derived from a polypeptide selected from the group consisting of: alpha, beta or zeta chain of the T-cell receptor, CD3ε, CD3ζ, CD4, CD5, CD8α, CD9, CD16, CD22, CD27, CD28, CD33, CD37, CD45, CD64, CD80, CD86, CD134, CD137, CD152, CD 154, and PD1; a short oligo- or polypeptide linker, preferably between 1, 2, 3, 4, 5, 6, 7, 8, 9, or 10 amino acids in length that links the TM domain to the intracellular signaling domain of the CAR; and one or more intracellular co-stimulatory signaling domains from a co-stimulatory molecule selected from the group consisting of: CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70; and a primary signaling domain from TCR, FcRγ, FcRβ, CD3γ, CD3δ, CD3ε, CD3ζ, CD22, CD79a, CD79b, and CD66d.

In a particular embodiment, a CAR comprises a murine anti-BCMA scFv that binds a BCMA polypeptide; a hinge domain comprising an IgG1 hinge/CH2/CH3 polypeptide and a CD8α polypeptide; a CD8α transmembrane domain comprising a polypeptide linker of about 3 to about 10 amino acids; a CD137 intracellular co-stimulatory signaling domain; and a CD3ζ primary signaling domain.

In a particular embodiment, a CAR comprises a murine anti-BCMA scFv that binds a BCMA polypeptide; a hinge domain comprising a CD8α polypeptide; a CD8α transmembrane domain comprising a polypeptide linker of about 3 to about 10 amino acids; a CD134 intracellular co-stimulatory signaling domain; and a CD3ζ primary signaling domain.

In a particular embodiment, a CAR comprises a murine anti-BCMA scFv that binds a BCMA polypeptide; a hinge domain comprising a CD8α polypeptide; a CD8α transmembrane domain comprising a polypeptide linker of about 3 to about 10 amino acids; a CD28 intracellular co-stimulatory signaling domain; and a CD3ζ primary signaling domain.

Moreover, the design of the CARs contemplated herein enable improved expansion, long-term persistence, and tolerable cytotoxic properties in T cells expressing the CARs compared to non-modified T cells or T cells modified to express other CARs.

D. Polypeptides

The present invention contemplates, in part, CAR polypeptides and fragments thereof, cells and compositions comprising the same, and vectors that express polypeptides.

In preferred embodiments, a polypeptide comprising one or more CARs as set forth in SEQ ID NO: 9 is provided.

"Polypeptide," "polypeptide fragment," "peptide" and "protein" are used interchangeably, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. In various embodiments, the CAR polypeptides contemplated herein comprise a signal (or leader) sequence at the N-terminal end of the protein, which co-translationally or post-translationally directs transfer of the protein. Illustrative examples of suitable signal sequences useful in CARs disclosed herein include, but are not limited to the IgG1 heavy chain signal sequence and the CD8α signal sequence. Polypeptides can be prepared using any of a variety of well-known recombinant and/or synthetic techniques. Polypeptides contemplated herein specifically encompass the CARs of the present disclosure, or sequences that have deletions from, additions to, and/or substitutions of one or more amino acid of a CAR as disclosed herein.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. Similarly, an "isolated cell" refers to a cell that has been obtained from an in vivo tissue or organ and is substantially free of extracellular matrix.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of the CARs by introducing one or more substitutions, deletions, additions and/or insertions into a binding domain, hinge, TM domain, co-stimulatory signaling domain or primary signaling domain of a CAR polypeptide. Preferably, polypeptides of the invention include polypeptides having at least about 65%, 70%, 75%, 85%, 90%, 95%, 98%, or 99% amino acid identity thereto.

Polypeptides include "polypeptide fragments." Polypeptide fragments refer to a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of a murine anti-BCMA antibody, useful fragments include, but are not limited to: a CDR region, a CDR3 region of the heavy or light chain; a variable region of a heavy or light chain; a portion of an antibody chain or variable region including two CDRs; and the like.

The polypeptide may also be fused in-frame or conjugated to a linker or other sequence for ease of synthesis, purification or identification of the polypeptide (e.g., poly-His), or to enhance binding of the polypeptide to a solid support.

As noted above, polypeptides of the invention may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol*, 154: 367-382), U.S. Pat. No. 4,873,192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (Natl. Biomed. Res. Found., Washington, D.C.).

In certain embodiments, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant polypeptide of the invention, one skilled in the art, for example, can change one or more of the codons of the encoding DNA sequence, e.g., according to Table 1.

TABLE 1

| Amino Acid Codons | | | |
|---|---|---|---|
| Amino Acids | One letter code | Three letter code | Codons |
| Alanine | A | Ala | GCA GCC GCG GCU |
| Cysteine | C | Cys | UGC UGU |
| Aspartic acid | D | Asp | GAC GAU |
| Glutamic acid | E | Glu | GAA GAG |
| Phenylalanine | F | Phe | UUC UUU |
| Glycine | G | Gly | GGA GGC GGG GGU |
| Histidine | H | His | CAC CAU |
| Isoleucine | I | Iso | AUA AUC AUU |
| Lysine | K | Lys | AAA AAG |
| Leucine | L | Leu | UUA UUG CUA CUC CUG CUU |
| Methionine | M | Met | AUG |
| Asparagine | N | Asn | AAC AAU |

TABLE 1-continued

Amino Acid Codons

| Amino Acids | One letter code | Three letter code | Codons |
|---|---|---|---|
| Proline | P | Pro | CCA CCC CCG CCU |
| Glutamine | Q | Gln | CAA CAG |
| Arginine | R | Arg | AGA AGG CGA CGC CGG CGU |
| Serine | S | Ser | AGC AGU UCA UCC UCG UCU |
| Threonine | T | Thr | ACA ACC ACG ACU |
| Valine | V | Val | GUA GUC GUG GUU |
| Tryptophan | W | Trp | UGG |
| Tyrosine | Y | Tyr | UAC UAU |

Guidance in determining which amino acid residues can be substituted, inserted, or deleted without abolishing biological activity can be found using computer programs well known in the art, such as DNASTAR™ software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224). Exemplary conservative substitutions are described in U.S. Provisional Patent Application No. 61/241,647, the disclosure of which is herein incorporated by reference.

In making such changes, the hydropathic index of amino acids may be considered. The importance of the hydropathic amino acid index in conferring interactive biologic function on a protein is generally understood in the art (Kyte and Doolittle, 1982, incorporated herein by reference). Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

Polypeptide variants further include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

In one embodiment, where expression of two or more polypeptides is desired, the polynucleotide sequences encoding them can be separated by and IRES sequence as discussed elsewhere herein. In another embodiment, two or more polypeptides can be expressed as a fusion protein that comprises one or more self-cleaving polypeptide sequences.

Polypeptides of the present invention include fusion polypeptides. In preferred embodiments, fusion polypeptides and polynucleotides encoding fusion polypeptides are provided, e.g., CARs. Fusion polypeptides and fusion proteins refer to a polypeptide having at least two, three, four, five, six, seven, eight, nine, or ten or more polypeptide segments. Fusion polypeptides are typically linked C-terminus to N-terminus, although they can also be linked C-terminus to C-terminus, N-terminus to N-terminus, or N-terminus to C-terminus. The polypeptides of the fusion protein can be in any order or a specified order. Fusion polypeptides or fusion proteins can also include conservatively modified variants, polymorphic variants, alleles, mutants, subsequences, and interspecies homologs, so long as the desired transcriptional activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as discussed elsewhere herein.

In one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments or to facilitate transport of the fusion protein through the cell membrane.

Fusion polypeptides may further comprise a polypeptide cleavage signal between each of the polypeptide domains described herein. In addition, polypeptide site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic*, 5(8); 616-26).

Suitable protease cleavages sites and self-cleaving peptides are known to the skilled person (see, e.g., in Ryan et al., 1997. *J. Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picoma 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO: 23), for example, ENLYFQG (SEQ ID NO: 24) and ENLYFQS (SEQ ID NO: 25), wherein X represents any amino acid (cleavage by TEV occurs between Q and G or Q and S).

In a particular embodiment, self-cleaving peptides include those polypeptide sequences obtained from potyvirus and cardiovirus 2A peptides, FMDV (foot-and-mouth disease virus), equine rhinitis A virus, Thosea asigna virus and porcine teschovirus.

In certain embodiments, the self-cleaving polypeptide site comprises a 2A or 2A-like site, sequence or domain (Donnelly et al., 2001. *J. Gen. Virol.* 82:1027-1041).

TABLE 2

Exemplary 2A sites include the following sequences:

| | |
|---|---|
| SEQ ID NO: 26 | LLNFDLLKLAGDVESNPGP |
| SEQ ID NO: 27 | TLNFDLLKLAGDVESNPGP |
| SEQ ID NO: 28 | LLKLAGDVESNPGP |
| SEQ ID NO: 29 | NFDLLKLAGDVESNPGP |
| SEQ ID NO: 30 | QLLNFDLLKLAGDVESNPGP |
| SEQ ID NO: 31 | APVKQTLNFDLLKLAGDVESNPGP |
| SEQ ID NO: 32 | VTELLYRMKRAETYCPRPLLAIHPTEARHKQKIV APVKQT |
| SEQ ID NO: 33 | LNFDLLKLAGDVESNPGP |
| SEQ ID NO: 34 | LLAIHPTEARHKQKIVAPVKQTLNFDLLKLAGDV ESNPGP |
| SEQ ID NO: 35 | EARHKQKIVAPVKQTLNFDLLKLAGDVESNPGP |

In preferred embodiments, a polypeptide contemplated herein comprises a CAR polypeptide.

E. Polynucleotides

In preferred embodiments, a polynucleotide encoding one or more CAR polypeptides is provided, e.g., SEQ ID NO: 10. As used herein, the terms "polynucleotide" or "nucleic acid" refers to messenger RNA (mRNA), RNA, genomic RNA (gRNA), plus strand RNA (RNA(+)), minus strand RNA (RNA(−)), genomic DNA (gDNA), complementary DNA (cDNA) or recombinant DNA. Polynucleotides include single and double stranded polynucleotides. Preferably, polynucleotides of the invention include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. In various illustrative embodiments, the present invention contemplates, in part, polynucleotides comprising expression vectors, viral vectors, and transfer plasmids, and compositions, and cells comprising the same.

In particular embodiments, polynucleotides are provided by this invention that encode at least about 5, 10, 25, 50, 100, 150, 200, 250, 300, 350, 400, 500, 1000, 1250, 1500, 1750, or 2000 or more contiguous amino acid residues of a polypeptide of the invention, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., Current Protocols in Molecular Biology, John Wiley & Sons Inc, 1994-1998, Chapter 15.

As used herein, "isolated polynucleotide" refers to a polynucleotide that has been purified from the sequences which flank it in a naturally-occurring state, e.g., a DNA fragment that has been removed from the sequences that are normally adjacent to the fragment. An "isolated polynucleotide" also refers to a complementary DNA (cDNA), a recombinant DNA, or other polynucleotide that does not exist in nature and that has been made by the hand of man.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the premessenger (premRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' AG T C AT G 3' is 3' T C AG TA C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

Moreover, it will be appreciated by those of ordinary skill in the art that, as a result of the degeneracy of the genetic code, there are many nucleotide sequences that encode a polypeptide, or fragment of variant thereof, as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein may also be used. Alleles are endogenous genes that are altered as a result of one or more mutations, such as deletions, additions and/or substitutions of nucleotides.

The term "nucleic acid cassette" as used herein refers to genetic sequences within a vector which can express a RNA, and subsequently a protein. The nucleic acid cassette contains the gene of interest, e.g., a CAR. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment of the invention, the nucleic acid cassette contains the sequence of a chimeric antigen receptor used to treat a B cell malignancy. The cassette can be removed and inserted into a plasmid or viral vector as a single unit.

In particular embodiments, polynucleotides include at least one polynucleotide-of-interest. As used herein, the term "polynucleotide-of-interest" refers to a polynucleotide encoding a polypeptide (i.e., a polypeptide-of-interest), inserted into an expression vector that is desired to be expressed. A vector may comprise 1, 2, 3, 4, 5, 6, 7, 8, 9, or 10 polynucleotides-of-interest. In certain embodiments, the polynucleotide-of-interest encodes a polypeptide that provides a therapeutic effect in the treatment or prevention of a disease or disorder. Polynucleotides-of-interest, and polypeptides encoded therefrom, include both polynucleotides that encode wild-type polypeptides, as well as functional variants and fragments thereof. In particular embodiments, a functional variant has at least 80%, at least 90%, at least 95%, or at least 99% identity to a corresponding wild-type reference polynucleotide or polypeptide sequence. In certain embodiments, a functional variant or fragment has at least 50%, at least 60%, at least 70%, at least 80%, or at least 90% of a biological activity of a corresponding wild-type polypeptide.

In one embodiment, the polynucleotide-of-interest does not encode a polypeptide but serves as a template to transcribe miRNA, siRNA, or shRNA, ribozyme, or other inhibitory RNA. In various other embodiments, a polynucleotide comprises a polynucleotide-of-interest encoding a CAR and one or more additional polynucleotides-of-interest including but not limited to an inhibitory nucleic acid sequence including, but not limited to: an siRNA, an miRNA, an shRNA, and a ribozyme.

As used herein, the terms "siRNA" or "short interfering RNA" refer to a short polynucleotide sequence that mediates a process of sequence-specific post-transcriptional gene silencing, translational inhibition, transcriptional inhibition, or epigenetic RNAi in animals (Zamore et al., 2000, Cell, 101, 25-33; Fire et al., 1998, Nature, 391, 806; Hamilton et al., 1999, Science, 286, 950-951; Lin et al., 1999, Nature, 402, 128-129; Sharp, 1999, Genes & Dev., 13, 139-141; and Strauss, 1999, Science, 286, 886). In certain embodiments, an siRNA comprises a first strand and a second strand that have the same number of nucleosides; however, the first and second strands are offset such that the two terminal nucleosides on the first and second strands are not paired with a residue on the complimentary strand. In certain instances, the two nucleosides that are not paired are thymidine resides. The siRNA should include a region of sufficient homology to the target gene, and be of sufficient length in terms of nucleotides, such that the siRNA, or a fragment thereof, can mediate down regulation of the target gene. Thus, an siRNA includes a region which is at least partially complementary to the target RNA. It is not necessary that there be perfect complementarity between the siRNA and the target, but the correspondence must be sufficient to enable the siRNA, or a cleavage product thereof, to direct sequence specific silencing, such as by RNAi cleavage of the target RNA. Complementarity, or degree of homology with the target strand, is most critical in the antisense strand. While perfect complementarity, particularly in the antisense strand, is often desired, some embodiments include one or more, but preferably 10, 8, 6, 5, 4, 3, 2, or fewer mismatches with respect to the target RNA. The mismatches are most tolerated in the terminal regions, and if present are preferably in a terminal region or regions, e.g., within 6, 5, 4, or 3 nucleotides of the 5' and/or 3' terminus. The sense strand need only be sufficiently complementary with the antisense strand to maintain the overall double-strand character of the molecule.

In addition, an siRNA may be modified or include nucleoside analogs. Single stranded regions of an siRNA may be modified or include nucleoside analogs, e.g., the unpaired region or regions of a hairpin structure, e.g., a region which links two complementary regions, can have modifications or nucleoside analogs. Modification to stabilize one or more 3'- or 5'-terminus of an siRNA, e.g., against exonucleases, or to favor the antisense siRNA agent to enter into RISC are also useful. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis. Each strand of an siRNA can be equal to or less than 30, 25, 24, 23, 22, 21, or 20 nucleotides in length. The strand is preferably at least 19 nucleotides in length. For example, each strand can be between 21 and 25 nucleotides in length. Preferred siRNAs have a duplex region of 17, 18, 19, 29, 21, 22, 23, 24, or 25 nucleotide pairs, and one or more overhangs of 2-3 nucleotides, preferably one or two 3' overhangs, of 2-3 nucleotides.

As used herein, the terms "miRNA" or "microRNA" refer to small non-coding RNAs of 20-22 nucleotides, typically excised from ~70 nucleotide fold-back RNA precursor structures known as pre-miRNAs. miRNAs negatively regulate their targets in one of two ways depending on the degree of complementarity between the miRNA and the target. First, miRNAs that bind with perfect or nearly perfect complementarity to protein-coding mRNA sequences induce the RNA-mediated interference (RNAi) pathway. miRNAs that exert their regulatory effects by binding to imperfect complementary sites within the 3' untranslated regions (UTRs) of their mRNA targets, repress target-gene expression post-transcriptionally, apparently at the level of translation, through a RISC complex that is similar to, or possibly identical with, the one that is used for the RNAi pathway. Consistent with translational control, miRNAs that use this mechanism reduce the protein levels of their target genes, but the mRNA levels of these genes are only minimally affected. miRNAs encompass both naturally occurring miRNAs as well as artificially designed miRNAs that can specifically target any mRNA sequence. For example, in one embodiment, the skilled artisan can design short hairpin RNA constructs expressed as human miRNA (e.g., miR-30 or miR-21) primary transcripts. This design adds a Drosha processing site to the hairpin construct and has been shown to greatly increase knockdown efficiency (Pusch et al., 2004). The hairpin stem consists of 22-nt of dsRNA (e.g., antisense has perfect complementarity to desired target) and a 15-19-nt loop from a human miR. Adding the miR loop and miR30 flanking sequences on either or both sides of the hairpin results in greater than 10-fold increase in Drosha and Dicer processing of the expressed hairpins when compared with conventional shRNA designs without microRNA. Increased Drosha and Dicer processing translates into greater siRNA/miRNA production and greater potency for expressed hairpins.

As used herein, the terms "shRNA" or "short hairpin RNA" refer to double-stranded structure that is formed by a single self-complementary RNA strand. shRNA constructs containing a nucleotide sequence identical to a portion, of either coding or non-coding sequence, of the target gene are preferred for inhibition. RNA sequences with insertions, deletions, and single point mutations relative to the target sequence have also been found to be effective for inhibition. Greater than 90% sequence identity, or even 100% sequence identity, between the inhibitory RNA and the portion of the target gene is preferred. In certain preferred embodiments, the length of the duplex-forming portion of an shRNA is at least 20, 21 or 22 nucleotides in length, e.g., corresponding in size to RNA products produced by Dicer-dependent cleavage. In certain embodiments, the shRNA construct is at least 25, 50, 100, 200, 300 or 400 bases in length. In certain embodiments, the shRNA construct is 400-800 bases in length. shRNA constructs are highly tolerant of variation in loop sequence and loop size.

As used herein, the term "ribozyme" refers to a catalytically active RNA molecule capable of site-specific cleavage of target mRNA. Several subtypes have been described, e.g., hammerhead and hairpin ribozymes. Ribozyme catalytic activity and stability can be improved by substituting deoxyribonucleotides for ribonucleotides at noncatalytic bases. While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA has the following sequence of two bases: 5'-UG-3'. The construction and production of hammerhead ribozymes is well known in the art.

A preferred method of delivery of a polynucleotide-of-interest that comprises an siRNA, an miRNA, an shRNA, or a ribozyme comprises one or more regulatory sequences, such as, for example, a strong constitutive pol III, e.g., human U6 snRNA promoter, the mouse U6 snRNA promoter, the human and mouse H1 RNA promoter and the human tRNA-val promoter, or a strong constitutive pol II promoter, as described elsewhere herein.

The polynucleotides of the present invention, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

Polynucleotides can be prepared, manipulated and/or expressed using any of a variety of well-established techniques known and available in the art. In order to express a desired polypeptide, a nucleotide sequence encoding the polypeptide, can be inserted into appropriate vector. Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, he coding sequences of the chimeric proteins disclosed herein can be ligated into such expression vectors for the expression of the chimeric protein in mammalian cells.

In one embodiment, a vector encoding a CAR contemplated herein comprises the polynucleotide sequence set forth in SEQ ID NO: 36.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally. The vector is engineered to harbor the sequence coding for the origin of DNA replication or "ori" from a lymphotrophic herpes virus or a gamma herpesvirus, an adenovirus, SV40, a bovine papilloma virus, or a yeast, specifically a replication origin of a lymphotrophic herpes virus or a gamma herpesvirus corresponding to oriP of EBV. In a particular aspect, the lymphotrophic herpes virus may be Epstein Barr virus (EBV), Kaposi's sarcoma herpes virus (KSHV), Herpes virus saimiri (HS), or Marek's disease virus (MDV). Epstein Barr virus (EBV) and Kaposi's sarcoma herpes virus (KSHV) are also examples of a gamma herpesvirus. Typically, the host cell comprises the viral replication transactivator protein that activates the replication.

The "control elements" or "regulatory sequences" present in an expression vector are those non-translated regions of the vector-origin of replication, selection cassettes, promoters, enhancers, translation initiation signals (Shine Dalgarno sequence or Kozak sequence) introns, a polyadenylation sequence, 5' and 3' untranslated regions-which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a vector for use in practicing the invention including, but not limited to expression vectors and viral vectors, will include exogenous, endogenous, or heterologous control sequences such as promoters and/or enhancers. An "endogenous" control sequence is one which is naturally linked with a given gene in the genome. An "exogenous" control sequence is one which is placed in juxtaposition to a gene by means of genetic manipulation (i.e., molecular biological techniques) such that transcription of that gene is directed by the linked enhancer/promoter. A "heterologous" control sequence is an exogenous sequence that is from a different species than the cell being genetically manipulated.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments of the invention include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter (Challita et al., *J Virol.* 69(2):748-55 (1995)).

In one embodiment, a vector of the invention comprises a MND promoter.

In one embodiment, a vector of the invention comprises an EF1a promoter comprising the first intron of the human EF1a gene.

In one embodiment, a vector of the invention comprises an EF1a promoter that lacks the first intron of the human EF1a gene.

In a particular embodiment, it may be desirable to express a polynucleotide comprising a CAR from a T cell specific promoter.

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments of the invention provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene*, 323:67), the cumate inducible gene switch (WO 2002/088346), tetracycline-dependent regulatory systems, etc.

Conditional expression can also be achieved by using a site specific DNA recombinase. According to certain embodiments of the invention the vector comprises at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments of the present invention include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The vectors may comprise one or more recombination sites for any of a wide variety of site specific recombinases. It is to be understood that the target site for a site specific recombinase is in addition to any site(s) required for integration of a vector, e.g., a retroviral vector or lentiviral vector. As used herein, the terms "recombination sequence," "recombination site," or "site specific recombination site" refer to a particular nucleic acid sequence to which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (see FIG. 1 of Sauer, B., *Current Opinion in Biotechnology* 5:521-527 (1994)). Other exemplary loxP sites include, but are not limited to: lox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995).

Suitable recognition sites for the FLP recombinase include, but are not limited to: FRT (McLeod, et al., 1996), $F_1$, $F_2$, $F_3$ (Schlake and Bode, 1994), $F_4$, $F_5$ (Schlake and Bode, 1994), FRT(LE) (Senecoff et al., 1988), FRT(RE) (Senecoff et al., 1988).

Other examples of recognition sequences are the attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagarajan et al., 2001; Belteki et al., 2003). Thus, typical strategies position by homologous recombination an attP-bearing "docking site" into a defined locus, which is then partnered with an attB-bearing incoming sequence for insertion.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. In particular embodiments, the vectors contemplated by the invention, include one or more polynucleotides-of-interest that encode one or more polypeptides. In particular embodiments, to achieve efficient translation of each of the plurality of polypeptides, the polynucleotide sequences can be separated by one or more IRES sequences or polynucleotide sequences encoding self-cleaving polypeptides.

As used herein, the term "Kozak sequence" refers to a short nucleotide sequence that greatly facilitates the initial binding of mRNA to the small subunit of the ribosome and increases translation. The consensus Kozak sequence is (GCC)RCCATGG, where R is a purine (A or G) (Kozak, 1986. *Cell.* 44(2):283-92, and Kozak, 1987. *Nucleic Acids Res.* 15(20):8125-48). In particular embodiments, the vectors contemplated by the invention, comprise polynucleotides that have a consensus Kozak sequence and that encode a desired polypeptide, e.g., a CAR.

In some embodiments of the invention, a polynucleotide or cell harboring the polynucleotide utilizes a suicide gene, including an inducible suicide gene to reduce the risk of direct toxicity and/or uncontrolled proliferation. In specific aspects, the suicide gene is not immunogenic to the host harboring the polynucleotide or cell. A certain example of a suicide gene that may be used is caspase-9 or caspase-8 or cytosine deaminase. Caspase-9 can be activated using a specific chemical inducer of dimerization (CID).

In certain embodiments, vectors comprise gene segments that cause the immune effector cells of the invention, e.g., T cells, to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene (Wigler et al., Cell 11:223, 1977) which confers ganciclovir sensitivity; the cellular hypoxanthine phosphribosyltransferase (HPRT) gene, the cellular adenine phosphoribosyltransferase (APRT) gene, and bacterial cytosine deaminase, (Mullen et al., Proc. Natl. Acad. Sci. USA. 89:33 (1992)).

In some embodiments, genetically modified immune effector cells, such as T cells, comprise a polynucleotide further comprising a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

Preferably, the positive selectable marker and the negative selectable element are linked such that loss of the negative selectable element necessarily also is accompanied by loss of the positive selectable marker. Even more preferably, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See Lupton S. D., et al, Mol. and Cell. Biology 1 1:3374-3378, 1991. In addition, in preferred embodiments, the polynucleotides of the invention encoding the chimeric receptors are in retroviral vectors containing the fused gene, particularly those that confer hygromycin B resistance for positive selection in vitro, and ganciclovir sensitivity for negative selection in vivo, for example the HyTK retroviral vector described in Lupton, S. D. et al. (1991), supra. See also the publications of PCT US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, nco, and gpt, and preferred negative selectable markers are derived from genes selected from the group consisting of cytosine deaminase, HSV-I TK, VZV TK, HPRT, APRT and gpt. Especially preferred markers are bifunctional selectable fusion genes wherein the positive selectable marker is derived from hph or neo, and the negative selectable marker is derived from cytosine deaminase or a TK gene or selectable marker. Inducible Suicide Genes F. Viral Vectors In particular embodiments, a cell (e.g., an immune effector cell) is transduced with a retroviral vector, e.g., a lentiviral vector, encoding a CAR. For example, an immune effector cell is transduced with a vector encoding a CAR that comprises a murine anti-BCMA antibody or antigen binding fragment thereof that binds a BCMA polypeptide, with an intracellular signaling domain of CD3ζ, CD28, 4-1BB, Ox40, or any combinations thereof. Thus, these transduced cells can elicit a CAR-mediated cytotoxic response.

Retroviruses are a common tool for gene delivery (Miller, 2000, *Nature.* 357: 455-460). In particular embodiments, a retrovirus is used to deliver a polynucleotide encoding a chimeric antigen receptor (CAR) to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred. In particular embodiments, a lentivirus is used to deliver a polynucleotide comprising a CAR to a cell.

Retroviral vectors and more particularly lentiviral vectors may be used in practicing particular embodiments of the present invention. Accordingly, the term "retrovirus" or "retroviral vector", as used herein is meant to include "lentivirus" and "lentiviral vectors" respectively.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus. The term "hybrid vector" refers to a vector, LTR or other nucleic acid containing both retroviral, e.g., lentiviral, sequences and non-lentiviral viral sequences. In one embodiment, a hybrid vector refers to a vector or transfer plasmid comprising retroviral e.g., lentiviral, sequences for reverse transcription, replication, integration and/or packaging.

In particular embodiments, the terms "lentiviral vector," "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the invention and are present in DNA form in the DNA plasmids of the invention.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R and U5 regions and appears at both the 5' and 3' ends of the viral genome. Adjacent to the 5' LTR are sequences necessary for reverse transcription of the genome (the tRNA primer binding site) and for efficient packaging of viral RNA into particles (the Psi site).

As used herein, the term "packaging signal" or "packaging sequence" refers to sequences located within the retroviral genome which are required for insertion of the viral RNA into the viral capsid or particle, see e.g., Clever et al., 1995. *J. of Virology*, Vol. 69, No. 4; pp. 2101-2109. Several retroviral vectors use the minimal packaging signal (also referred to as the psi [Ψ] sequence) needed for encapsidation of the viral genome. Thus, as used herein, the terms "packaging sequence," "packaging signal," "psi" and the symbol "Ψ," are used in reference to the non-coding sequence required for encapsidation of retroviral RNA strands during viral particle formation.

In various embodiments, vectors comprise modified 5' LTR and/or 3' LTRs. Either or both of the LTR may comprise one or more modifications including, but not limited to, one or more deletions, insertions, or substitutions. Modifications of the 3' LTR are often made to improve the safety of lentiviral or retroviral systems by rendering viruses replication-defective. As used herein, the term "replication-defective" refers to virus that is not capable of complete, effective replication such that infective virions are not produced (e.g., replication-defective lentiviral progeny). The term "replication-competent" refers to wild-type virus or mutant virus that is capable of replication, such that viral replication of the virus is capable of producing infective virions (e.g., replication-competent lentiviral progeny).

"Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. This is because the right (3') LTR U3 region is used as a template for the left (5') LTR U3 region during viral replication and, thus, the viral transcript cannot be made without the U3 enhancer-promoter. In a further embodiment of the invention, the 3' LTR is modified such that the U5 region is replaced, for example, with an ideal poly(A) sequence. It should be noted that modifications to the LTRs such as modifications to the 3' LTR, the 5' LTR, or both 3' and 5' LTRs, are also included in the invention.

An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In certain embodiments, the heterologous promoter has additional advantages in controlling the manner in which the viral genome is transcribed. For example, the heterologous promoter can be inducible, such that transcription of all or part of the viral genome will occur only when the induction factors are present. Induction factors include, but are not limited to, one or more chemical compounds or the physiological conditions such as temperature or pH, in which the host cells are cultured.

In some embodiments, viral vectors comprise a TAR element. The term "TAR" refers to the "trans-activation response" genetic element located in the R region of lentiviral (e.g., HIV) LTRs. This element interacts with the lentiviral trans-activator (tat) genetic element to enhance viral replication. However, this element is not required in embodiments wherein the U3 region of the 5' LTR is replaced by a heterologous promoter.

The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

As used herein, the term "FLAP element" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, Cell, 101:173. During HIV-1 reverse transcription, central initiation of the plus-strand DNA at the central polypurine tract (cPPT) and central termination at the central termination sequence (CTS) lead to the formation of a three-stranded DNA structure: the HIV-1 central DNA flap. While not wishing to be bound by any theory, the DNA flap may act as a cis-active determinant of lentiviral genome nuclear import and/or may increase the titer of the virus. In particular embodiments, the retroviral or lentiviral vector backbones comprise one or more FLAP elements upstream or downstream of the heterologous genes of interest in the vectors. For example, in particular embodiments a transfer plasmid includes a FLAP element. In one embodiment, a vector of the invention comprises a FLAP element isolated from HIV-1.

In one embodiment, retroviral or lentiviral transfer vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. J. Virol. 65: 1053; and Cullen et al., 1991. Cell 58: 423), and the hepatitis B virus post-transcriptional regulatory element (HPRE). Generally, the RNA export element is placed within the 3' UTR of a gene, and can be inserted as one or multiple copies.

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, J. Virol., 73:2886); the posttranscriptional regulatory element present in hepatitis B virus (HPRE) (Huang et al., Mol. Cell. Biol., 5:3864); and the like (Liu et al., 1995, Genes Dev., 9:1766). In particular embodiments, vectors of the invention comprise a posttranscriptional regulatory element such as a WPRE or HPRE In particular embodiments, vectors of the invention lack or do not comprise a posttranscriptional regulatory element (PTE) such as a WPRE or HPRE because in some instances these elements increase the risk of cellular transformation and/or do not substantially or significantly increase the amount of mRNA transcript or increase mRNA stability. Therefore, in some embodiments, vectors of the invention lack or do not comprise a PTE. In other embodiments, vectors of the invention lack or do not comprise a WPRE or HPRE as an added safety measure.

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Efficient polyadenylation of the recombinant transcript is desirable as transcripts lacking a poly A tail are unstable and are rapidly degraded. Illustrative examples of polyA signals that can be used in a vector of the invention, includes an ideal polyA sequence (e.g., AATAAA, ATTAAA, AGTAAA), a bovine growth hormone polyA sequence (BGHpA), a rabbit β-globin polyA sequence (rβgpA), or another suitable heterologous or endogenous polyA sequence known in the art.

In certain embodiments, a retroviral or lentiviral vector further comprises one or more insulator elements. Insulators elements may contribute to protecting lentivirus-expressed sequences, e.g., therapeutic polypeptides, from integration site effects, which may be mediated by cis-acting elements present in genomic DNA and lead to deregulated expression of transferred sequences (i.e., position effect; see, e.g., Burgess-Beusse et al., 2002, Proc. Natl. Acad. Sci., USA, 99:16433; and Zhan et al., 2001, Hum. Genet., 109:471). In some embodiments, transfer vectors comprise one or more insulator element the 3' LTR and upon integration of the provirus into the host genome, the provirus comprises the one or more insulators at both the 5' LTR or 3' LTR, by virtue of duplicating the 3' LTR. Suitable insulators for use in the invention include, but are not limited to, the chicken β-globin insulator (see Chung et al., 1993. Cell 74:505; Chung et al., 1997. PNAS 94:575; and Bell et al., 1999. Cell 98:387, incorporated by reference herein). Examples of insulator elements include, but are not limited to, an insulator from an β-globin locus, such as chicken HS4.

According to certain specific embodiments of the invention, most or all of the viral vector backbone sequences are derived from a lentivirus, e.g., HIV-1. However, it is to be understood that many different sources of retroviral and/or lentiviral sequences can be used, or combined and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid of the present invention.

In various embodiments, the vectors of the invention comprise a promoter operably linked to a polynucleotide encoding a CAR polypeptide. The vectors may have one or more LTRs, wherein either LTR comprises one or more modifications, such as one or more nucleotide substitutions, additions, or deletions. The vectors may further comprise one of more accessory elements to increase transduction efficiency (e.g., a cPPT/FLAP), viral packaging (e.g., a Psi (Ψ) packaging signal, RRE), and/or other elements that increase therapeutic gene expression (e.g., poly (A) sequences), and may optionally comprise a WPRE or HPRE.

In a particular embodiment, the transfer vector of the invention comprises a left (5') retroviral LTR; a central polypurine tract/DNA flap (cPPT/FLAP); a retroviral export element; a promoter active in a T cell, operably linked to a polynucleotide encoding CAR polypeptide contemplated herein; and a right (3') retroviral LTR; and optionally a WPRE or HPRE.

In a particular embodiment, the transfer vector of the invention comprises a left (5') retroviral LTR; a retroviral export element; a promoter active in a T cell, operably linked to a polynucleotide encoding CAR polypeptide contemplated herein; a right (3') retroviral LTR; and a poly (A) sequence; and optionally a WPRE or HPRE. In another particular embodiment, the invention provides a lentiviral vector comprising: a left (5') LTR; a cPPT/FLAP; an RRE; a promoter active in a T cell, operably linked to a polynucleotide encoding CAR polypeptide contemplated herein; a right (3') LTR; and a polyadenylation sequence; and optionally a WPRE or HPRE.

In a certain embodiment, the invention provides a lentiviral vector comprising: a left (5') HIV-1 LTR; a Psi (Ψ) packaging signal; a cPPT/FLAP; an RRE; a promoter active in a T cell, operably linked to a polynucleotide encoding CAR polypeptide contemplated herein; a right (3') self-inactivating (SIN) HIV-1 LTR; and a rabbit β-globin polyadenylation sequence; and optionally a WPRE or HPRE.

In another embodiment, the invention provides a vector comprising: at least one LTR; a central polypurine tract/DNA flap (cPPT/FLAP); a retroviral export element; and a promoter active in a T cell, operably linked to a polynucleotide encoding CAR polypeptide contemplated herein; and optionally a WPRE or HPRE.

In particular embodiment, the present invention provides a vector comprising at least one LTR; a cPPT/FLAP; an RRE; a promoter active in a T cell, operably linked to a polynucleotide encoding CAR polypeptide contemplated herein; and a polyadenylation sequence; and optionally a WPRE or HPRE.

In a certain embodiment, the present invention provides at least one SIN HIV-1 LTR; a Psi (Ψ) packaging signal; a cPPT/FLAP; an RRE; a promoter active in a T cell, operably linked to a polynucleotide encoding CAR polypeptide contemplated herein; and a rabbit β-globin polyadenylation sequence; and optionally a WPRE or HPRE.

In various embodiments, the vector is an integrating viral vector.

In various other embodiments, the vector is an episomal or non-integrating viral vector.

In various embodiments, vectors contemplated herein, comprise non-integrating or integration defective retrovirus. In one embodiment, an "integration defective" retrovirus or lentivirus refers to retrovirus or lentivirus having an integrase that lacks the capacity to integrate the viral genome into the genome of the host cells. In various embodiments, the integrase protein is mutated to specifically decrease its integrase activity. Integration-incompetent lentiviral vectors are obtained by modifying the pol gene encoding the integrase protein, resulting in a mutated pol gene encoding an integrative deficient integrase. Such integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81 R, D41A, K42A, H51A, Q53C, D55V, D64E, D64V, E69A, K71A, E85A, E87A, D116N, D116I, D116A, N120G, N120I, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221L, W235F, W235E, K236S, K236A, K246A, G247W, D253A, R262A, R263A and K264H.

Illustrative mutations in the HIV-1 pol gene suitable to reduce integrase activity include, but are not limited to: D64E, D64V, E92K, D116N, D116I, D116A, N120G, N120I, N120E, E152G, E152A, D35E, K156E, K156A, E157A, K159E, K159A, W235F, and W235E.

In a particular embodiment, an integrase comprises a mutation in one or more of amino acids, D64, D116 or E152. In one embodiment, an integrase comprises a mutation in the amino acids, D64, D116 and E152. In a particular embodiment, a defective HIV-1 integrase comprises a D64V mutation.

A "host cell" includes cells electroporated, transfected, infected, or transduced in vivo, ex vivo, or in vitro with a recombinant vector or a polynucleotide of the invention. Host cells may include packaging cells, producer cells, and cells infected with viral vectors. In particular embodiments, host cells infected with viral vector of the invention are administered to a subject in need of therapy. In certain embodiments, the term "target cell" is used interchangeably with host cell and refers to transfected, infected, or transduced cells of a desired cell type. In preferred embodiments, the target cell is a T cell.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are well known by those of skill in the art. A retroviral/lentiviral transfer vector of the present invention can be introduced into a packaging cell line, via transfection, transduction or infection, to generate a producer cell or cell line. The packaging vectors of the present invention can be introduced into human cells or cell lines by standard methods including, e.g., calcium phosphate transfection, lipofection or electroporation. In some embodiments, the packaging vectors are introduced into the cells together with a dominant selectable marker, such as neomycin, hygromycin, puromycin, blastocidin, zeocin, thymidine kinase, DHFR, Gln synthetase or ADA, followed by selection in the presence of the appropriate drug and isolation of clones. A selectable marker gene can be linked physically to genes encoding by the packaging vector, e.g., by IRES or self-cleaving viral peptides.

Viral envelope proteins (env) determine the range of host cells which can ultimately be infected and transformed by recombinant retroviruses generated from the cell lines. In the case of lentiviruses, such as HIV-1, HIV-2, SIV, FIV and EIV, the env proteins include gp41 and gp120. Preferably, the viral env proteins expressed by packaging cells of the invention are encoded on a separate vector from the viral gag and pol genes, as has been previously described.

Illustrative examples of retroviral-derived env genes which can be employed in the invention include, but are not limited to: MLV envelopes, 10A1 envelope, BAEV, FeLV-B, RD114, SSAV, Ebola, Sendai, FPV (Fowl plague virus), and influenza virus envelopes. Similarly, genes encoding envelopes from RNA viruses (e.g., RNA virus families of Picornaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Bimaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BLV, EBV, CAEV, SNV, ChTLV, STLV, MPMV, SMRV, RAV, FuSV, MH2, AEV, AMV, CT10, and EIAV.

In other embodiments, envelope proteins for pseudotyping a virus of present invention include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpesviruses such as Herpes simplex virus types 1 and 2, varicella zoster, cytomegalovirus, Epstein-Bar virus (EBV), human herpesviruses (HHV), human herpesvirus type 6 and 8, Human immunodeficiency virus (HIV), papilloma virus, murine gammaherpesvirus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, any encephaliltis causing virus.

In one embodiment, the invention provides packaging cells which produce recombinant retrovirus, e.g., lentivirus, pseudotyped with the VSV-G glycoprotein.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to CD4+ presenting cells. In a preferred embodiment of the invention, lentiviral envelope proteins are pseudotyped with VSV-G. In one embodiment, the invention provides packaging cells which produce recombinant retrovirus, e.g., lentivirus, pseudotyped with the VSV-G envelope glycoprotein.

As used herein, the term "packaging cell lines" is used in reference to cell lines that do not contain a packaging signal, but do stably or transiently express viral structural proteins and replication enzymes (e.g., gag, pol and env) which are necessary for the correct packaging of viral particles. Any suitable cell line can be employed to prepare packaging cells of the invention. Generally, the cells are mammalian cells. In a particular embodiment, the cells used to produce the packaging cell line are human cells. Suitable cell lines which can be used include, for example, CHO cells, BHK cells, MDCK cells, C3H 10T1/2 cells, FLY cells, Psi-2 cells, BOSC 23 cells, PA317 cells, WEHI cells, COS cells, BSC 1 cells, BSC 40 cells, BMT 10 cells, VERO cells, W138 cells, MRC5 cells, A549 cells, HT1080 cells, 293 cells, 293T cells, B-50 cells, 3T3 cells, NIH3T3 cells, HepG2 cells, Saos-2 cells, Huh7 cells, HeLa cells, W163 cells, 211 cells, and 211A cells. In preferred embodiments, the packaging cells are 293 cells, 293T cells, or A549 cells. In another preferred embodiment, the cells are A549 cells.

As used herein, the term "producer cell line" refers to a cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J. Virol.* 66:5110-5113. Infectious virus particles may be collected from the packaging cells using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

The delivery of a gene(s) or other polynucleotide sequence using a retroviral or lentiviral vector by means of viral infection rather than by transfection is referred to as "transduction." In one embodiment, retroviral vectors are transduced into a cell through infection and provirus integration. In certain embodiments, a target cell, e.g., a T cell, is "transduced" if it comprises a gene or other polynucleotide sequence delivered to the cell by infection using a viral or retroviral vector. In particular embodiments, a transduced cell comprises one or more genes or other polynucleotide sequences delivered by a retroviral or lentiviral vector in its cellular genome.

In particular embodiments, host cells transduced with viral vector of the invention that expresses one or more polypeptides, are administered to a subject to treat and/or prevent a B cell malignancy. Other methods relating to the use of viral vectors in gene therapy, which may be utilized according to certain embodiments of the present invention, can be found in, e.g., Kay, M. A. (1997) *Chest* 111(6 Supp.):138S-142S; Ferry, N. and Heard, J. M. (1998) *Hum. Gene Ther.* 9:1975-81; Shiratory, Y. et al. (1999) Liver 19:265-74; Oka, K. et al. (2000) *Curr. Opin. Lipidol.* 11:179-86; Thule, P. M. and Liu, J. M. (2000) *Gene Ther.* 7:1744-52; Yang, N. S. (1992) *Crit. Rev. Biotechnol.* 12:335-56; Alt, M. (1995) *J. Hepatol.* 23:746-58; Brody, S. L. and Crystal, R. G. (1994) *Ann. N.Y. Acad. Sci.* 716:90-101; Strayer, D. S. (1999) *Expert Opin. Investig. Drugs* 8:2159-2172; Smith-Arica, J. R. and Bartlett, J. S. (2001) *Curr. Cardiol. Rep.* 3:43-49; and Lee, H. C. et al. (2000) *Nature* 408:483-8.

G. Genetically Modified Cells The present invention contemplates, in particular embodiments, cells genetically modified to express the CARs contemplated herein, for use in the treatment of B cell related conditions. As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably. As used herein, the term "gene therapy" refers to the introduction of extra genetic material in the form of DNA or RNA into the total genetic material in a cell that restores, corrects, or modifies expression of a gene, or for the purpose of expressing a therapeutic polypeptide, e.g., a CAR.

In particular embodiments, the CARs contemplated herein are introduced and expressed in immune effector cells so as to redirect their specificity to a target antigen of interest, e.g., a BCMA polypeptide. An "immune effector cell," is any cell of the immune system that has one or more effector functions (e.g., cytotoxic cell killing activity, secretion of cytokines, induction of ADCC and/or CDC).

Immune effector cells of the invention can be autologous/autogeneic ("self") or non-autologous ("non-self," e.g., allogeneic, syngeneic or xenogeneic).

"Autologous," as used herein, refers to cells from the same subject.

"Allogeneic," as used herein, refers to cells of the same species that differ genetically to the cell in comparison.

"Syngeneic," as used herein, refers to cells of a different subject that are genetically identical to the cell in comparison.

"Xenogeneic," as used herein, refers to cells of a different species to the cell in comparison. In preferred embodiments, the cells of the invention are allogeneic.

Illustrative immune effector cells used with the CARs contemplated herein include T lymphocytes. The terms "T cell" or "T lymphocyte" are art-recognized and are intended to include thymocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; $CD4^+$ T cell) $CD4^+$ T cell, a cytotoxic T cell (CTL; $CD8^+$ T cell), $CD4^+CD8^+$ T cell, $CD4^-CD8^-$ T cell, or any other subset of T cells. Other illustrative populations of T cells suitable for use in particular embodiments include naïve T cells and memory T cells.

As would be understood by the skilled person, other cells may also be used as immune effector cells with the CARs as described herein. In particular, immune effector cells also include NK cells, NKT cells, neutrophils, and macrophages. Immune effector cells also include progenitors of effector cells wherein such progenitor cells can be induced to differentiate into an immune effector cells in vivo or in vitro. Thus, in particular embodiments, immune effector cell includes progenitors of immune effectors cells such as hematopoietic stem cells (HSCs) contained within the CD34+ population of cells derived from cord blood, bone marrow or mobilized peripheral blood which upon administration in a subject differentiate into mature immune effector cells, or which can be induced in vitro to differentiate into mature immune effector cells.

As used herein, immune effector cells genetically engineered to contain BCMA-specific CAR may be referred to as, "BCMA-specific redirected immune effector cells."

The term, "CD34+ cell," as used herein refers to a cell expressing the CD34 protein on its cell surface. "CD34," as used herein refers to a cell surface glycoprotein (e.g., sialomucin protein) that often acts as a cell-cell adhesion factor and is involved in T cell entrance into lymph nodes. The CD34+ cell population contains hematopoietic stem cells (HSC), which upon administration to a patient differentiate and contribute to all hematopoietic lineages, including T cells, NK cells, NKT cells, neutrophils and cells of the monocyte/macrophage lineage.

The present invention provides methods for making the immune effector cells which express the CAR contemplated herein. In one embodiment, the method comprises transfecting or transducing immune effector cells isolated from an individual such that the immune effector cells express one or more CAR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a CAR. In this regard, the immune effector cells may be cultured before and/or after being genetically modified (i.e., transduced or transfected to express a CAR contemplated herein).

In particular embodiments, prior to in vitro manipulation or genetic modification of the immune effector cells described herein, the source of cells is obtained from a subject. In particular embodiments, the CAR-modified immune effector cells comprise T cells. T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation. In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. As would be appreciated by those of ordinary skill in the art, a washing step may be accomplished by methods known to those in the art, such as by using a semiautomated flowthrough centrifuge. For example, the Cobe 2991 cell processor, the Baxter CytoMate, or the like. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells, expressing one or more of the following markers: CD3, CD28, CD4, CD8, CD45RA, and CD45RO, can be further isolated by positive or negative selection techniques. In one embodiment, a specific subpopulation of T cells, expressing CD3, CD28, CD4, CD8, CD45RA, and CD45RO is further isolated by positive or negative selection techniques. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD1 b, CD16, HLA-DR, and CD8. Flow cytometry and cell sorting may also be used to isolate cell populations of interest for use in the present invention.

PBMC may be directly genetically modified to express CARs using methods contemplated herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion.

CD8+ cells can be obtained by using standard methods. In some embodiments, CD8+ cells are further sorted into naïve, central memory, and effector cells by identifying cell surface antigens that are associated with each of those types of CD8+ cells.

In certain embodiments, naive CD8+ T lymphocytes are characterized by the expression of phenotypic markers of naive T cells including CD62L, CCR7, CD28, CD3, CD127, and CD45RA.

In particular embodiments, memory T cells are present in both CD62L+ and CD62L− subsets of CD8+ peripheral blood lymphocytes. PBMC are sorted into CD62L-CD8+ and CD62L+CD8+ fractions after staining with anti-CD8 and anti-CD62L antibodies. In some embodiments, the expression of phenotypic markers of central memory T cells include CD45RO, CD62L, CCR7, CD28, CD3, and CD127 and are negative for granzyme B. In some embodiments, central memory T cells are CD45RO+, CD62L+, CD8+ T cells.

In some embodiments, effector T cells are negative for CD62L, CCR7, CD28, and CD127, and positive for granzyme B and perforin.

In certain embodiments, CD4+ T cells are further sorted into subpopulations. For example, CD4+ T helper cells can be sorted into naive, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+ CD4+ T cell. In some embodiments, central memory CD4+ cells are CD62L positive and CD45RO positive. In some embodiments, effector CD4+ cells are CD62L and CD45RO negative.

The immune effector cells, such as T cells, can be genetically modified following isolation using known methods, or the immune effector cells can be activated and expanded (or differentiated in the case of progenitors) in vitro prior to being genetically modified. In a particular embodiment, the immune effector cells, such as T cells, are genetically modified with the chimeric antigen receptors contemplated herein (e.g., transduced with a viral vector comprising a nucleic acid encoding a CAR) and then are activated and expanded in vitro. In various embodiments, T cells can be activated and expanded before or after genetic modification to express a CAR, using methods as described, for example, in U.S. Pat. Nos. 6,352,694; 6,534,055; 6,905,680; 6,692, 964; 5,858,358; 6,887,466; 6,905,681; 7, 144,575; 7,067, 318; 7, 172,869; 7,232,566; 7, 175,843; 5,883,223; 6,905, 874; 6,797,514; 6,867,041; and U.S. Patent Application Publication No. 20060121005.

Generally, the T cells are expanded by contact with a surface having attached thereto an agent that stimulates a CD3 TCR complex associated signal and a ligand that stimulates a co-stimulatory molecule on the surface of the T cells. T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. Costimulation of accessory molecules on the surface of T cells, is also contemplated.

In particular embodiments, PBMCs or isolated T cells are contacted with a stimulatory agent and costimulatory agent, such as anti-CD3 and anti-CD28 antibodies, generally attached to a bead or other surface, in a culture medium with appropriate cytokines, such as IL-2, IL-7, and/or IL-15. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diacione, Besancon, France) can be used as can other methods commonly known in the art (Berg et al., *Transplant Proc.* 30(8):3975-3977, 1998; Haanen et al., *J. Exp. Med.* 190(9): 13191328, 1999; Garland et al., *J. Immunol Meth.* 227(1-2):53-63, 1999). Anti-CD3 and anti-CD28 antibodies attached to the same bead serve as a "surrogate" antigen presenting cell (APC). In other embodiments, the T cells may be activated and stimulated to proliferate with feeder cells and appropriate antibodies and cytokines using methods such as those described in U.S. Pat. Nos. 6,040, 177; 5,827,642; and WO2012129514.

In other embodiments, artificial APC (aAPC) made by engineering K562, U937, 721.221, T2, and C1R cells to direct the stable expression and secretion, of a variety of co-stimulatory molecules and cytokines. In a particular embodiment K32 or U32 aAPCs are used to direct the display of one or more antibody-based stimulatory molecules on the AAPC cell surface. Expression of various combinations of genes on the aAPC enables the precise determination of human T-cell activation requirements, such that aAPCs can be tailored for the optimal propagation of T-cell subsets with specific growth requirements and distinct functions. The aAPCs support ex vivo growth and long-term expansion of functional human CD8 T cells without requiring the addition of exogenous cytokines, in contrast to the use of natural APCs. Populations of T cells can be expanded by aAPCs expressing a variety of costimulatory molecules including, but not limited to, CD137L (4-1BBL), CD134L (OX40L), and/or CD80 or CD86. Finally, the aAPCs provide an efficient platform to expand genetically modified T cells and to maintain CD28 expression on CD8 T cells. aAPCs provided in WO 03/057171 and US2003/0147869 are hereby incorporated by reference in their entirety.

In one embodiment, CD34+ cells are transduced with a nucleic acid construct in accordance with the invention. In certain embodiments, the transduced CD34+ cells differentiate into mature immune effector cells in vivo following administration into a subject, generally the subject from whom the cells were originally isolated. In another embodiment, CD34+ cells may be stimulated in vitro prior to exposure to or after being genetically modified with a CAR as described herein, with one or more of the following cytokines: Flt-3 ligand (FLT3), stem cell factor (SCF), megakaryocyte growth and differentiation factor (TPO), IL-3 and IL-6 according to the methods described previously (Asheuer et al., 2004; Imren, et al., 2004).

The invention provides a population of modified immune effector cells for the treatment of cancer, the modified immune effector cells comprising a CAR as disclosed herein. For example, a population of modified immune effector cells are prepared from peripheral blood mononuclear cells (PBMCs) obtained from a patient diagnosed with B cell malignancy described herein (autologous donors). The PBMCs form a heterogeneous population of T lymphocytes that can be CD4+, CD8+, or CD4+ and CD8+.

The PBMCs also can include other cytotoxic lymphocytes such as NK cells or NKT cells. An expression vector carrying the coding sequence of a CAR contemplated herein can be introduced into a population of human donor T cells, NK cells or NKT cells. Successfully transduced T cells that carry the expression vector can be sorted using flow cytometry to isolate CD3 positive T cells and then further propagated to increase the number of these CAR protein expressing T cells in addition to cell activation using anti-CD3 antibodies and or anti-CD28 antibodies and IL-2 or any other methods known in the art as described elsewhere herein. Standard procedures are used for cryopreservation of T cells expressing the CAR protein T cells for storage and/or preparation for use in a human subject. In one embodiment, the in vitro transduction, culture and/or expansion of T cells are performed in the absence of non-human animal derived products such as fetal calf serum and fetal bovine serum. Since a heterogeneous population of PBMCs is genetically modified, the resultant transduced cells are a heterogeneous population of modified cells comprising a BCMA targeting CAR as contemplated herein.

In a further embodiment, a mixture of, e.g., one, two, three, four, five or more, different expression vectors can be used in genetically modifying a donor population of immune effector cells wherein each vector encodes a different chimeric antigen receptor protein as contemplated herein. The resulting modified immune effector cells forms a mixed population of modified cells, with a proportion of the modified cells expressing more than one different CAR proteins.

In one embodiment, the invention provides a method of storing genetically modified murine, human or humanized CAR protein expressing immune effector cells which target a BCMA protein, comprising cryopreserving the immune effector cells such that the cells remain viable upon thawing. A fraction of the immune effector cells expressing the CAR proteins can be cryopreserved by methods known in the art to provide a permanent source of such cells for the future treatment of patients afflicted with the B cell related condition. When needed, the cryopreserved transformed immune effector cells can be thawed, grown and expanded for more such cells.

As used herein, "cryopreserving," refers to the preservation of cells by cooling to sub-zero temperatures, such as (typically) 77 K or −196° C. (the boiling point of liquid nitrogen). Cryoprotective agents are often used at sub-zero temperatures to prevent the cells being preserved from damage due to freezing at low temperatures or warming to room temperature. Cryopreservative agents and optimal cooling rates can protect against cell injury. Cryoprotective agents which can be used include but are not limited to dimethyl sulfoxide (DMSO) (Lovelock and Bishop, Nature, 1959; 183: 1394-1395; Ashwood-Smith, Nature, 1961; 190: 1204-1205), glycerol, polyvinylpyrrolidine (Rinfret, Ann. N.Y. Acad. Sci., 1960; 85: 576), and polyethylene glycol (Sloviter and Ravdin, Nature, 1962; 196: 48). The preferred cooling rate is 1° to 3° C./minute. After at least two hours, the T cells have reached a temperature of −80° C. and can be placed directly into liquid nitrogen (−196° C.) for permanent storage such as in a long-term cryogenic storage vessel.

H. T Cell Manufacturing Methods

The T cells manufactured by the methods contemplated herein provide improved adoptive immunotherapy compositions. Without wishing to be bound to any particular theory, it is believed that the T cell compositions manufactured by the methods contemplated herein are imbued with superior properties, including increased survival, expansion in the relative absence of differentiation, and persistence in vivo. In one embodiment, a method of manufacturing T cells comprises contacting the cells with one or more agents that modulate a PI3K cell signaling pathway. In one embodiment, a method of manufacturing T cells comprises contacting the cells with one or more agents that modulate a PI3K/Akt/mTOR cell signaling pathway. In various embodiments, the T cells may be obtained from any source and contacted with the agent during the activation and/or expansion phases of the manufacturing process. The resulting T cell compositions are enriched in developmentally potent T cells that have the ability to proliferate and express one or more of the following biomarkers: CD62L, CCR7, CD28, CD27, CD122, CD127, CD197, and CD38. In one embodiment, populations of cell comprising T cells, that have been treated with one or more PI3K inhibitors is enriched for a population of CD8+ T cells co-expressing one or more or, or all of, the following biomarkers: CD62L, CD127, CD197, and CD38.

In one embodiment, modified T cells comprising maintained levels of proliferation and decreased differentiation are manufactured. In a particular embodiment, T cells are manufactured by stimulating T cells to become activated and to proliferate in the presence of one or more stimulatory signals and an agent that is an inhibitor of a PI3K cell signaling pathway.

The T cells can then be modified to express an anti-BCMA CARs. In one embodiment, the T cells are modified by transducing the T cells with a viral vector comprising an anti-BCMA CAR contemplated herein. In a certain embodiment, the T cells are modified prior to stimulation and activation in the presence of an inhibitor of a PI3K cell signaling pathway. In another embodiment, T cells are modified after stimulation and activation in the presence of an inhibitor of a PI3K cell signaling pathway. In a particular embodiment, T cells are modified within 12 hours, 24 hours, 36 hours, or 48 hours of stimulation and activation in the presence of an inhibitor of a PI3K cell signaling pathway.

After T cells are activated, the cells are cultured to proliferate. T cells may be cultured for at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion.

In various embodiments, T cell compositions are manufactured in the presence of one or more inhibitors of the PI3K pathway. The inhibitors may target one or more activities in the pathway or a single activity. Without wishing to be bound to any particular theory, it is contemplated that treatment or contacting T cells with one or more inhibitors of the PI3K pathway during the stimulation, activation, and/or expansion phases of the manufacturing process preferentially increases young T cells, thereby producing superior therapeutic T cell compositions.

In a particular embodiment, a method for increasing the proliferation of T cells expressing an engineered T cell receptor is provided. Such methods may comprise, for example, harvesting a source of T cells from a subject, stimulating and activating the T cells in the presence of one or more inhibitors of the PI3K pathway, modification of the T cells to express an anti-BCMA CAR, e.g., anti-BCMA02 CAR, and expanding the T cells in culture.

In a certain embodiment, a method for producing populations of T cells enriched for expression of one or more of the following biomarkers: CD62L, CCR7, CD28, CD27, CD122, CD127, CD197, and CD38. In one embodiment, young T cells comprise one or more of, or all of the following biological markers: CD62L, CD127, CD197, and CD38. In one embodiment, the young T cells lack expression of CD57, CD244, CD160, PD-1, CTLA4, TIM3, and LAG3 are provided. As discussed elsewhere herein, the expression levels young T cell biomarkers is relative to the expression levels of such markers in more differentiated T cells or immune effector cell populations.

In one embodiment, peripheral blood mononuclear cells (PBMCs) are used as the source of T cells in the T cell manufacturing methods contemplated herein. PBMCs form a heterogeneous population of T lymphocytes that can be $CD4^+$, $CD8^+$, or $CD4^+$ and $CD8^+$ and can include other mononuclear cells such as monocytes, B cells, NK cells and NKT cells. An expression vector comprising a polynucleotide encoding an engineered TCR or CAR contemplated herein can be introduced into a population of human donor T cells, NK cells or NKT cells. Successfully transduced T cells that carry the expression vector can be sorted using flow cytometry to isolate CD3 positive T cells and then further propagated to increase the number of the modified T cells in addition to cell activation using anti-CD3 antibodies and or anti-CD28 antibodies and IL-2, IL-7, and/or IL-15 or any other methods known in the art as described elsewhere herein.

Manufacturing methods contemplated herein may further comprise cryopreservation of modified T cells for storage and/or preparation for use in a human subject. T cells are cryopreserved such that the cells remain viable upon thawing. When needed, the cryopreserved transformed immune effector cells can be thawed, grown and expanded for more such cells. As used herein, "cryopreserving," refers to the preservation of cells by cooling to sub-zero temperatures, such as (typically) 77 K or −196° C. (the boiling point of liquid nitrogen). Cryoprotective agents are often used at sub-zero temperatures to prevent the cells being preserved from damage due to freezing at low temperatures or warming to room temperature. Cryopreservative agents and optimal cooling rates can protect against cell injury. Cryoprotective agents which can be used include but are not limited to dimethyl sulfoxide (DMSO) (Lovelock and Bishop, Nature, 1959; 183: 1394-1395; Ashwood-Smith, Nature, 1961; 190: 1204-1205), glycerol, polyvinylpyrrolidine (Rinfret, Ann. N Y. Acad. Sci., 1960; 85: 576), and polyethylene glycol (Sloviter and Ravdin, Nature, 1962; 196: 48). The preferred cooling rate is 1° to 3° C/minute. After at least two hours, the T cells have reached a temperature of −80° C. and can be placed directly into liquid nitrogen (−196° C.) for permanent storage such as in a long-term cryogenic storage vessel.

1. T Cells

The present invention contemplates the manufacture of improved CAR T cell compositions. T cells used for CAR T cell production may be autologous/autogeneic ("self") or non-autologous ("non-self," e.g., allogeneic, syngeneic or xenogeneic). In preferred embodiments, the T cells are obtained from a mammalian subject. In a more preferred embodiment, the T cells are obtained from a primate subject. In the most preferred embodiment, the T cells are obtained from a human subject.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation. In one embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. As would be appreciated by those of ordinary skill in the art, a washing step may be accomplished by methods known to those in the art, such as by using a semiautomated flowthrough centrifuge. For example, the Cobe 2991 cell processor, the Baxter CytoMate, or the like. After washing, the cells may be resuspended in a variety of biocompatible buffers or other saline solution with or without buffer. In certain embodiments, the undesirable components of the apheresis sample may be removed in the cell directly resuspended culture media.

In particular embodiments, a population of cells comprising T cells, e.g., PBMCs, is used in the manufacturing methods contemplated herein. In other embodiments, an isolated or purified population of T cells is used in the manufacturing methods contemplated herein. Cells can be isolated from peripheral blood mononuclear cells (PBMCs) by lysing the red blood cells and depleting the monocytes, for example, by centrifugation through a PERCOLL™ gradient. In some embodiments, after isolation of PBMC, both cytotoxic and helper T lymphocytes can be sorted into naïve, memory, and effector T cell subpopulations either before or after activation, expansion, and/or genetic modification.

A specific subpopulation of T cells, expressing one or more of the following markers: CD3, CD4, CD8, CD28, CD45RA, CD45RO, CD62, CD127, and HLA-DR can be further isolated by positive or negative selection techniques. In one embodiment, a specific subpopulation of T cells, expressing one or more of the markers selected from the group consisting of i) CD62L, CCR7, CD28, CD27, CD122, CD127, CD197; or ii) CD38 or CD62L, CD127, CD197, and CD38, is further isolated by positive or negative selection techniques. In various embodiments, the manufactured T cell compositions do not express or do not substantially express one or more of the following markers: CD57, CD244, CD160, PD-1, CTLA4, TIM3, and LAG3.

In one embodiment, expression of one or more of the markers selected from the group consisting of CD62L, CD127, CD197, and CD38 is increased at least 1.5 fold, at least 2 fold, at least 3 fold, at least 4 fold, at least 5 fold, at least 6 fold, at least 7 fold, at least 8 fold, at least 9 fold, at least 10 fold, at least 25 fold, or more compared to a population of T cells activated and expanded without a PI3K inhibitor.

In one embodiment, expression of one or more of the markers selected from the group consisting of CD57, CD244, CD160, PD-1, CTLA4, TIM3, and LAG3 is decreased at least 1.5 fold, at least 2 fold, at least 3 fold, at least 4 fold, at least 5 fold, at least 6 fold, at least 7 fold, at least 8 fold, at least 9 fold, at least 10 fold, at least 25 fold, or more compared to a population of T cells activated and expanded with a PI3K inhibitor.

In one embodiment, the manufacturing methods contemplated herein increase the number CAR T cells comprising one or more markers of naïve or developmentally potent T cells. Without wishing to be bound to any particular theory, the present inventors believe that treating a population of cells comprising T cells with one or more PI3K inhibitors results in an increase an expansion of developmentally potent T cells and provides a more robust and efficacious adoptive CAR T cell immunotherapy compared to existing CAR T cell therapies.

Illustrative examples of markers of naïve or developmentally potent T cells increased in T cells manufactured using the methods contemplated herein include, but are not limited to CD62L, CD127, CD197, and CD38. In particular embodiments, naïve T cells do not express do not express or do not substantially express one or more of the following markers: CD57, CD244, CD160, PD-1, BTLA, CD45RA, CTLA4, TIM3, and LAG3.

With respect to T cells, the T cell populations resulting from the various expansion methodologies contemplated herein may have a variety of specific phenotypic properties, depending on the conditions employed. In various embodiments, expanded T cell populations comprise one or more of the following phenotypic markers: CD62L, CD127, CD197, CD38, and HLA-DR.

In one embodiment, such phenotypic markers include enhanced expression of one or more of, or all of CD62L, CD127, CD197, and CD38. In particular embodiments, $CD8^+$ T lymphocytes characterized by the expression of phenotypic markers of naive T cells including CD62L, CD127, CD197, and CD38 are expanded.

In particular embodiments, T cells characterized by the expression of phenotypic markers of central memory T cells including CD45RO, CD62L, CD127, CD197, and CD38 and negative for granzyme B are expanded. In some embodiments, the central memory T cells are $CD45RO^+$, $CD62L^+$, $CD8^+$ T cells.

In certain embodiments, $CD4^+$ T lymphocytes characterized by the expression of phenotypic markers of naïve $CD4^+$ cells including CD62L and negative for expression of CD45RA and/or CD45RO are expanded. In some embodiments, $CD4^+$ cells characterized by the expression of phenotypic markers of central memory $CD4^+$ cells including CD62L and CD45RO positive. In some embodiments, effector $CD4^+$ cells are CD62L positive and CD45RO negative.

In certain embodiments, the T cells are isolated from an individual and activated and stimulated to proliferate in vitro prior to being genetically modified to express an anti-BCMA CAR. In this regard, the T cells may be cultured before and/or after being genetically modified (i.e., transduced or transfected to express an anti-BCMA CAR contemplated herein).

2. Activation and Expansion

In order to achieve sufficient therapeutic doses of T cell compositions, T cells are often subject to one or more rounds of stimulation, activation and/or expansion. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety.

T cells modified to express an anti-BCMA CAR can be activated and expanded before and/or after the T cells are modified. In addition, T cells may be contacted with one or more agents that modulate the PI3K cell signaling pathway before, during, and/or after activation and/or expansion. In one embodiment, T cells manufactured by the methods contemplated herein undergo one, two, three, four, or five or more rounds of activation and expansion, each of which may include one or more agents that modulate the PI3K cell signaling pathway.

In one embodiment, a costimulatory ligand is presented on an antigen presenting cell (e.g., an aAPC, dendritic cell, B cell, and the like) that specifically binds a cognate costimulatory molecule on a T cell, thereby providing a signal which, in addition to the primary signal provided by, for instance, binding of a TCR/CD3 complex, mediates a desired T cell response. Suitable costimulatory ligands include, but are not limited to, CD7, B7-1 (CD80), B7-2 (CD86), PD-L 1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, ILT3, ILT4, an agonist or antibody that binds Toll ligand receptor, and a ligand that specifically binds with B7-H3.

In a particular embodiment, a costimulatory ligand comprises an antibody or antigen binding fragment thereof that specifically binds to a costimulatory molecule present on a T cell, including but not limited to, CD27, CD28, 4-IBB, OX40, CD30, CD40, PD-1, 1COS, lymphocyte function-associated antigen-1 (LFA-1), CD7, LIGHT, NKG2C, B7-H3, and a ligand that specifically binds with CD83.

Suitable costimulatory ligands further include target antigens, which may be provided in soluble form or expressed on APCs or aAPCs that bind engineered TCRs or CARs expressed on modified T cells.

In various embodiments, a method for manufacturing T cells contemplated herein comprises activating a population of cells comprising T cells and expanding the population of T cells. T cell activation can be accomplished by providing a primary stimulation signal through the T cell TCR/CD3 complex or via stimulation of the CD2 surface protein and by providing a secondary costimulation signal through an accessory molecule, e.g, CD28.

The TCR/CD3 complex may be stimulated by contacting the T cell with a suitable CD3 binding agent, e.g., a CD3 ligand or an anti-CD3 monoclonal antibody. Illustrative examples of CD3 antibodies include, but are not limited to, OKT3, G19-4, BC3, and 64.1.

In another embodiment, a CD2 binding agent may be used to provide a primary stimulation signal to the T cells. Illustrative examples of CD2 binding agents include, but are not limited to, CD2 ligands and anti-CD2 antibodies, e.g., the T11.3 antibody in combination with the T11.1 or T11.2 antibody (Meuer, S. C. et al. (1984) *Cell* 36:897-906) and the 9.6 antibody (which recognizes the same epitope as TI 1.1) in combination with the 9-1 antibody (Yang, S. Y. et al. (1986) *J. Immunol.* 137:1097-1100). Other antibodies which bind to the same epitopes as any of the above described antibodies can also be used. Additional antibodies, or combinations of antibodies, can be prepared and identified by standard techniques as disclosed elsewhere herein.

In addition to the primary stimulation signal provided through the TCR/CD3 complex, or via CD2, induction of T cell responses requires a second, costimulatory signal. In particular embodiments, a CD28 binding agent can be used to provide a costimulatory signal. Illustrative examples of CD28 binding agents include but are not limited to: natural CD 28 ligands, e.g., a natural ligand for CD28 (e.g., a member of the B7 family of proteins, such as B7-1(CD80) and B7-2 (CD86); and anti-CD28 monoclonal antibody or fragment thereof capable of crosslinking the CD28 molecule, e.g., monoclonal antibodies 9.3, B-T3, XR-CD28, KOLT-2, 15E8, 248.23.2, and EX5.3D10.

In one embodiment, the molecule providing the primary stimulation signal, for example a molecule which provides stimulation through the TCR/CD3 complex or CD2, and the costimulatory molecule are coupled to the same surface.

In certain embodiments, binding agents that provide stimulatory and costimulatory signals are localized on the surface of a cell. This can be accomplished by transfecting or transducing a cell with a nucleic acid encoding the binding agent in a form suitable for its expression on the cell surface or alternatively by coupling a binding agent to the cell surface.

In another embodiment, the molecule providing the primary stimulation signal, for example a molecule which provides stimulation through the TCR/CD3 complex or CD2, and the costimulatory molecule are displayed on antigen presenting cells.

In one embodiment, the molecule providing the primary stimulation signal, for example a molecule which provides stimulation through the TCR/CD3 complex or CD2, and the costimulatory molecule are provided on separate surfaces.

In a certain embodiment, one of the binding agents that provide stimulatory and costimulatory signals is soluble (provided in solution) and the other agent(s) is provided on one or more surfaces.

In a particular embodiment, the binding agents that provide stimulatory and costimulatory signals are both provided in a soluble form (provided in solution).

In various embodiments, the methods for manufacturing T cells contemplated herein comprise activating T cells with anti-CD3 and anti-CD28 antibodies.

T cell compositions manufactured by the methods contemplated herein comprise T cells activated and/or expanded in the presence of one or more agents that inhibit a PI3K cell signaling pathway. T cells modified to express an anti-BCMA CAR can be activated and expanded before and/or after the T cells are modified. In particular embodiments, a population of T cells is activated, modified to express an anti-BCMA CAR, and then cultured for expansion.

In one embodiment, T cells manufactured by the methods contemplated herein comprise an increased number of T cells expressing markers indicative of high proliferative potential and the ability to self-renew but that do not express or express substantially undetectable markers of T cell differentiation. These T cells may be repeatedly activated and expanded in a robust fashion and thereby provide an improved therapeutic T cell composition.

In one embodiment, a population of T cells activated and expanded in the presence of one or more agents that inhibit a PI3K cell signaling pathway is expanded at least 1.5 fold, at least 2 fold, at least 3 fold, at least 4 fold, at least 5 fold, at least 6 fold, at least 7 fold, at least 8 fold, at least 9 fold, at least 10 fold, at least 25 fold, at least 50 fold, at least 100 fold, at least 250 fold, at least 500 fold, at least 1000 fold, or more compared to a population of T cells activated and expanded without a PI3K inhibitor.

In one embodiment, a population of T cells characterized by the expression of markers young T cells are activated and expanded in the presence of one or more agents that inhibit a PI3K cell signaling pathway is expanded at least 1.5 fold, at least 2 fold, at least 3 fold, at least 4 fold, at least 5 fold, at least 6 fold, at least 7 fold, at least 8 fold, at least 9 fold, at least 10 fold, at least 25 fold, at least 50 fold, at least 100 fold, at least 250 fold, at least 500 fold, at least 1000 fold, or more compared the population of T cells activated and expanded without a PI3K inhibitor.

In one embodiment, expanding T cells activated by the methods contemplated herein further comprises culturing a population of cells comprising T cells for several hours (about 3 hours) to about 7 days to about 28 days or any hourly integer value in between. In another embodiment, the T cell composition may be cultured for 14 days. In a particular embodiment, T cells are cultured for about 21 days. In another embodiment, the T cell compositions are cultured for about 2-3 days. Several cycles of stimulation/activation/expansion may also be desired such that culture time of T cells can be 60 days or more.

In particular embodiments, conditions appropriate for T cell culture include an appropriate media (e.g., Minimal Essential Media or RPMI Media 1640 or, X-vivo 15, (Lonza)) and one or more factors necessary for proliferation and viability including, but not limited to serum (e.g., fetal bovine or human serum), interleukin-2 (IL-2), insulin, IFN-γ, IL-4, IL-7, IL-21, GM-CSF, IL-10, IL-12, IL-15, TGFβ, and TNF-α or any other additives suitable for the growth of cells known to the skilled artisan.

Further illustrative examples of cell culture media include, but are not limited to RPMI 1640, Clicks, AIM-V, DMEM, MEM, a-MEM, F-12, X-Vivo 1 5, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells.

Illustrative examples of other additives for T cell expansion include, but are not limited to, surfactant, piasmanate, pH buffers such as HEPES, and reducing agents such as N-acetyl-cysteine and 2-mercaptoethanol Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02).

In particular embodiments, PBMCs or isolated T cells are contacted with a stimulatory agent and costimulatory agent, such as anti-CD3 and anti-CD28 antibodies, generally attached to a bead or other surface, in a culture medium with appropriate cytokines, such as IL-2, IL-7, and/or IL-15.

In other embodiments, artificial APC (aAPC) made by engineering K562, U937, 721.221, T2, and C1R cells to direct the stable expression and secretion, of a variety of costimulatory molecules and cytokines. In a particular embodiment K32 or U32 aAPCs are used to direct the display of one or more antibody-based stimulatory molecules on the AAPC cell surface. Populations of T cells can be expanded by aAPCs expressing a variety of costimulatory molecules including, but not limited to, CD137L (4-1BBL), CD134L (OX40L), and/or CD80 or CD86. Finally, the aAPCs provide an efficient platform to expand genetically modified T cells and to maintain CD28 expression on CD8 T cells. aAPCs provided in WO 03/057171 and US2003/0147869 are hereby incorporated by reference in their entirety.

3. Agents

In various embodiments, a method for manufacturing T cells is provided that expands undifferentiated or developmentally potent T cells comprising contacting T cells with an agent that modulates a PI3K pathway in the cells. In various embodiments, a method for manufacturing T cells is provided that expands undifferentiated or developmentally potent T cells comprising contacting T cells with an agent that modulates a PI3K/AKT/mTOR pathway in the cells. The cells may be contacted prior to, during, and/or after activation and expansion. The T cell compositions retain sufficient T cell potency such that they may undergo multiple rounds of expansion without a substantial increase in differentiation.

As used herein, the terms "modulate," "modulator," or "modulatory agent" or comparable term refer to an agent's ability to elicit a change in a cell signaling pathway. A modulator may increase or decrease an amount, activity of a pathway component or increase or decrease a desired effect or output of a cell signaling pathway. In one embodiment, the modulator is an inhibitor. In another embodiment, the modulator is an activator.

An "agent" refers to a compound, small molecule, e.g., small organic molecule, nucleic acid, polypeptide, or a fragment, isoform, variant, analog, or derivative thereof used in the modulation of a PI3K/AKT/mTOR pathway.

A "small molecule" refers to a composition that has a molecular weight of less than about 5 kD, less than about 4 kD, less than about 3 kD, less than about 2 kD, less than about 1 kD, or less than about 0.5 kD. Small molecules may comprise nucleic acids, peptides, polypeptides, peptidomimetics, peptoids, carbohydrates, lipids, components thereof or other organic or inorganic molecules. Libraries of chemical and/or biological mixtures, such as fungal, bacterial, or algal extracts, are known in the art and can be screened with any of the assays of the invention. Examples of methods for the synthesis of molecular libraries can be found in: (Carell et al., 1994a; Carell et al., 1994b; Cho et al., 1993; DeWitt et al., 1993; Gallop et al., 1994; Zuckermann et al., 1994).

An "analog" refers to a small organic compound, a nucleotide, a protein, or a polypeptide that possesses similar or identical activity or function(s) as the compound, nucleotide, protein or polypeptide or compound having the desired activity of the present invention, but need not necessarily comprise a sequence or structure that is similar or identical to the sequence or structure of the preferred embodiment.

A "derivative" refers to either a compound, a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide, protein or polypeptide possesses a similar or identical function as the parent polypeptide.

In various embodiments, the agent that modulates a PI3K pathway activates a component of the pathway. An "activator," or "agonist" refers to an agent that promotes, increases, or induces one or more activities of a molecule in a PI3K/AKT/mTOR pathway including, without limitation, a molecule that inhibits one or more activities of a PI3K.

In various embodiments, the agent that modulates a PI3K pathway inhibits a component of the pathway. An "inhibitor" or "antagonist" refers to an agent that inhibits, decreases, or reduces one or more activities of a molecule in a PI3K pathway including, without limitation, a PI3K. In one embodiment, the inhibitor is a dual molecule inhibitor. In particular embodiment, the inhibitor may inhibit a class of molecules have the same or substantially similar activities (a pan-inhibitor) or may specifically inhibit a molecule's activity (a selective or specific inhibitor). Inhibition may also be irreversible or reversible.

In one embodiment, the inhibitor has an IC50 of at least 1 nM, at least 2 nM, at least 5 nM, at least 10 nM, at least 50 nM, at least 100 nM, at least 200 nM, at least 500 nM, at least 1 µM, at least 10 µM, at least 50 µM, or at least 100 µM. IC50 determinations can be accomplished using any conventional techniques known in the art. For example, an IC50 can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the "IC50" value. Analogously, other inhibitory concentrations can be defined through appropriate determinations of activity.

In various embodiments, T cells are contacted or treated or cultured with one or more modulators of a PI3K pathway at a concentration of at least 1 nM, at least 2 nM, at least 5 nM, at least 10 nM, at least 50 nM, at least 100 nM, at least 200 nM, at least 500 nM, at least 1 µM, at least 10 µM, at least 50 µM, at least 100 µM, or at least 1 M.

In particular embodiments, T cells may be contacted or treated or cultured with one or more modulators of a PI3K pathway for at least 12 hours, 18 hours, at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion.

a. PI3K/Akt/mTOR Pathway

The phosphatidyl-inositol-3 kinase/Akt/mammalian target of rapamycin pathway serves as a conduit to integrate growth factor signaling with cellular proliferation, differentiation, metabolism, and survival. PI3Ks are a family of highly conserved intracellular lipid kinases. Class IA PI3Ks are activated by growth factor receptor tyrosine kinases (RTKs), either directly or through interaction with the insulin receptor substrate family of adaptor molecules. This activity results in the production of phosphatidyl-inositol-3,4,5-trisphosphate (PIP3) a regulator of the serine/threonine kinase Akt. mTOR acts through the canonical PI3K pathway via 2 distinct complexes, each characterized by different binding partners that confer distinct activities. mTORC1 (mTOR in complex with PRAS40, raptor, and mLST8/GβL) acts as a downstream effector of PI3K/Akt signaling, linking growth factor signals with protein translation, cell growth, proliferation, and survival. mTORC2 (mTOR in complex with rictor, mSIN1, protor, and mLST8) acts as an upstream activator of Akt.

Upon growth factor receptor-mediated activation of PI3K, Akt is recruited to the membrane through the interaction of its pleckstrin homology domain with PIP3, thus exposing its activation loop and enabling phosphorylation at threonine 308 (Thr308) by the constitutively active phosphoinositide-dependent protein kinase 1 (PDK1). For maximal activation, Akt is also phosphorylated by mTORC2, at serine 473 (Ser473) of its C-terminal hydrophobic motif. DNA-PK and HSP have also been shown to be important in the regulation of Akt activity. Akt activates mTORC1 through inhibitory phosphorylation of TSC2, which along with TSC1, negatively regulates mTORC1 by inhibiting the Rheb GTPase, a positive regulator of mTORC 1. mTORC1 has 2 well-defined substrates, p70S6K (referred to hereafter as S6K1) and 4E-BP1, both of which critically regulate protein synthesis. Thus, mTORC1 is an important downstream effector of PI3K, linking growth factor signaling with protein translation and cellular proliferation.

b. PI3K Inhibitors

As used herein, the term "PI3K inhibitor" refers to a nucleic acid, peptide, compound, or small organic molecule that binds to and inhibits at least one activity of PI3K. The PI3K proteins can be divided into three classes, class 1 PI3Ks, class 2 PI3Ks, and class 3 PI3Ks. Class 1 PI3Ks exist as heterodimers consisting of one of four p110 catalytic subunits (p110α, p110β, p110δ, and p110γ) and one of two families of regulatory subunits. A PI3K inhibitor of the present invention preferably targets the class 1 PI3K inhibitors. In one embodiment, a PI3K inhibitor will display selectivity for one or more isoforms of the class 1 PI3K inhibitors (i.e., selectivity for p110α, p110β, p110δ, and p110γ or one or more of p110α, p110β, p110δ, and p110γ). In another aspect, a PI3K inhibitor will not display isoform selectivity and be considered a "pan-PI3K inhibitor." In one embodiment, a PI3K inhibitor will compete for binding with ATP to the PI3K catalytic domain.

In certain embodiments, a PI3K inhibitor can, for example, target PI3K as well as additional proteins in the PI3K-AKT-mTOR pathway. In particular embodiments, a PI3K inhibitor that targets both mTOR and PI3K can be referred to as either an mTOR inhibitor or a PI3K inhibitor. A PI3K inhibitor that only targets PI3K can be referred to as a selective PI3K inhibitor. In one embodiment, a selective PI3K inhibitor can be understood to refer to an agent that exhibits a 50% inhibitory concentration with respect to PI3K that is at least 10-fold, at least 20-fold, at least 30-fold, at least 50-fold, at least 100-fold, at least 1000-fold, or more, lower than the inhibitor's IC50 with respect to mTOR and/or other proteins in the pathway.

In a particular embodiment, exemplary PI3K inhibitors inhibit PI3K with an IC50 (concentration that inhibits 50% of the activity) of about 200 nM or less, preferably about 100 nm or less, even more preferably about 60 nM or less, about 25 nM, about 10 nM, about 5 nM, about 1 nM, 100 μM, 50 μM, 25 μM, 10 μM, 1 μM, or less. In one embodiment, a PI3K inhibitor inhibits PI3K with an IC50 from about 2 nM to about 100 nm, more preferably from about 2 nM to about 50 nM, even more preferably from about 2 nM to about 15 nM.

Illustrative examples of PI3K inhibitors suitable for use in the T cell manufacturing methods contemplated herein include, but are not limited to, BKM120 (class 1 PI3K inhibitor, Novartis), XL147 (class 1 PI3K inhibitor, Exelixis), (pan-PI3K inhibitor, GlaxoSmithKline), and PX-866 (class 1 PI3K inhibitor; p110α, p110β, and p110γ isoforms, Oncothyreon).

Other illustrative examples of selective PI3K inhibitors include, but are not limited to BYL719, GSK2636771, TGX-221, AS25242, CAL-101, ZSTK474, and IPI-145.

Further illustrative examples of pan-PI3K inhibitors include, but are not limited to BEZ235, LY294002, GSK1059615, TG100713, and GDC-0941.

c. AKT Inhibitors

As used herein, the term "AKT inhibitor" refers to a nucleic acid, peptide, compound, or small organic molecule that inhibits at least one activity of AKT. AKT inhibitors can be grouped into several classes, including lipid-based inhibitors (e.g., inhibitors that target the pleckstrin homology domain of AKT which prevents AKT from localizing to plasma membranes), ATP-competitive inhibitors, and allosteric inhibitors. In one embodiment, AKT inhibitors act by binding to the AKT catalytic site. In a particular embodiment, Akt inhibitors act by inhibiting phosphorylation of downstream AKT targets such as mTOR. In another embodiment, AKT activity is inhibited by inhibiting the input signals to activate Akt by inhibiting, for example, DNA-PK activation of AKT, PDK-1 activation of AKT, and/or mTORC2 activation of Akt.

AKT inhibitors can target all three AKT isoforms, AKT1, AKT2, AKT3 or may be isoform selective and target only one or two of the AKT isoforms. In one embodiment, an AKT inhibitor can target AKT as well as additional proteins in the PI3K-AKT-mTOR pathway. An AKT inhibitor that only targets AKT can be referred to as a selective AKT inhibitor. In one embodiment, a selective AKT inhibitor can be understood to refer to an agent that exhibits a 50% inhibitory concentration with respect to AKT that is at least 10-fold, at least 20-fold, at least 30-fold, at least 50-fold, at least 100-fold, at least 1000-fold, or more lower than the inhibitor's IC50 with respect to other proteins in the pathway.

In a particular embodiment, exemplary AKT inhibitors inhibit AKT with an IC50 (concentration that inhibits 50% of the activity) of about 200 nM or less, preferably about 100 nm or less, even more preferably about 60 nM or less, about 25 nM, about 10 nM, about 5 nM, about 1 nM, 100 μM, 50 μM, 25 μM, 10 μM, 1 μM, or less. In one embodiment, an AKT inhibits AKT with an IC50 from about 2 nM to about 100 nm, more preferably from about 2 nM to about 50 nM, even more preferably from about 2 nM to about 15 nM.

Illustrative examples of AKT inhibitors for use in combination with auristatin based antibody-drug conjugates include, for example, perifosine (Keryx), MK2206 (Merck), VQD-002 (VioQuest), XL418 (Exelixis), GSK690693, GDC-0068, and PX316 (PROLX Pharmaceuticals).

An illustrative, non-limiting example of a selective Akt1 inhibitor is A-674563.

An illustrative, non-limiting example of a selective Akt2 inhibitor is CCT128930.

In particular embodiments, the Akt inhibitor DNA-PK activation of Akt, PDK-1 activation of Akt, mTORC2 activation of Akt, or HSP activation of Akt.

Illustrative examples of DNA-PK inhibitors include, but are not limited to, NU7441, PI-103, NU7026, PIK-75, and PP-121.

d. mTOR Inhibitors

The terms "mTOR inhibitor" or "agent that inhibits mTOR" refers to a nucleic acid, peptide, compound, or small organic molecule that inhibits at least one activity of an mTOR protein, such as, for example, the serine/threonine protein kinase activity on at least one of its substrates (e.g., p70S6 kinase 1, 4E-BP1, AKT/PKB and eEF2). mTOR inhibitors are able to bind directly to and inhibit mTORC1, mTORC2 or both mTORC1 and mTORC2.

Inhibition of mTORC1 and/or mTORC2 activity can be determined by a reduction in signal transduction of the PI3K/Akt/mTOR pathway. A wide variety of readouts can be utilized to establish a reduction of the output of such signaling pathway. Some non-limiting exemplary readouts include (1) a decrease in phosphorylation of Akt at residues, including but not limited to S473 and T308; (2) a decrease in activation of Akt as evidenced, for example, by a reduction of phosphorylation of Akt substrates including but not limited to Fox01/O3a T24/32, GSK3a/β; S21/9, and TSC2 T1462; (3) a decrease in phosphorylation of signaling molecules downstream of mTOR, including but not limited to ribosomal S6 S240/244, 70S6K T389, and 4EBP1 T37/46; and (4) inhibition of proliferation of cancerous cells.

In one embodiment, the mTOR inhibitors are active site inhibitors. These are mTOR inhibitors that bind to the ATP binding site (also referred to as ATP binding pocket) of mTOR and inhibit the catalytic activity of both mTORC1 and mTORC2. One class of active site inhibitors suitable for use in the T cell manufacturing methods contemplated herein are dual specificity inhibitors that target and directly inhibit both PI3K and mTOR. Dual specificity inhibitors bind to both the ATP binding site of mTOR and PI3K. Illustrative examples of such inhibitors include, but are not limited to: imidazoquinazolines, wortmannin, LY294002, PI-103 (Cayman Chemical), SF1126 (Semafore), BGT226 (Novartis), XL765 (Exelixis) and NVP-BEZ235 (Novartis).

Another class of mTOR active site inhibitors suitable for use in the methods contemplated herein selectively inhibit mTORC1 and mTORC2 activity relative to one or more type I phophatidylinositol 3-kinases, e.g., PI3 kinase α, β, γ, or δ. These active site inhibitors bind to the active site of mTOR but not PI3K. Illustrative examples of such inhibitors include, but are not limited to: pyrazolopyrimidines, Torin1 (Guertin and Sabatini), PP242 (2-(4-Amino-1-isopropyl-1H-pyrazolo[3,4-d]pyrimidin-3-yl)-1H-indol-5-ol), PP30, Ku-0063794, WAY-600 (Wyeth), WAY-687 (Wyeth), WAY-354 (Wyeth), and AZD8055 (Liu et al., Nature Review, 8, 627-644, 2009). I In one embodiment, a selective mTOR inhibitor refers to an agent that exhibits a 50% inhibitory concentration (IC50) with respect to mTORC1 and/or mTORC2, that is at least 10-fold, at least 20-fold, at least 50-fold, at least 100-fold, at least 1000-fold, or more, lower than the inhibitor's IC50 with respect to one, two, three, or more type I PI3-kinases or to all of the type I PI3-kinases.

Another class of mTOR inhibitors for use in the present invention are referred to herein as "rapalogs". As used herein the term "rapalogs" refers to compounds that specifically bind to the mTOR FRB domain (FKBP rapamycin binding domain), are structurally related to rapamycin, and retain the mTOR inhibiting properties. The term rapalogs excludes rapamycin. Rapalogs include esters, ethers, oximes, hydrazones, and hydroxylamines of rapamycin, as well as compounds in which functional groups on the rapamycin core structure have been modified, for example, by reduction or oxidation. Pharmaceutically acceptable salts of such compounds are also considered to be rapamycin derivatives. Illustrative examples of rapalogs suitable for use in the methods contemplated herein include, without limitation, temsirolimus (CC 1779), everolimus (RAD001), deforolimus (AP23573), AZD8055 (AstraZeneca), and OSI-027 (OSI).

In one embodiment, the agent is the mTOR inhibitor rapamycin (sirolimus).

In a particular embodiment, exemplary mTOR inhibitors for use in the present invention inhibit either mTORC1, mTORC2 or both mTORC1 and mTORC2 with an IC50 (concentration that inhibits 50% of the activity) of about 200 nM or less, preferably about 100 nm or less, even more preferably about 60 nM or less, about 25 nM, about 10 nM, about 5 nM, about 1 nM, 100 µM, 50 µM, 25 µM, 10 µM, 1 µM, or less. In one aspect, a mTOR inhibitor for use in the present invention inhibits either mTORC1, mTORC2 or both mTORC1 and mTORC2 with an IC50 from about 2 nM to about 100 nm, more preferably from about 2 nM to about 50 nM, even more preferably from about 2 nM to about 15 nM.

In one embodiment, exemplary mTOR inhibitors inhibit either PI3K and mTORC1 or mTORC2 or both mTORC1 and mTORC2 and PI3K with an IC50 (concentration that inhibits 50% of the activity) of about 200 nM or less, preferably about 100 nm or less, even more preferably about 60 nM or less, about 25 nM, about 10 nM, about 5 nM, about 1 nM, 100 µM, 50 µM, 25 µM, 10 µM, 1 µM, or less. In one aspect, a mTOR inhibitor for use in the present invention inhibits PI3K and mTORC1 or mTORC2 or both mTORC1 and mTORC2 and PI3K with an IC50 from about 2 nM to about 100 nm, more preferably from about 2 nM to about 50 nM, even more preferably from about 2 nM to about 15 nM.

Further illustrative examples of mTOR inhibitors suitable for use in particular embodiments contemplated herein include, but are not limited to AZD8055, INK128, rapamycin, PF-04691502, and everolimus.

mTOR has been shown to demonstrate a robust and specific catalytic activity toward the physiological substrate proteins, p70 S6 ribosomal protein kinase I (p70S6K1) and eIF4E binding protein 1 (4EBP1) as measured by phosphor-specific antibodies in Western blotting.

In one embodiment, the inhibitor of the PI3K/AKT/mTOR pathway is a s6 kinase inhibitor selected from the group consisting of: BI-D1870, H89, PF-4708671, FMK, and AT7867.

I. Compositions and Formulations

The compositions contemplated herein may comprise one or more polypeptides, polynucleotides, vectors comprising same, genetically modified immune effector cells, etc., as contemplated herein. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution;

ethyl alcohol; phosphate buffer solutions; and any other compatible substances employed in pharmaceutical formulations.

In particular embodiments, compositions of the present invention comprise an amount of CAR-expressing immune effector cells contemplated herein. As used herein, the term "amount" refers to "an amount effective" or "an effective amount" of a genetically modified therapeutic cell, e.g., T cell, to achieve a beneficial or desired prophylactic or therapeutic result, including clinical results.

A "prophylactically effective amount" refers to an amount of a genetically modified therapeutic cell effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a genetically modified therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient). When a therapeutic amount is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mL or less, even 250 mL or 100 mL or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen (e.g., κ or λ light chain), lower numbers of cells, in the range of $10^6$/kilogram ($10^6$-$10^{11}$ per patient) may be administered. CAR expressing cell compositions may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response.

Generally, compositions comprising the cells activated and expanded as described herein may be utilized in the treatment and prevention of diseases that arise in individuals who are immunocompromised. In particular, compositions comprising the CAR-modified T cells contemplated herein are used in the treatment of B cell malignancies. The CAR-modified T cells of the present invention may be administered either alone, or as a pharmaceutical composition in combination with carriers, diluents, excipients, and/or with other components such as IL-2 or other cytokines or cell populations. In particular embodiments, pharmaceutical compositions contemplated herein comprise an amount of genetically modified T cells, in combination with one or more pharmaceutically or physiologically acceptable carriers, diluents or excipients.

Pharmaceutical compositions of the present invention comprising a CAR-expressing immune effector cell population, such as T cells, may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for parenteral administration, e.g., intravascular (intravenous or intraarterial), intraperitoneal or intramuscular administration.

The liquid pharmaceutical compositions, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, compositions contemplated herein comprise an effective amount of CAR-expressing immune effector cells, alone or in combination with one or more therapeutic agents. Thus, the CAR-expressing immune effector cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising CAR-expressing immune effector cells disclosed herein may be administered in conjunction with any number of chemotherapeutic agents. Illustrative examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®., Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on cancers such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the compositions described herein. In one embodiment, the composition comprising CAR-expressing immune effector cells is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Other exemplary NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol of proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

Illustrative examples of therapeutic antibodies suitable for combination with the CAR modified T cells contemplated herein, include but are not limited to, bavituximab, bevacizumab (avastin), bivatuzumab, blinatumomab, conatumumab, daratumumab, duligotumab, dacetuzumab, dalotuzumab, elotuzumab (HuLuc63), gemtuzumab, ibritumomab, indatuximab, inotuzumab, lorvotuzumab, lucatumumab, milatuzumab, moxetumomab, ocaratuzumab, ofatumumab, rituximab, siltuximab, teprotumumab, and ublituximab.

In certain embodiments, the compositions described herein are administered in conjunction with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, IL-21, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In particular embodiments, a composition comprises CAR T cells contemplated herein that are cultured in the presence of a PI3K inhibitor as disclosed herein and express one or more of the following markers: CD3, CD4, CD8, CD28, CD45RA, CD45RO, CD62, CD127, and HLA-DR can be further isolated by positive or negative selection techniques.

In one embodiment, a composition comprises a specific subpopulation of T cells, expressing one or more of the markers selected from the group consisting of CD62L, CCR7, CD28, CD27, CD122, CD127, CD197; and CD38 or CD62L, CD127, CD197, and CD38, is further isolated by positive or negative selection techniques. In various embodiments, compositions do not express or do not substantially express one or more of the following markers: CD57, CD244, CD160, PD-1, CTLA4, TIM3, and LAG3.

In one embodiment, expression of one or more of the markers selected from the group consisting of CD62L, CD127, CD197, and CD38 is increased at least 1.5 fold, at least 2 fold, at least 3 fold, at least 4 fold, at least 5 fold, at least 6 fold, at least 7 fold, at least 8 fold, at least 9 fold, at least 10 fold, at least 25 fold, or more compared to a population of T cells activated and expanded without a PI3K inhibitor.

In one embodiment, expression of one or more of the markers selected from the group consisting of CD57, CD244, CD160, PD-1, CTLA4, TIM3, and LAG3 is decreased at least 1.5 fold, at least 2 fold, at least 3 fold, at least 4 fold, at least 5 fold, at least 6 fold, at least 7 fold, at least 8 fold, at least 9 fold, at least 10 fold, at least 25 fold, or more compared to a population of T cells activated and expanded with a PI3K inhibitor.

J. Therapeutic Methods

The genetically modified immune effector cells contemplated herein provide improved methods of adoptive immunotherapy for use in the treatment of B cell related conditions that include, but are not limited to immunoregulatory conditions and hematological malignancies.

In particular embodiments, the specificity of a primary immune effector cell is redirected to B cells by genetically modifying the primary immune effector cell with a CAR contemplated herein. In various embodiments, a viral vector is used to genetically modify an immune effector cell with a particular polynucleotide encoding a CAR comprising a murine anti-BCMA antigen binding domain that binds a BCMA polypeptide; a hinge domain; a transmembrane (TM) domain, a short oligo- or polypeptide linker, that links the TM domain to the intracellular signaling domain of the CAR; and one or more intracellular co-stimulatory signaling domains; and a primary signaling domain.

In one embodiment, the present invention includes a type of cellular therapy where T cells are genetically modified to express a CAR that targets BCMA expressing B cells. In another embodiment, anti-BCMA CAR T cells are cultured in the presence of IL-2 and a PI3K inhibitor to increase the therapeutic properties and persistence of the CAR T cells. The CAR T cell are then infused to a recipient in need thereof. The infused cell is able to kill disease causing B cells in the recipient. Unlike antibody therapies, CAR T cells are able to replicate in vivo resulting in long-term persistence that can lead to sustained cancer therapy.

In one embodiment, the CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth.

In particular embodiments, compositions comprising immune effector cells comprising the CARs contemplated herein are used in the treatment of conditions associated with abnormal B cell activity.

Illustrative examples of conditions that can be treated, prevented or ameliorated using the immune effector cells comprising the CARs contemplated herein include, but are not limited to: systemic lupus erythematosus, rheumatoid arthritis, myasthenia gravis, autoimmune hemolytic anemia, idiopathic thrombocytopenia purpura, anti-phospholipid syndrome, Chagas' disease, Grave's disease, Wegener's granulomatosis, poly-arteritis *nodosa*, Sjogren's syndrome, pemphigus vulgaris, scleroderma, multiple sclerosis, anti-phospholipid syndrome, ANCA associated vasculitis, Goodpasture's disease, Kawasaki disease, and rapidly progressive glomerulonephritis.

The modified immune effector cells may also have application in plasma cell disorders such as heavy-chain disease, primary or immunocyte-associated amyloidosis, and monoclonal gammopathy of undetermined significance (MGUS).

As use herein, "B cell malignancy" refers to a type of cancer that forms in B cells (a type of immune system cell) as discussed infra.

In particular embodiments, compositions comprising CAR-modified T cells contemplated herein are used in the treatment of hematologic malignancies, including but not limited to B cell malignancies such as, for example, multiple myeloma (MM) and non-Hodgkin's lymphoma (NHL).

Multiple myeloma is a B cell malignancy of mature plasma cell morphology characterized by the neoplastic transformation of a single clone of these types of cells. These plasma cells proliferate in BM and may invade adjacent bone and sometimes the blood. Variant forms of multiple myeloma include overt multiple myeloma, smoldering multiple myeloma, plasma cell leukemia, non-secretory myeloma, IgD myeloma, osteosclerotic myeloma, solitary plasmacytoma of bone, and extramedullary plasmacytoma (see, for example, Braunwald, et al. (eds), *Harrison's Principles of Internal Medicine,* 15th Edition (McGraw-Hill 2001)).

Non-Hodgkin lymphoma encompasses a large group of cancers of lymphocytes (white blood cells). Non-Hodgkin lymphomas can occur at any age and are often marked by lymph nodes that are larger than normal, fever, and weight loss. There are many different types of non-Hodgkin lymphoma. For example, non-Hodgkin's lymphoma can be divided into aggressive (fast-growing) and indolent (slow-growing) types. Although non-Hodgkin lymphomas can be derived from B cells and T-cells, as used herein, the term "non-Hodgkin lymphoma" and "B cell non-Hodgkin lymphoma" are used interchangeably. B cell non-Hodgkin lymphomas (NHL) include Burkitt lymphoma, chronic lymphocytic leukemia/small lymphocytic lymphoma (CLL/SLL), diffuse large B cell lymphoma, follicular lymphoma, immunoblastic large cell lymphoma, precursor B-lymphoblastic lymphoma, and mantle cell lymphoma. Lymphomas that occur after bone marrow or stem cell transplantation are usually B cell non-Hodgkin lymphomas.

Chronic lymphocytic leukemia (CLL) is an indolent (slow-growing) cancer that causes a slow increase in immature white blood cells called B lymphocytes, or B cells. Cancer cells spread through the blood and bone marrow, and can also affect the lymph nodes or other organs such as the liver and spleen. CLL eventually causes the bone marrow to fail. Sometimes, in later stages of the disease, the disease is called small lymphocytic lymphoma.

In particular embodiments, methods comprising administering a therapeutically effective amount of CAR-expressing immune effector cells contemplated herein or a composition comprising the same, to a patient in need thereof, alone or in combination with one or more therapeutic agents, are provided. In certain embodiments, the cells of the invention are used in the treatment of patients at risk for developing a condition associated with abnormal B cell activity or a B cell malignancy. Thus, the present invention provides methods for the treatment or prevention of a condition associated with abnormal B cell activity or a B cell malignancy comprising administering to a subject in need thereof, a therapeutically effective amount of the CAR-modified cells contemplated herein.

As used herein, the terms "individual" and "subject" are often used interchangeably and refer to any animal that exhibits a symptom of a disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., a B cell malignancy, that can be treated with the gene therapy vectors, cell-based therapeutics, and methods disclosed elsewhere herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include human patients that have a B cell malignancy, have been diagnosed with a B cell malignancy, or are at risk or having a B cell malignancy.

As used herein, the term "patient" refers to a subject that has been diagnosed with a particular disease, disorder, or condition that can be treated with the gene therapy vectors, cell-based therapeutics, and methods disclosed elsewhere herein.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

By "enhance" or "promote," or "increase" or "expand" refers generally to the ability of a composition contemplated herein, e.g., a genetically modified T cell or vector encoding a CAR, to produce, elicit, or cause a greater physiological response (i.e., downstream effects) compared to the response caused by either vehicle or a control molecule/composition. A measurable physiological response may include an increase in T cell expansion, activation, persistence, and/or an increase in cancer cell killing ability, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. A "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

By "maintain," or "preserve," or "maintenance," or "no change," or "no substantial change," or "no substantial decrease" refers generally to the ability of a composition contemplated herein to produce, elicit, or cause a lesser physiological response (i.e., downstream effects) in a cell, as compared to the response caused by either vehicle, a control molecule/composition, or the response in a particular cell lineage. A comparable response is one that is not significantly different or measurable different from the reference response.

In one embodiment, a method of treating a B cell related condition in a subject in need thereof comprises administering an effective amount, e.g., therapeutically effective amount of a composition comprising genetically modified immune effector cells contemplated herein. The quantity and frequency of administration will be determined by such factors as the condition of the patient, and the type and severity of the patient's disease, although appropriate dosages may be determined by clinical trials.

In one embodiment, the amount of T cells in the composition administered to a subject is at least $0.1 \times 10^5$ cells, at least $0.5 \times 10^5$ cells, at least $1 \times 10^5$ cells, at least $5 \times 10^5$ cells, at least $1 \times 10^6$ cells, at least $0.5 \times 10^7$ cells, at least $1 \times 10^7$ cells, at least $0.5 \times 10^8$ cells, at least $1 \times 10^8$ cells, at least $0.5 \times 10^9$ cells, at least $1 \times 10^9$ cells, at least $2 \times 10^9$ cells, at least $3 \times 10^9$ cells, at least $4 \times 10^9$ cells, at least $5 \times 10^9$ cells, or at least $1 \times 10^{10}$ cells. In particular embodiments, about $1 \times 10^7$ CAR T cells to about $1 \times 10^9$ CAR T cells, about $2 \times 10^7$ CAR T cells to about $0.9 \times 10^9$ CAR T cells, about $3 \times 10^7$ CAR T cells to about $0.8 \times 10^9$ CAR T cells, about $4 \times 10^7$ CAR T cells to about $0.7 \times 10^9$ CAR T cells, about $5 \times 10^7$ CAR T cells to about $0.6 \times 10^9$ CAR T cells, or about $5 \times 10^7$ CAR T cells to about $0.5 \times 10^9$ CAR T cells are administered to a subject.

In one embodiment, the amount of T cells in the composition administered to a subject is at least $0.1 \times 10^4$ cells/kg of bodyweight, at least $0.5 \times 10^4$ cells/kg of bodyweight, at least $1 \times 10^4$ cells/kg of bodyweight, at least $5 \times 10^4$ cells/kg of bodyweight, at least $1 \times 10^5$ cells/kg of bodyweight, at least $0.5 \times 10^6$ cells/kg of bodyweight, at least $1 \times 10^6$ cells/kg of bodyweight, at least $0.5 \times 10^7$ cells/kg of bodyweight, at least $1 \times 10^7$ cells/kg of bodyweight, at least $0.5 \times 10^8$ cells/kg of bodyweight, at least $1 \times 10^8$ cells/kg of bodyweight, at least $2 \times 10^8$ cells/kg of bodyweight, at least $3 \times 10^8$ cells/kg of bodyweight, at least $4 \times 10^8$ cells/kg of bodyweight, at least $5 \times 10^8$ cells/kg of bodyweight, or at least $1 \times 10^9$ cells/kg of bodyweight. In particular embodiments, about $1 \times 10^6$ CAR T cells/kg of bodyweight to about $1 \times 10^8$ CAR T cells/kg of bodyweight, about $2 \times 10^6$ CAR T cells/kg of bodyweight to about $0.9 \times 10^8$ CAR T cells/kg of bodyweight, about $3 \times 10^6$ CAR T cells/kg of bodyweight to about $0.8 \times 10^8$ CAR T cells/kg of bodyweight, about $4 \times 10^6$ CAR T cells/kg of bodyweight to about $0.7 \times 10^8$ CAR T cells/kg of bodyweight, about $5 \times 10^6$ CAR T cells/kg of bodyweight to about $0.6 \times 10^8$ CAR T cells/kg of bodyweight, or about $5 \times 10^6$ CAR T cells/kg of bodyweight to about $0.5 \times 10^8$ CAR T cells/kg of bodyweight are administered to a subject.

One of ordinary skill in the art would recognize that multiple administrations of the compositions of the invention may be required to effect the desired therapy. For example a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated immune effector cells to a subject and then subsequently redraw blood (or have an apheresis performed), activate immune effector cells therefrom according to the present invention, and reinfuse the patient with these activated and expanded immune effector cells. This process can be carried out multiple times every few weeks. In certain embodiments, immune effector cells can be activated from blood draws of from 10 cc to 400 cc. In certain embodiments, immune effector cells are activated from blood draws of 20 cc, 30 cc, 40 cc, 50 cc, 60 cc, 70 cc, 80 cc, 90 cc, 100 cc, 150 cc, 200 cc, 250 cc, 300 cc, 350 cc, or 400 cc or more. Not to be bound by theory, using this multiple blood draw/multiple reinfusion protocol may serve to select out certain populations of immune effector cells.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

In one embodiment, a subject in need thereof is administered an effective amount of a composition to increase a cellular immune response to a B cell related condition in the subject. The immune response may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present invention, which are well described in the art; e.g., *Current Protocols in Immunology*, Edited by: John E. Coligan, Ada M. Kruisbeek, David H. Margulies, Ethan M. Shevach, Warren Strober (2001) John Wiley & Sons, NY, N.Y.

In the case of T cell-mediated killing, CAR-ligand binding initiates CAR signaling to the T cell, resulting in activation of a variety of T cell signaling pathways that induce the T cell to produce or release proteins capable of inducing target cell apoptosis by various mechanisms. These T cell-mediated mechanisms include (but are not limited to) the transfer of intracellular cytotoxic granules from the T cell into the target cell, T cell secretion of pro-inflammatory cytokines that can induce target cell killing directly (or indirectly via recruitment of other killer effector cells), and up regulation of death receptor ligands (e.g. FasL) on the T cell surface that induce target cell apoptosis following binding to their cognate death receptor (e.g. Fas) on the target cell.

In one embodiment, the invention provides a method of treating a subject diagnosed with a B cell related condition comprising removing immune effector cells from a subject diagnosed with a BCMA-expressing B cell related condition, genetically modifying said immune effector cells with a vector comprising a nucleic acid encoding a CAR as contemplated herein, thereby producing a population of modified immune effector cells, and administering the population of modified immune effector cells to the same subject. In a preferred embodiment, the immune effector cells comprise T cells.

In certain embodiments, the present invention also provides methods for stimulating an immune effector cell mediated immune modulator response to a target cell population in a subject comprising the steps of administering to the subject an immune effector cell population expressing a nucleic acid construct encoding a CAR molecule.

The methods for administering the cell compositions described herein includes any method which is effective to result in reintroduction of ex vivo genetically modified immune effector cells that either directly express a CAR of the invention in the subject or on reintroduction of the genetically modified progenitors of immune effector cells that on introduction into a subject differentiate into mature immune effector cells that express the CAR. One method comprises transducing peripheral blood T cells ex vivo with a nucleic acid construct in accordance with the invention and returning the transduced cells into the subject.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Construction of BCMA CARS

CARs containing murine anti-BCMA scFv antibodies were designed to contain an MND promoter operably linked to anti-BMCA scFv, a hinge and transmembrane domain from CD8α and a CD137 co-stimulatory domains followed by the intracellular signaling domain of the CD3ζ chain. See, e.g., FIG. 1. The BCMA CAR shown in FIG. 1 comprises a CD8α signal peptide (SP) sequence for the surface expression on immune effector cells. The polynucleotide sequence of an exemplary BCMA CAR is set forth in SEQ ID NO: 10; an exemplary polypeptide sequences of a BCMA CAR is set forth in SEQ ID NO: 9; and a vector map of an exemplary CAR construct is shown in FIG. 1. Table 3 shows the Identity, Genbank Reference, Source Name and Citation for the various nucleotide segments of an BCMA CAR lentiviral vector.

TABLE 3

| Nucleotides | Identity | GenBank Reference | Source Name | Citation |
|---|---|---|---|---|
| 1-185 | pUC19 plasmid backbone | Accession #L09137.2 nt 1-185 | pUC19 | New England Biolabs |
| 185-222 | Linker | Not applicable | Synthetic | Not applicable |
| 223-800 | CMV | Not Applicable | pHCMV | (1994) PNAS 91: 9564-68 |
| 801-1136 | R, U5, PBS, and packaging sequences | Accession #M19921.2 nt 454-789 | pNL4-3 | Maldarelli, et. al. (1991) J Virol: 65(11): 5732-43 |
| 1137-1139 | Gag start codon (ATG) changed to stop codon (TAG) | Not Applicable | Synthetic | Not applicable |
| 1140-1240 | HIV-1 gag sequence | Accession #M19921.2 nt 793-893 | pNL4-3 | Maldarelli, et. al. (1991) J Virol: 65(11): 5732-43 |
| 1241-1243 | HIV-1 gag sequence changed to a second stop codon | Not Applicable | Synthetic | Not applicable |
| 1244-1595 | HIV-1 gag sequence | Accession #M19921.2 nt 897-1248 | pNL4-3 | Maldarelli, et. al. (1991) J Virol: 65(11): 5732-43 |
| 1596-1992 | HIV-1 pol cPPT/CTS | Accession #M19921.2 nt 4745-5125 | pNL4-3 | Maldarelli, et. al. (1991) J Virol: 65(11): 5732-43 |
| 1993-2517 | HIV-1, isolate HXB3 env region (RRE) | Accession #M14100.1 nt 1875-2399 | PgTAT-CMV | Malim, M. H. Nature (1988) 335: 181-183 |
| 2518-2693 | HIV-1 env sequences S/A | Accession #M19921.2 nt 8290-8470 | pNL4-3 | Maldarelli, et. al. (1991) J Virol: 65(11): 5732-43 |
| 2694-2708 | Linker | Not applicable | Synthetic | Not applicable |
| 2709-3096 | MND | Not applicable | pccl-c-MNDU3c-x2 | Challita et al. (1995) J. Virol. 69: 748-755 |
| 3097-3124 | Linker | Not applicable | Synthetic | Not applicable |
| 3125-3187 | Signal peptide | Accession # NM_001768 | CD8a signal peptide | Not applicable |
| 3188-3934 | BCMA02 scFv ($V_L$1-linker-$V_H$0) | Not applicable | Synthetic | Not applicable |
| 3935-4141 | CD8a hinge and TM | Accession # NM_001768 | CD8a hinge and TM | Milone et al (2009) Mol Ther 17(8): 1453-64 |
| 4144-4269 | CD137 (4-1BB) signaling domain | Accession # NM_001561 | CD137 signaling domain | Milone et al (2009) Mol Ther 17(8): 1453-64 |
| 4270-4606 | CD3-ζ signaling domain | Accession # NM_000734 | CD3-ζ signaling domain | Milone et al (2009) Mol Ther 17(8): 1453-64 |
| 4607-4717 | HIV-1 ppt and part of 3' U3 | Accession #M19921.2 nt 9005-9110 | pNL4-3 | Maldarelli, et. al. (1991) J Virol: 65(11): 5732-43 |
| 4718-4834 | HIV-1 part of U3 (399bp deletion) and R | Accession #M19921.2 nt 9511-9627 | pNL4-3 | Maldarelli, et. al. (1991) J Virol: 65(11): 5732-43 |
| 4835-4858 | Synthetic polyA | Not applicable | Synthetic | Levitt, N. Genes & Dev (1989) 3: 1019-1025 |
| 4859-4877 | Linker | Not applicable | Synthetic | Not Applicable |
| 4878-7350 | pUC19 backbone | Accession #L09137.2 nt 2636-2686 | pUC19 | New England Biolabs |

Example 2

Evaluation of a Murine BCMA CAR

Introduction

Adoptive transfer of T cells genetically engineered with chimeric antigen receptors (CAR) has emerged as a promising approach to treat cancers. A CAR is an artificial molecule comprised of an antigen reactive single chain variable fragment (scFv) fused to T cell signaling domains via a transmembrane region. In this example, a CAR molecule specific to B cell maturation antigen (BCMA) was evaluated. BCMA is expressed on multiple myeloma, plasmacytoma, and some lymphomas yet normal expression is limited to plasma cells (Avery et al., 2003; Carpenito et al., 2009; Chiu et al., 2007).

Anti-BCMA02 CAR was constructed using sequences from a mouse anti-BCMA antibody (C11D5.3). Anti-BCMA10 CAR was constructed using modified sequences and is a "humanized" version of anti-BCMA02 CAR. In a series of in vitro assays, anti-BCMA02 CAR T cells and anti-BCMA10 CAR T cells both exhibited tumor specificity, high CAR expression, and caused potent reactivity to antigen expressing targets. Anti-BCMA02 CAR T cells and anti-BCMA10 CAR T cells were shown to have comparable reactivity to BCMA-expressing tumor cell lines. Although both anti-BCMA02 CAR T cells and anti-BCMA10 CAR T cells were capable of causing regressions in a mouse tumor model, anti-BCMA10 CAR T cells displayed antigen-independent inflammatory cytokine secretion, and thus, have the potential to cause clinical toxicities associated high cytokine levels.

Results

Tonic Inflammatory Cytokine Release from Anti-BCMA10 T Cells Associated with Apoptosis BCMA protein is detectable in the serum of patients with multiple myeloma (Sanchez et al., 2012). Average serum BCMA in multiple myeloma patients was 10 ng/mL but peaked at levels up to 100 ng/mL. The impact of physiological soluble BCMA levels on the anti-BCMA CAR T cell candidates was evaluated.

Figure 2A:
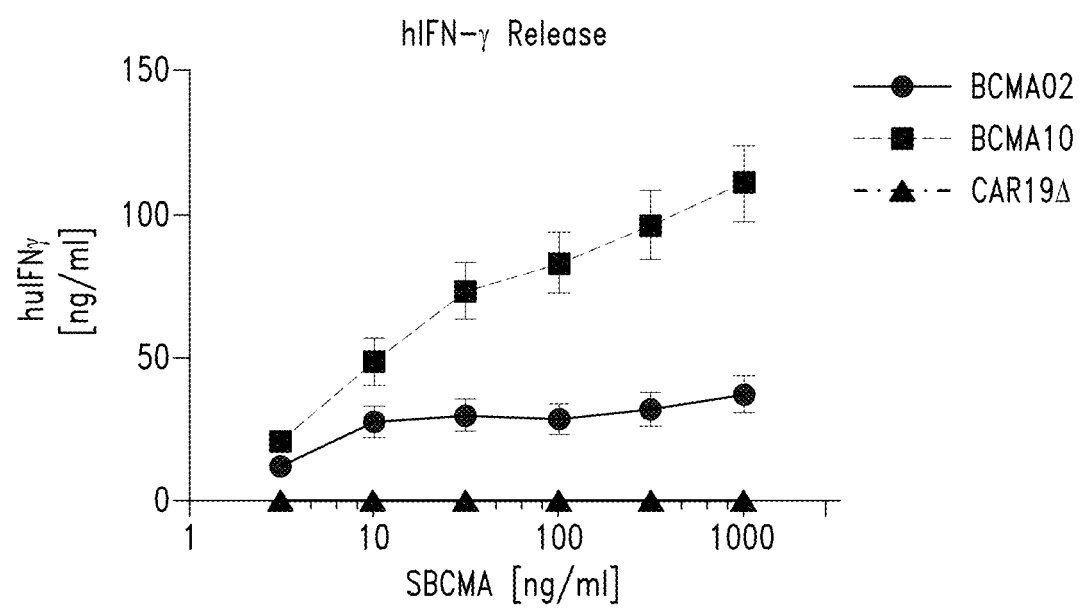
FIG. 2a shows the amount of IFNg released from anti-BCMA02 CAR T cells, anti-BCMA10 CART cells, and CAR19Δ T cells after the cells were co-cultured for 24 hours with K562 cells expressing BCMA.
Figure 2B:
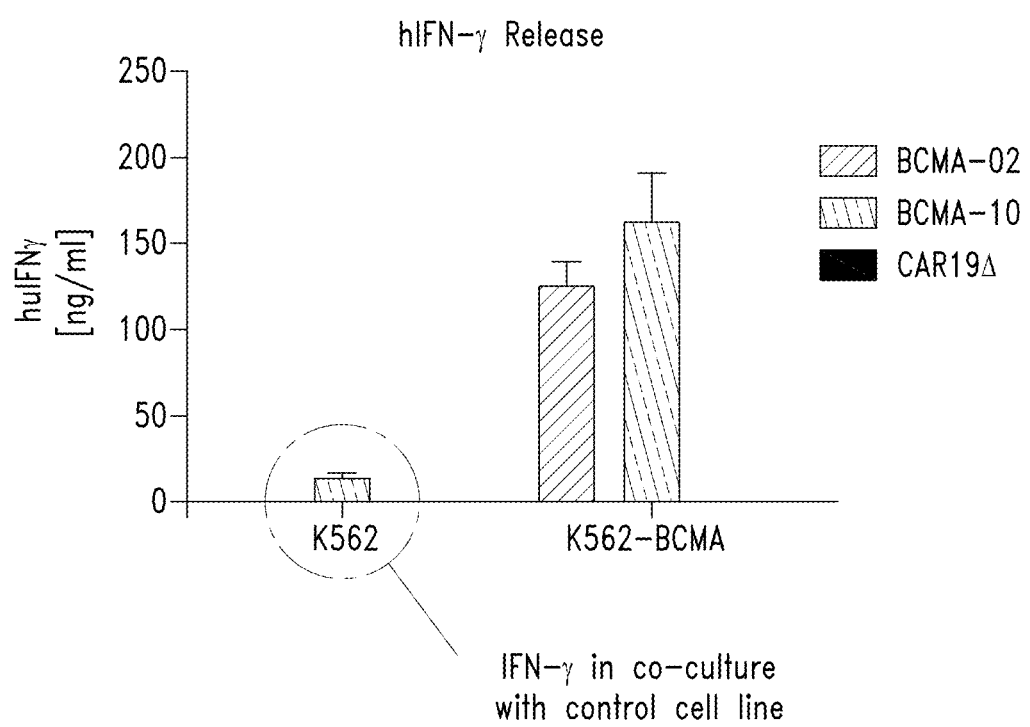
FIG. 2b shows the amount of IFNg released from anti-BCMA02 CAR T cells, anti-BCMA10 CART cells, and CAR19Δ T cells after the cells were co-cultured for 24 hours with K562 cells that lack BCMA expression compared to K562 cells expressing BCMA.

IFNγ release from anti-BCMA02 CAR T cells, anti-BCMA10 CART cells, and CAR19Δ T cells was examined after a 24 hour culture with soluble BCMA (FIG. 2a). Anti-BCMA02 CAR T cells responded with minimal cytokine release after 24 hour culture with up to 1 ug/mL BCMA. In contrast, anti-BCMA10 CAR T cells responded with increasing levels of IFNγ that were proportional to the concentration of soluble BCMA added to the culture. At 100 ng/mL BCMA, the maximum levels reported in multiple myeloma patients, anti-BCMA10 CAR T cells secreted 82.1 ng/ml IFNγ compared to 28.8 ng/ml IFNγ secreted by anti-BCMA02 CAR T cells. IFNγ was even detected in several co-culture experiments with anti-BCMA10 CAR T cells plus control cell lines that lacked BCMA antigen (FIG. 2b, K562 co-culture). These data suggested that anti-BCMA10 CAR T cells had increased sensitivity to stimulation by soluble BCMA and the potential for antigen-independent cytokine responses in T cells.

Figure 3:
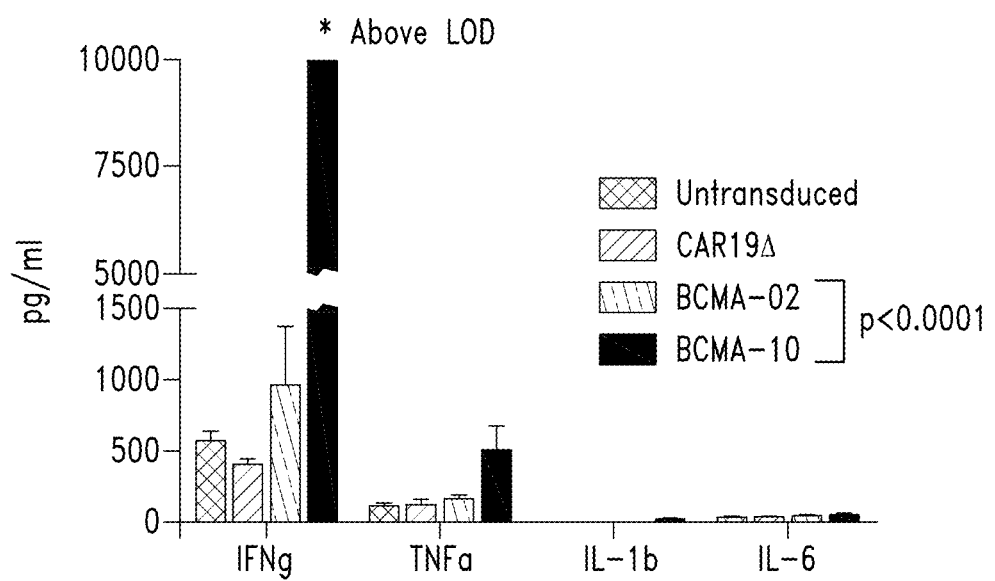
FIG. 3 shows the amount of inflammatory cytokines in growth media from untransduced control T cells, anti-BCMA02 CAR T cells, anti-BCMA10 CART cells, and CAR19Δ T cells, stimulated 10 days prior to the assay.
Figure 4:
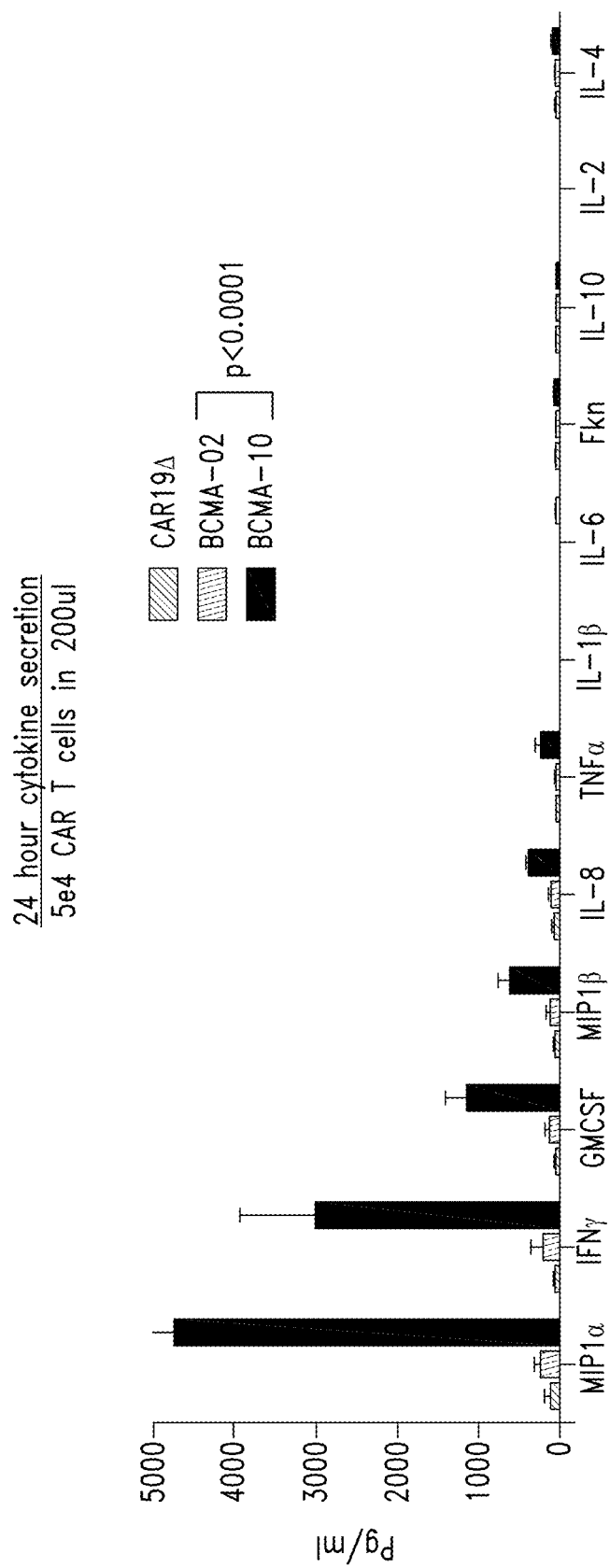
FIG. 4 shows the amount of inflammatory cytokines produced by anti-BCMA02 CAR T cells, anti-BCMA10 CART cells, and CAR19Δ T cells in the absence of antigen stimulation.

The potential of tonic cytokine secretion from anti-BCMA02 CAR T cells, anti-BCMA10 CART cells (10 days from culture initiation), and CAR19Δ T cells was examined. After manufacture of CAR T cells, growth media from anti-BCMA02 CAR T cell, anti-BCMA10 CART cell, and CAR19Δ T cell cultures were analyzed for the presence of inflammatory cytokines. Despite the absence of antigen stimulation, anti-BCMA10 CAR T cell cultures contained greater than 10 ng/mL IFNγ compared to less than 1 ng/mL of IFNγ in anti-BCMA02 CAR T cell cultures (FIG. 3). Anti-BCMA10 CAR T cell cultures also contained significantly ($p<0.001$) more TNFα. To further quantify the amount of cytokine produced by anti-BCMA10 CAR T cells without antigen stimulation, cytokine release was measured from $5\times10^4$ CAR T cells during a 24 hour culture. anti-BCMA10 CAR T cells produced significantly higher amounts of inflammatory cytokines MIP1α, IFNγ, GMCSF, MIP1β, IL-8, and TNFα compared to anti-BCMA02 CAR T cells (FIG. 4, $p<0.0001$). MIP1α and IFNγ concentrations were the highest among all cytokines examined. Anti-BCMA10 CAR T cells produced 4.7 ng MIP1α/$5\times10^4$ cells/24 hours, 3.0 ng IFNγ/$5\times10^4$ cells/24 hours and ~1 ng/$5\times10^4$ cells/24 hours or less of the other cytokines. No significant differences in the anti-inflammatory cytokines IL-10, IL-2, and IL-4 were detected.

Figure 5:
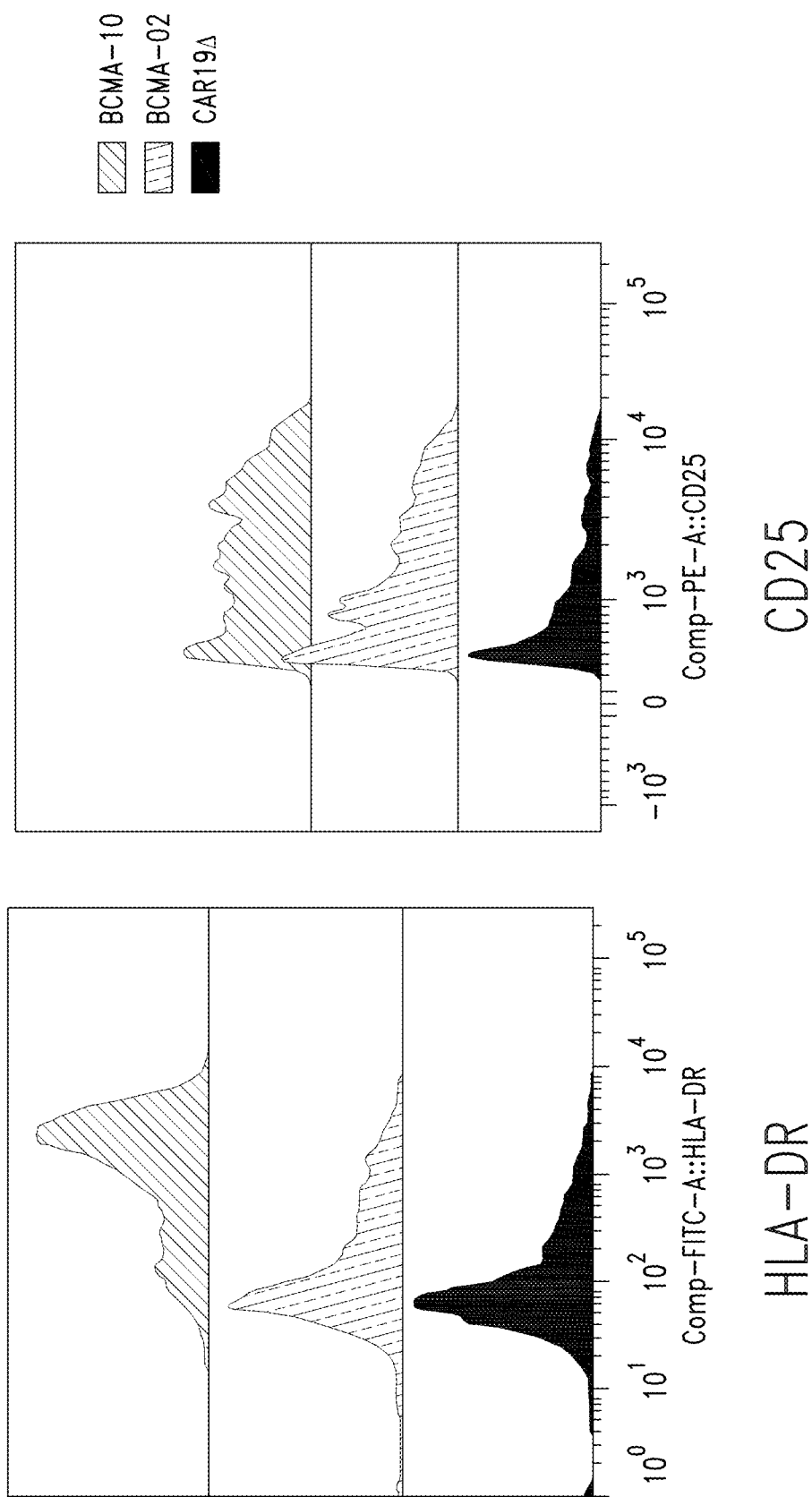
FIG. 5 shows the expression of phenotypic markers of activation at the end of anti-BCMA CAR T cell manufacturing. HLA-DR and CD25 expression was measured in anti-BCMA02 CAR T cells, anti-BCMA10 CAR T cells, and CAR19Δ T cells.

The expression of phenotypic markers of T cell activation at the end of anti-BCMA10 CAR T cell manufacturing were measure to examine whether tonic inflammatory cytokine secretion was indicative of a hyperactive state in anti-BCMA10 CAR T cells. HLA-DR and CD25 are surface markers that normally exhibit peak expression 12-24 hours after T cell activation and then diminish with time. CAR T cells prepared from three normal donors showed that an average 40±2% of anti-BCMA02 CAR T cells expressed HLA-DR. The expression of HLA-DR in these cells was comparable to untransduced (43±2.3%) T cells and CAR19Δ (32±2.2%) control T cells. In contrast, 88±1.2% anti-BCMA10 CAR T cells expressed HLA-DR (FIG. 5). Expression of another activation marker CD25 was also higher on anti-BCMA10 CAR T cells compared to anti-BCMA02 CAR T cells (53±0.9% vs 35±2.4%). Therefore, anti-BCMA10 CAR T cells exhibited phenotypic characteristics of activated T cells in the absence of added antigens.

Figure 6:
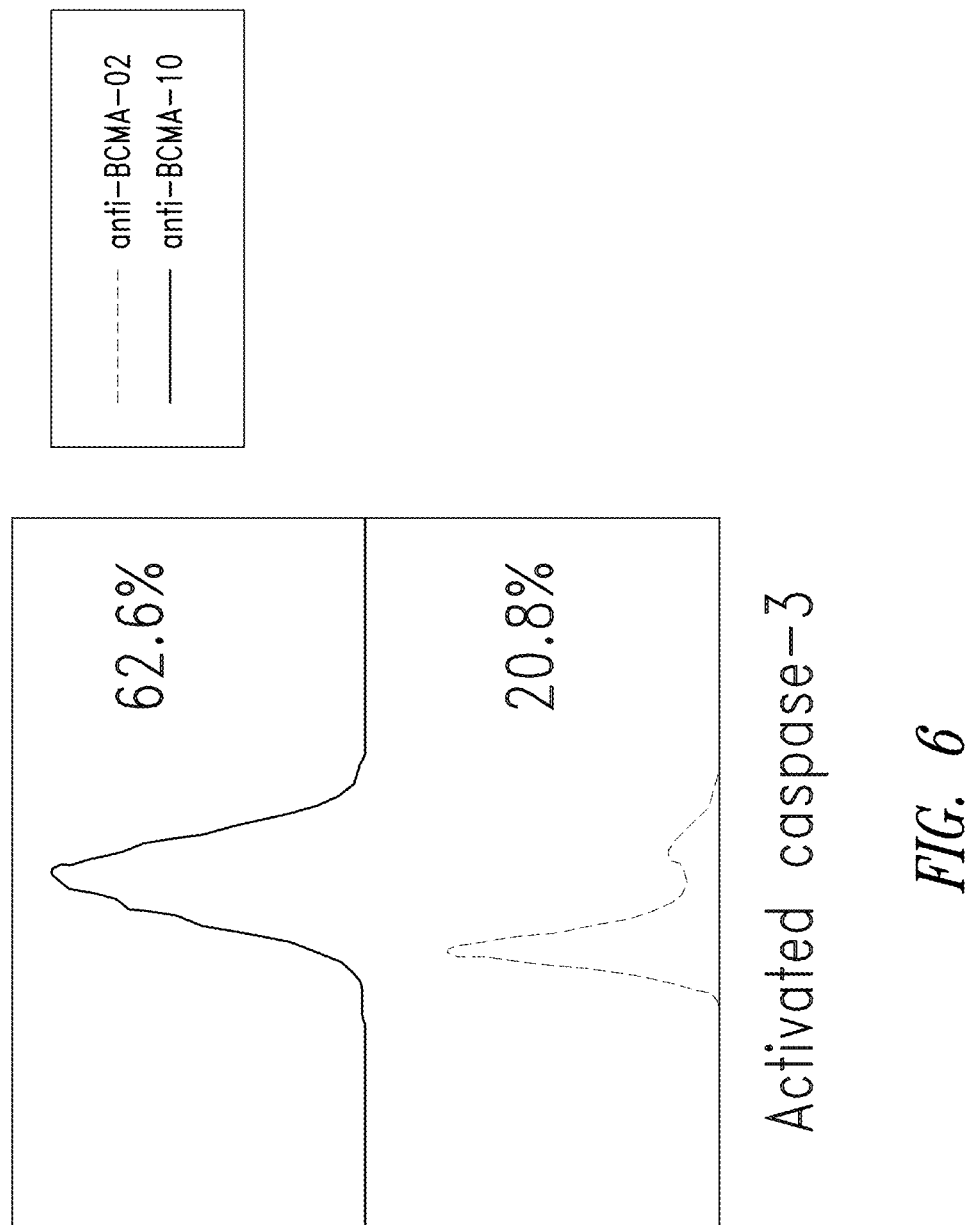
FIG. 6 shows the levels of activated caspase-3, a necessary step in apoptosis and important for AICD in anti-BCMA10 CAR T cells and anti-BCMA02 CAR T cells in the absence of antigen stimulation.
Figure 7:
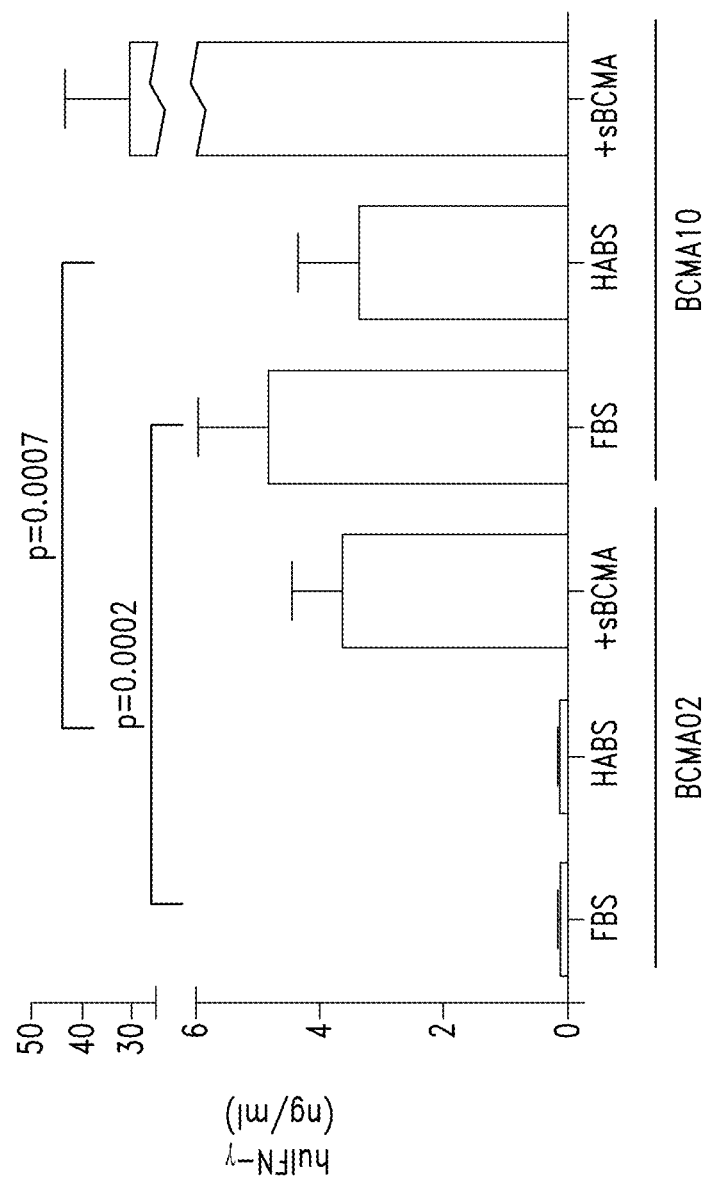
FIG. 7 shows the amount of inflammatory cytokine release in anti-BCMA02 and anti-BCMA10 CAR T cells in media containing fetal bovine serum (FBS), human AB serum (HABS), or 100 ng/ml soluble BCMA.

Hyperactivity in T cells is often associated with activation-induced cell death (AICD) by apoptosis. Levels of activated caspase-3 were measured to examine whether hyperactivity of anti-BCMA10 CAR T cells could result in higher apoptotic levels compared to anti-BCMA02 CAR T cells. 48% of anti-BCMA10 CAR T cells from two donors had active caspase-3 compared to 16% of anti-BCMA02 CAR T cells (FIG. 6). Thus, in the absence of added BCMA antigen, anti-BCMA10 CAR T cells contain a higher frequency of apoptotic cells associated with increased activation and inflammatory cytokine secretion compared to anti-BCMA02 CAR T cells. anti-BCMA02 CAR T cells and anti-BCMA10 CAR T cells were evaluated for whether the CAR T cells could selectively respond to low BCMA levels or be cross reactive to an unrelated antigen in the human serum used for T cell growth. T anti-BCMA02 CAR T cells and anti-BCMA10 CAR T cells were maintained in media lacking human serum for two days and then switched into media containing fetal bovine serum (FBS), human serum (HABS), or HABS in the presence or absence of 100 ng/mL soluble BCMA (FIG. 7). IFNγ release was assayed 24 hours later by ELISA. Both anti-BCMA02 CAR T cells and anti-BCMA10 CAR T cells responded to soluble BCMA. However, anti-BCMA10 CAR T cells secreted 10-times more IFNγ than anti-BCMA02 CAR T cells. In the absence of BCMA, only anti-BCMA10 CAR T cells released IFNγ regardless of culture in fetal bovine serum (FBS)($p=0.0002$) or human AB serum (HABS)($p=0.0007$). These data suggested that inflammatory cytokine secretion was intrinsic to anti-BCMA10 CAR T cells.

Figure 8A:
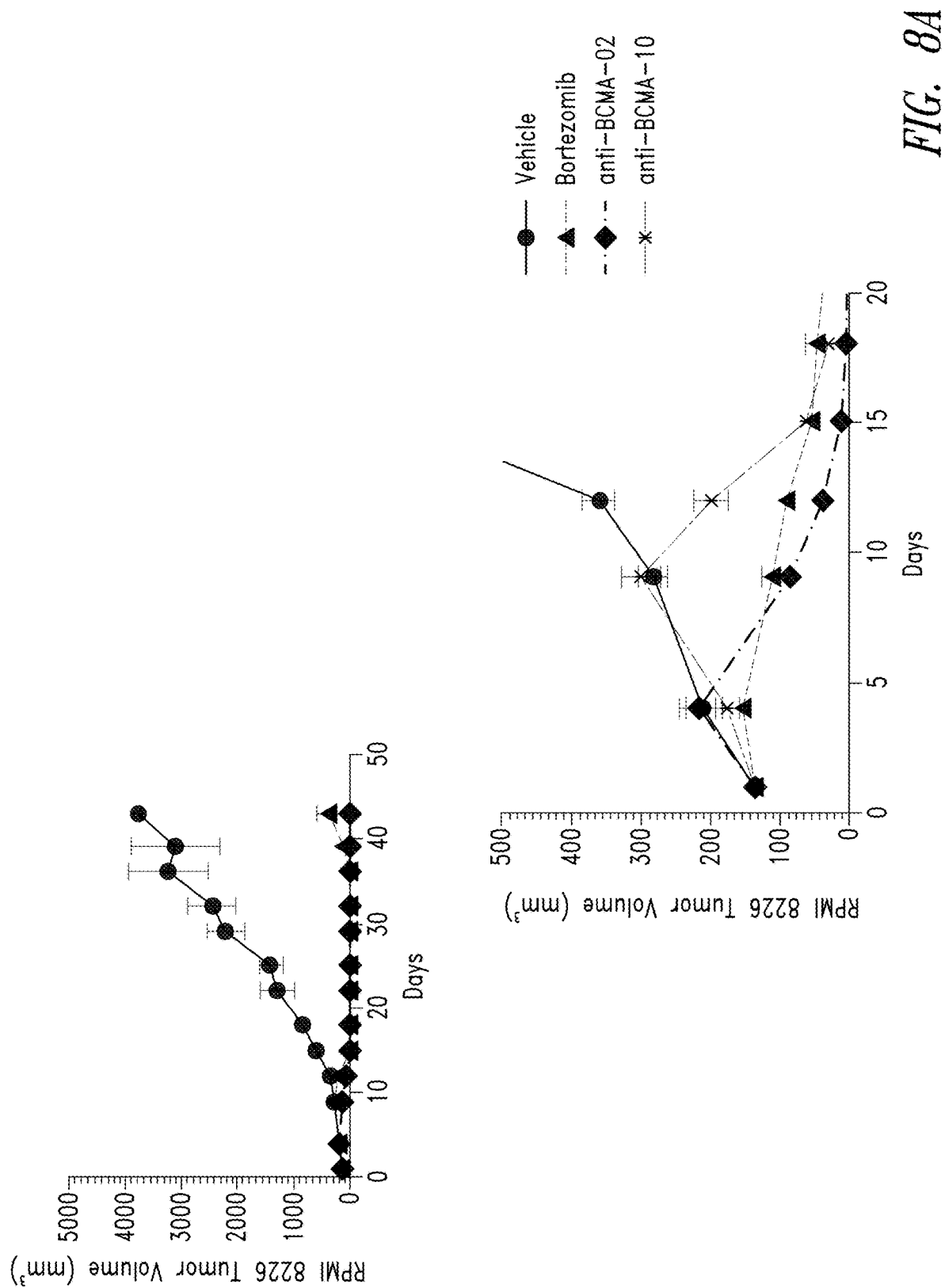
FIG. 8A shows the tumor volume in NOD scid gamma (NSG) mice with ~100 $mm^3$ experimental sub-cutaneous human multiple myeloma (RPMI-8226) tumors. Mice were treated with vehicle, $10^7$ anti-BCMA02 CAR T cells, $10^7$ anti-BCMA10 CAR T cells, or Bortezomib (velcade).
Figure 8B:
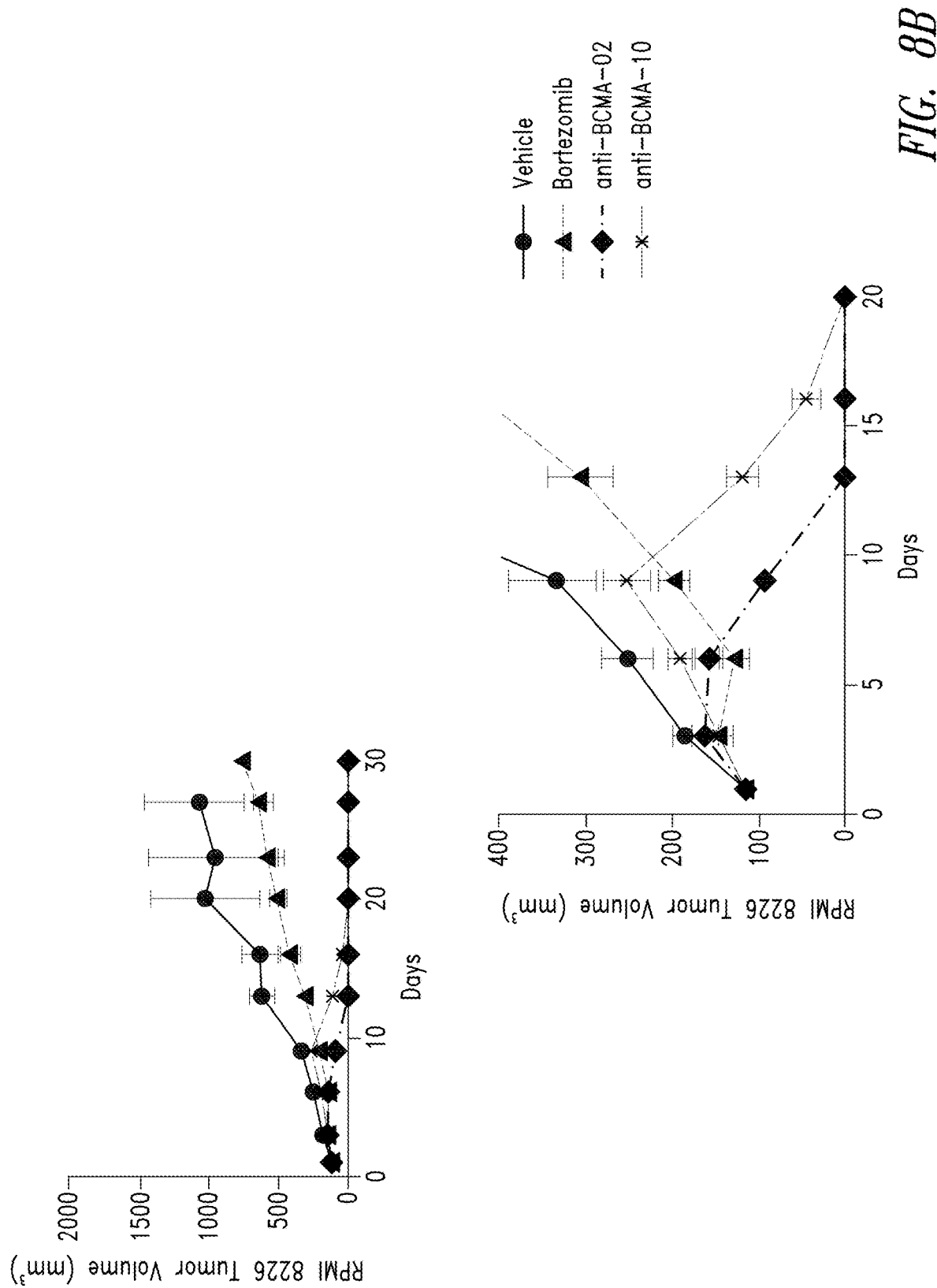
FIG. 8B shows the tumor volume in NOD scid gamma (NSG) mice with ~100 $mm^3$ experimental sub-cutaneous human multiple myeloma (RPMI-8226) tumors. Mice were treated with vehicle, $10^7$ anti-BCMA02 CAR T cells, $10^7$ anti-BCMA10 CAR T cells, or Bortezomib (velcade).

Inferior Anti-tumor Function of Anti-BCMA10 CAR T Cells in Mouse Model of Multiple Myeloma Hyperactivation and increased apoptosis could negatively impact CAR T cell persistence in patients and ultimately clinical efficacy. The anti-tumor function of anti-BCMA02 CAR T cells and anti-BCMA10 CAR T cells was examined in a mouse tumor model. NOD scid gamma (NSG) mice with ~100 mm³ experimental sub-cutaneous human multiple myeloma (RPMI-8226) tumors were treated with $10^7$ anti-BCMA02 CAR T cells, $10^7$ anti-BCMA10 CAR T cells, or Bortezomib (velcade). RPMI-8226 growth was monitored with calipers. In two independent experiments (FIGS. 8a and 8b), Bortezomib controlled tumor growth compared to vehicle control animals. Animals adoptively transferred with anti-BCMA02 CAR T cells exhibited rapid and durable tumor clearance (inset graphs magnify early tumor regressions). Adoptive transfer of anti-BCMA10 CAR T cells also caused tumor regressions but was delayed in both experiments compared to anti-BCMA02 CAR T cells.

CONCLUSIONS anti-BCMA02 CAR T cells and anti-BCMA10 CAR T cells exhibited comparable antitumor function in in vitro assays, but anti-BCMA10 CAR T cells had characteristics that could negatively impact safety and efficacy in patient treatment. Anti-BCMA10 CAR T cells responded robustly with inflammatory cytokine secretion after exposure to physiological levels of BCMA protein. Cytokine storm or cytokine release syndrome is a known clinical toxicity associated with CAR T cell therapies. Concerns over cytokine release to BCMA were worsened after observation of tonic activity of anti-BCMA10 CAR T cells. Even in the absence of antigen-stimulation, anti-BCMA10 CAR T cells released high levels of inflammatory cytokines. Persistent cytokine secretion has the potential to cause substantial clinical toxicities as well as negatively impact anti-tumor function. Indeed, we found higher composition of apoptotic cells and inferior anti-tumor function in anti-BCMA10 CAR T cells compared to anti-BCMA02 CAR T cell cultures in a mouse model of multiple myeloma.

REFERENCES

Avery et al., (2003). *BAFF selectively enhances the survival of plasmablasts generated from human memory B cells*. J Clin Invest, 112(2), 286-297.

Carpenito et al., (2009). *Control of large, established tumor xenografts with genetically retargeted human T cells containing CD28 and CD137 domains*. Proc Natl Acad Sci USA, 106(9), 3360-3365.

Chiu et al., (2007). *Hodgkin lymphoma cells express TACI and BCMA receptors and generate survival and proliferation signals in response to BAFF and APRIL*. Blood, 109(2), 729-739.

Sanchez et al. (2012). *Serum B-cell maturation antigen is elevated in multiple myeloma and correlates with disease status and survival*. Br J Haematol, 158(6), 727-738.

Example 3

Minimal BCMA Expression on Lymphomas Activates Anti-BCMA CAR T Cells

The level of BCMA expression on lymphoma and leukemia cell lines (Daudi and Raji) was measured in order to determine if the expression was sufficient to activate anti-BCMA02 CAR T cells.

BCMA expression on lymphoma, leukemia, and multiple myeloma cells was quantitated using flow cytometry. In this assay, the relative BCMA expression on the cells was assessed by correlating the fluorescence intensity of BCMA expression to a known number of bound antibodies (antibody binding capacity, ABC). BCMA expression levels in the lymphoma cell lines were compared to BCMA expression levels a multiple myeloma cell line (RPMI-8226) known to activate anti-BCMA02 CAR T cells. 12590±1275 BCMA02 molecules were expressed on the surface of RPMI-8226 cells. By contrast, Daudi cells expressed 1173±234 BCMA02 molecules and JeKo-1 cells (a Mantle cell lymphoma cell line) expressed only 222±138 BCMA02 molecules (FIG. 9, circles).

Figure 9:
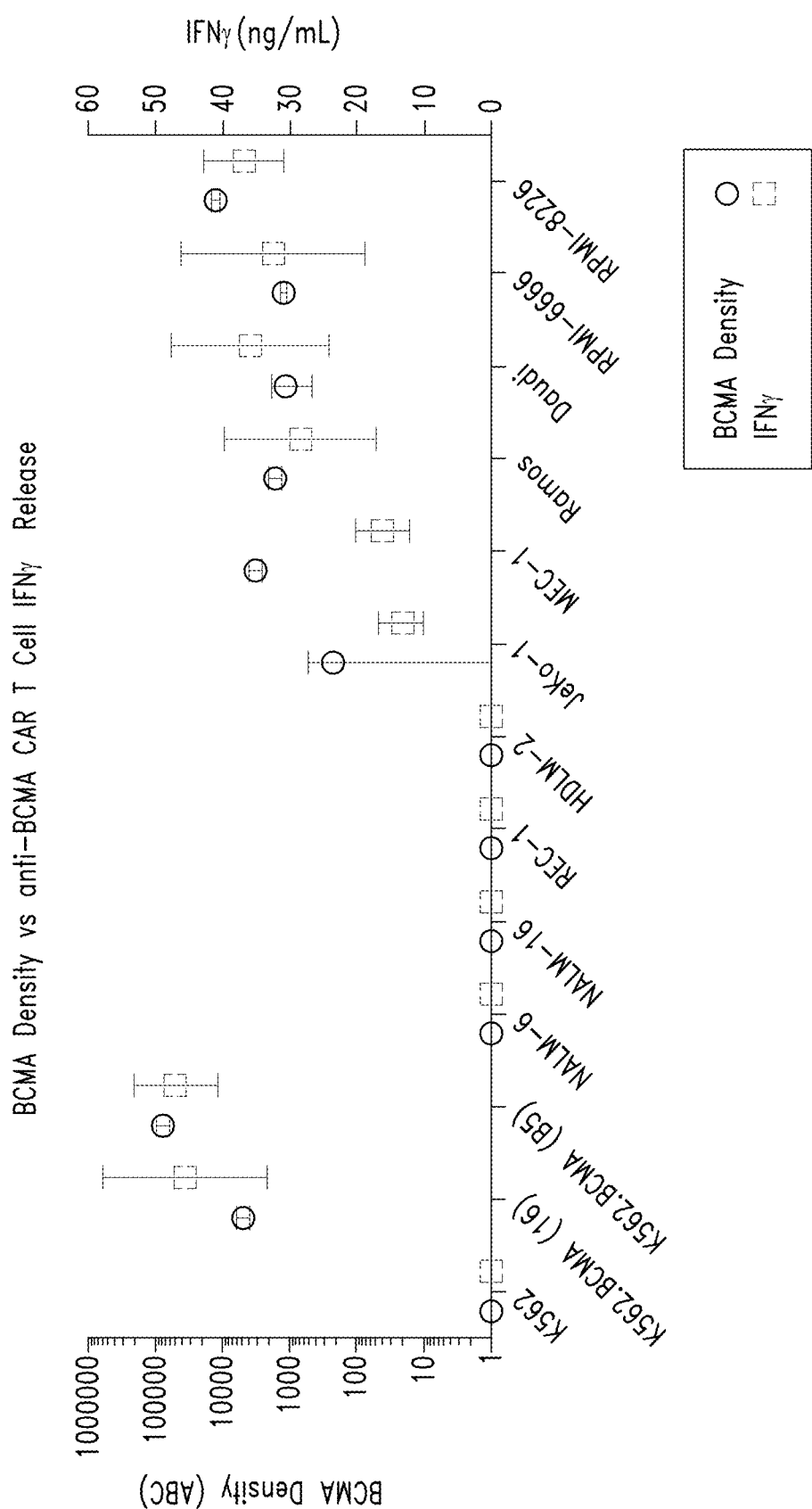
FIG. 9 shows the level of BCMA expression on lymphoma and leukemia cell lines (circles) and the activity of anti-BCMA CAR T cells to each cell line (IFNγ release, boxes). BCMA-negative (BCMA−) tumor cell lines: myelogenous leukemia (K562), acute lymphoblastic leukemia (NALM-6 and NALM-16); Mantle cell lymphoma (REC-1); or Hodgkin's lymphoma (HDLM-2) showed little or no IFNγ release. BCMA-positive (BCMA+) tumor cell lines: B cell chronic lymphoblastic leukemia (MEC-1), Mantle cell lymphoma (JeKo-1), Hodgkin's lymphoma (RPMI-6666), Burkitt's lymphoma (Daudi cells and Ramos cells), and multiple myeloma (RPMI-8226) showed substantial IFNγ release.

In another set of experiments the activity of anti-BCMA02 CAR T cells to the minute levels of BCMA observed on lymphoma and leukemia cell lines was tested (FIG. 9, boxes). Anti-BCMA02 CAR T cells were generated using standard methods and activity was assessed by IFNγ ELISA after co-culture with BCMA-positive and BCMA-negative tumor cell lines. Reactivity of anti-BCMA02 CAR T cells correlated with the relative amount of BCMA mRNA expression (above a threshold) and/or the density of the BCMA receptor on the surface of various tumor cell lines after co-culture (FIG. 9). Little, if any, IFNγ is released upon co-culture of BCMA CAR T cells with BCMA-negative (BCMA−) tumor cell lines: myelogenous leukemia (K562), acute lymphoblastic leukemia (NALM-6 and NALM-16); Mantle cell lymphoma (REC-1); or Hodgkin's lymphoma (HDLM-2). In contrast, substantial amounts of IFNγ was released upon co-culture of BCMA02 CAR T cells with BCMA-positive (BCMA+) tumor cell lines: B cell chronic lymphoblastic leukemia (MEC-1), Mantle cell lymphoma (JeKo-1), Hodgkin's lymphoma (RPMI-6666), Burkitt's lymphoma (Daudi cells and Ramos cells), and multiple myeloma (RPMI-8226).

Figure 10A:
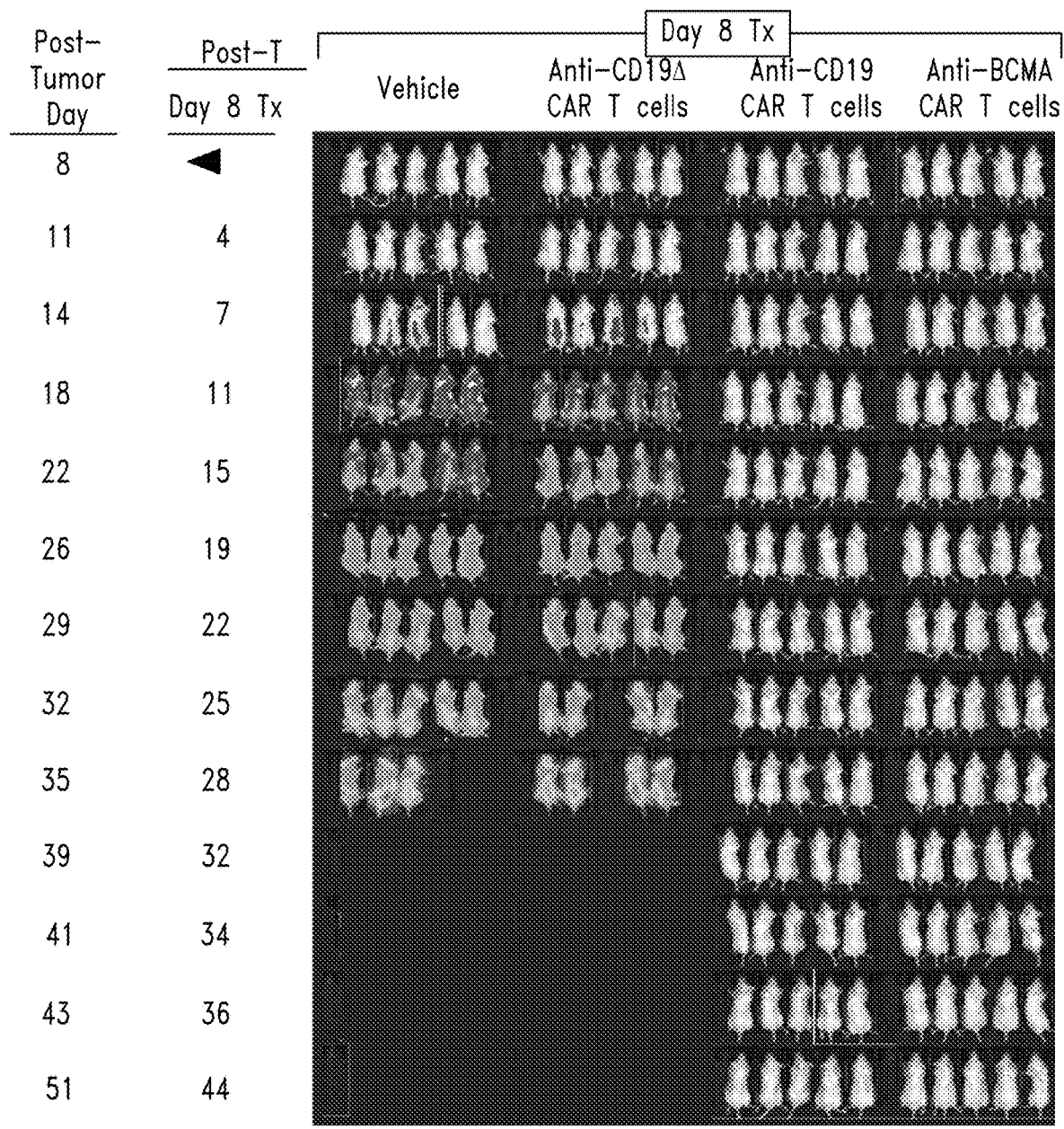
FIG. 10A shows the in vivo activity of vehicle, anti-CD19Δ CAR T cells, anti-CD19 CAR T cells, and anti-BCMA CAR T cells to BCMA expressing Burkitt's lymphoma cells (Daudi cells) in an NSG mouse model when CAR T cells are administered to the mice at 8 days post tumor induction.
Figure 10B:
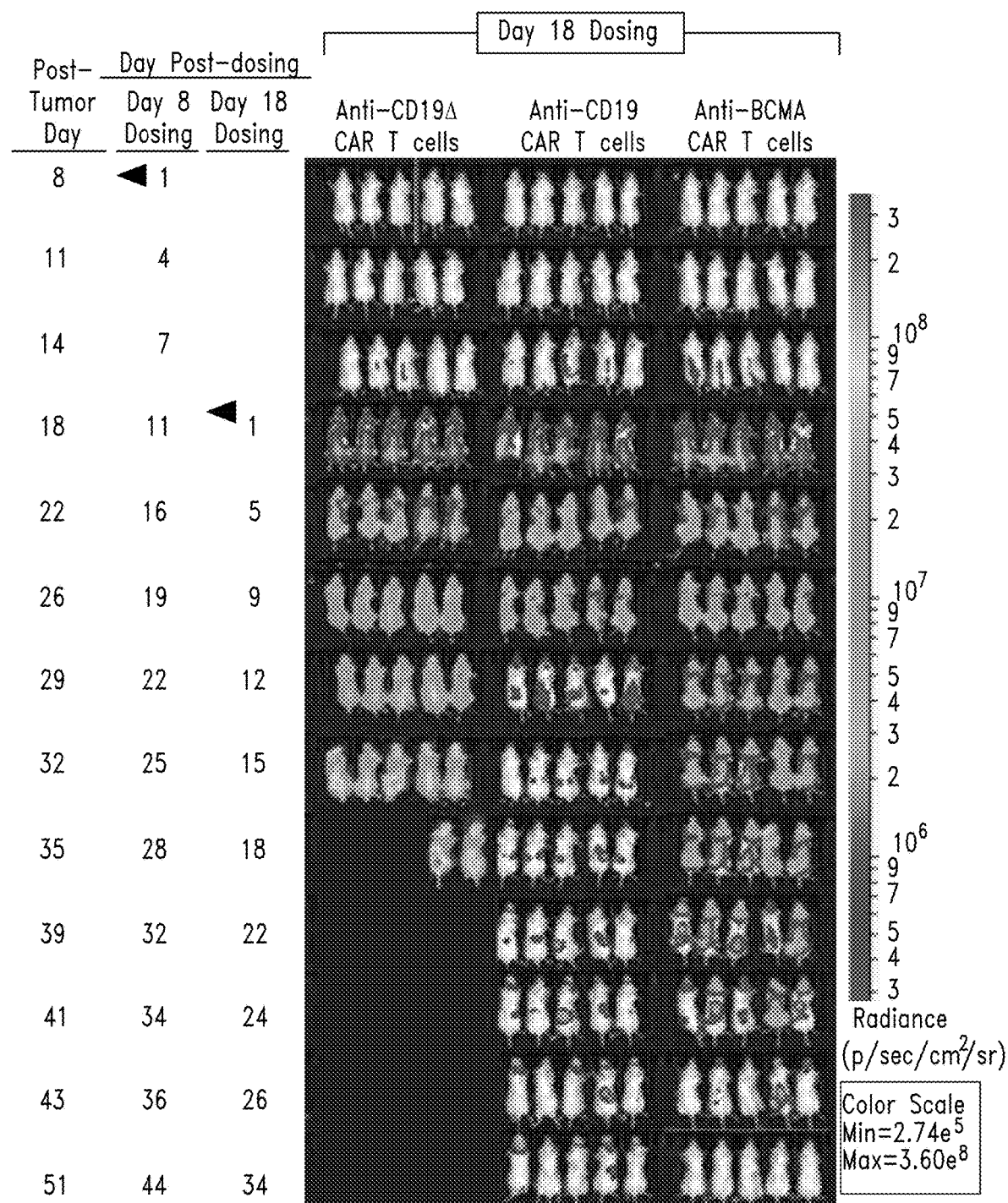
FIG. 10B shows the in vivo activity of vehicle, anti-CD19Δ CAR T cells, anti-CD19 CAR T cells, and anti-BCMA CAR T cells to BCMA expressing Burkitt's lymphoma cells (Daudi cells) in an NSG mouse model when CAR T cells are administered to the mice at 18 days post tumor induction.

The reactivity of anti-BCMA02 CAR T cells to BCMA expressing Burkitt's lymphoma cells (Daudi cells) extended to in vivo animal studies. Daudi cells also express CD19. The in vivo activity of anti-BCMA02 CAR T cells was compared to the in vivo activity of anti-CD19 CAR T cells. NOD scid gamma (NSG) mice were injected IV with $2 \times 10^6$ Daudi cells and allowed to accumulate a large systemic tumor burden before being treated with CAR T cells. CAR T cells were administered at 8 days and 18 days post-tumor induction (FIGS. 10A and 10B, respectively). The vehicle and negative control (anti-CD19Δ CAR T cells) failed to prevent tumor growth, as shown by log-phase increases in bioluminescence, resulting in weight loss and death (FIG. 10A, leftmost two mouse panels). Anti-CD19 and anti-BCMA02 CAR T cells prevented tumor growth, resulting in maintenance of body weight and survival. Anti-CD19 and anti-BCMA02 CAR T cells were equally effective when administered on Day 8 (FIG. 10A, rightmost two mouse panels). Anti-BCMA02 CAR T cells were also effective in decreasing tumor burden when administered at 18 days post-tumor induction. FIG. 10B, rightmost panel.

Example 4

Potent In Vitro Activity of Anti-BCMA CAR T Cells

Potent in vitro activity of anti-BCMA02 CAR T cells was achieved with a 50 percent reduction anti-BCMA02 CAR expression. T cell populations were transduced with between $4 \times 10^8$ and $5 \times 10^7$ transducing units of a lentivirus encoding an anti-BCM02A CAR molecule. The resulting T cell populations showed reduced anti-BCMA02 CAR T cell frequency (assayed as percent positive) and reduced expression of anti-BCMA02 CAR molecules (assayed as mean florescence intensity: MFI).

Figures 11A, 11B, 11C:
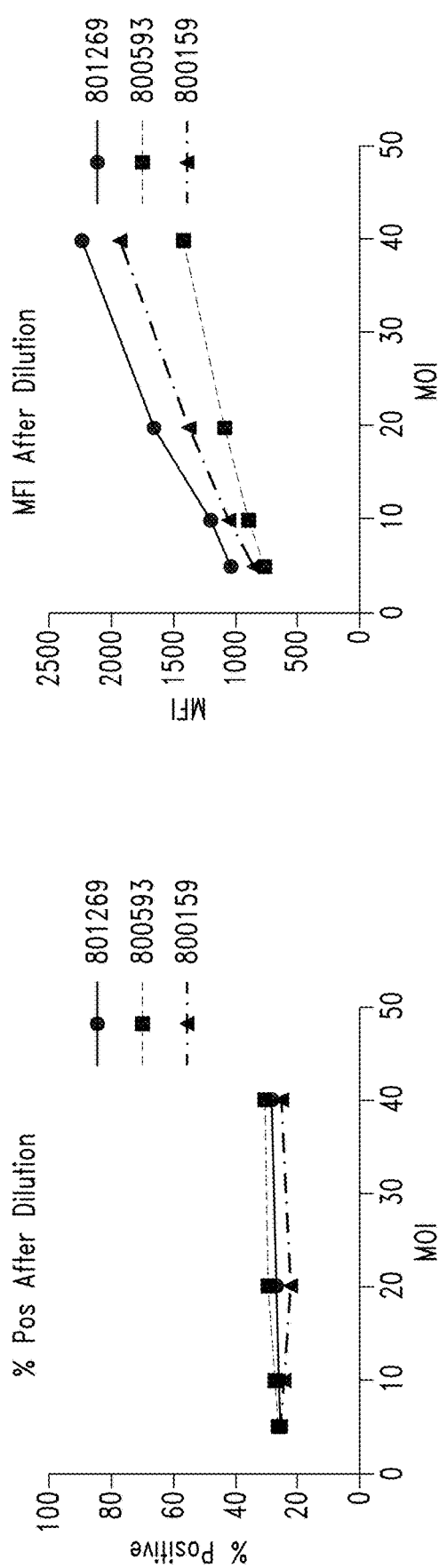
FIGS. 11A-C show potent in vitro activity of anti-BCMA CAR T cells achieved with a 50 percent reduction anti-BCMA CAR expression.

The impact of reduced CAR molecule expression on anti-BCMA02 activity was determined. The frequency of anti-BCMA CAR-positive T cells was normalized with untransduced T cells to contain 26±4% BCMA-reactive T cells (FIG. 11A). MFI of the normalized anti-BCMA02 CAR T cells ranged from 885 to 1875 (FIG. 11B). K562 is a CML cell line that lacks BCMA expression. K562 cells were engineered to express BCMA and were used in an in vitro cytolytic assay to assess activity of anti-BCMA02 CAR T cells with varied BCMA CAR expression (FIG. 11C). K562 cells were labeled with cell trace violet while K562 cells stably expressing BCMA (K562-BCMA) were labeled with CFSE. T cells, K562 cells, and K562-BCMA cells were harvested, washed, and resuspended in media lacking exogenous cytokines. Cells were cultured at a 20:1 or 10:1 effector (E; T cell) to target (T; 1:1 mix of K562 and K562 BCMA cells) ratio for 4 h in a 37° C., 5% C02 incubator. Cells were then stained with Live/Dead and analyzed by FACS. Cytotoxicity was determined by the difference in the ratio of K562:K562-BCMA cells normalized to conditions lacking T cells.

Example 5

Anti-BCMA CAR T Cell Manufacturing Process

Figure 12A:
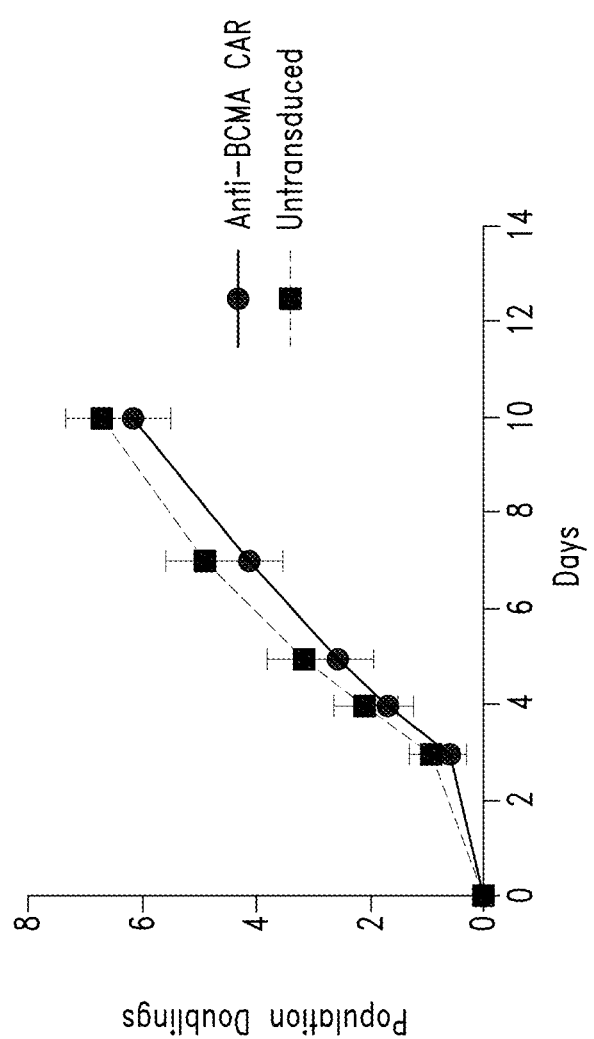
FIGS. 12A-D show the reliability of the manufacturing process for anti-BCMA CAR T cells.

Unique anti-BCMA02 CAR T cell products are manufactured for each patient treatment. The reliability of the manufacturing process for anti-BCMA02 CAR T cell products was evaluated by generating anti-BCMA02 CAR T cells from 11 individual normal donor PBMC. Anti-BCMA02 CAR T cell expansion from each donor was comparable to a matched untransduced culture performed in parallel (FIG. 12A).

Figure 12B:
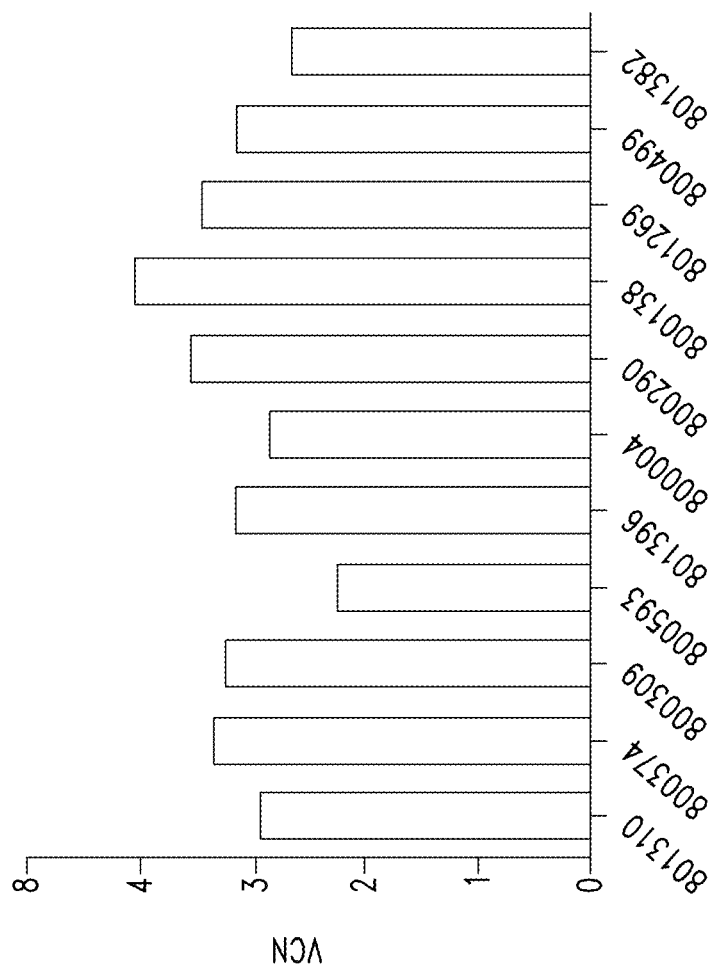
Figure 12C:
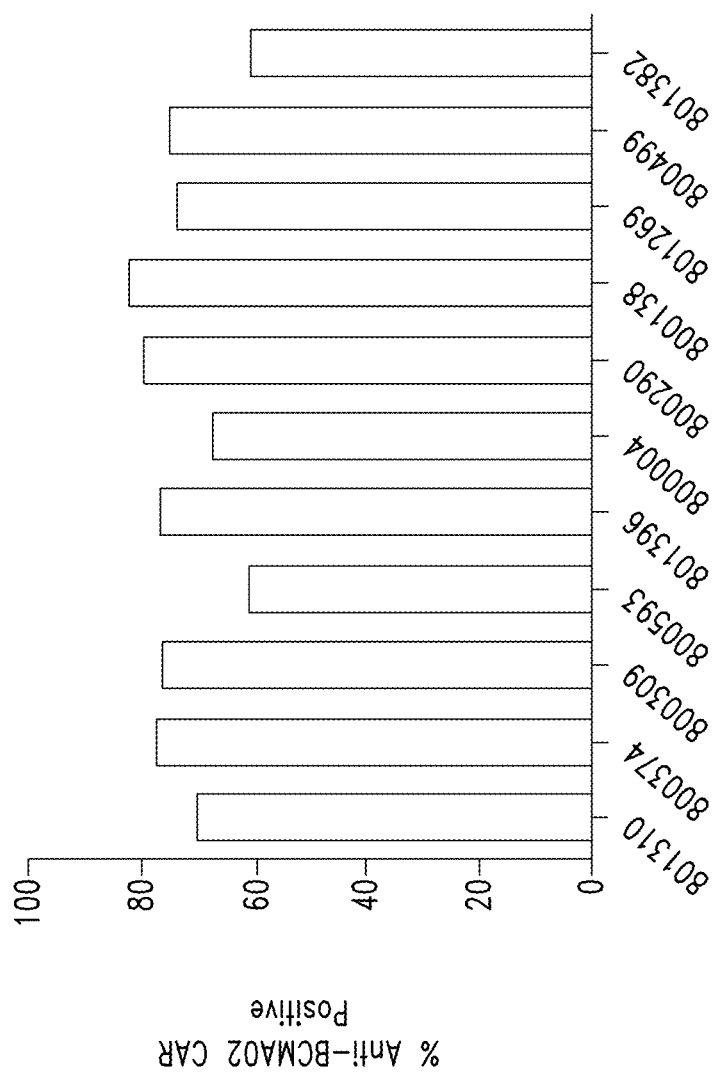

At the end of the culture period (day 10), T cell transduction efficiency was assessed by quantitating the number of integrated lentiviruses with qPCR and lentiviral-specific primer sets (vector copy number, VCN). Anti-BCMA02 CAR T cell cultures from the 11 donors showed comparable lentiviral transduction efficiency (FIG. 12B). The frequency of anti-BCMA02 CAR positive T cells was measured by flow cytometry and BCMA expression was found to be comparable across all donors (FIG. 12C).

Figure 12D:
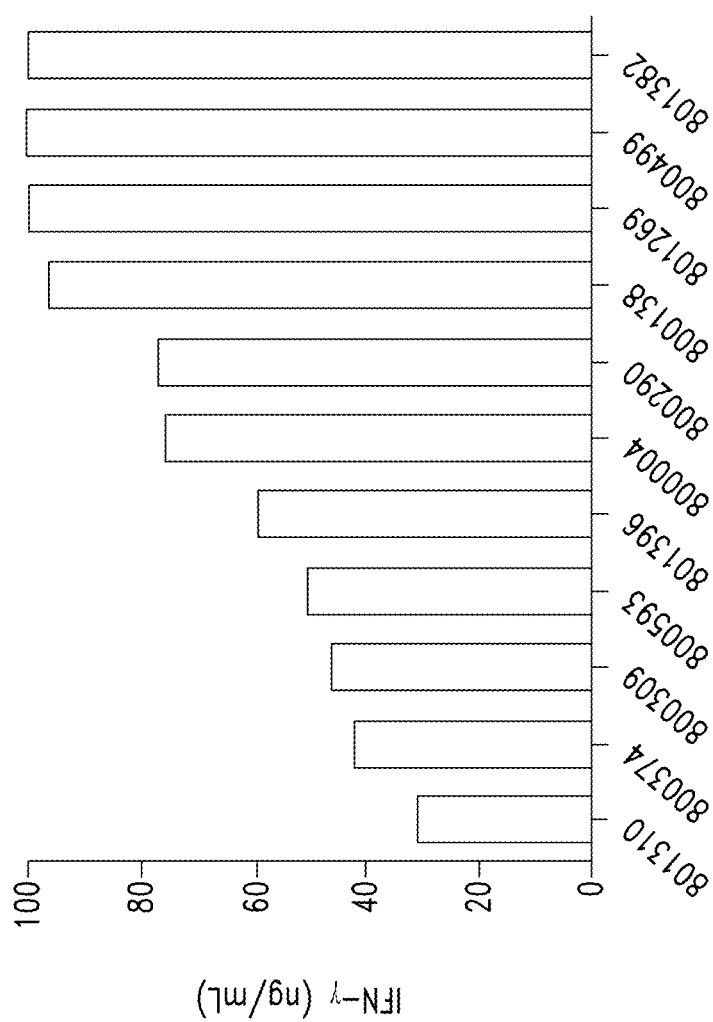

The activity of each anti-BCMA02 CAR T cell product was assessed by IFNγ-release after co-culture with K562 cells engineered to express BCMA. All anti-BCMA CAR02 T cell products exhibited therapeutically relevant levels of IFNγ release when exposed to BCMA-expressing K562 cells (FIG. 12D).

Example 6

CD62L, CD127, CD197, and CD38 Expression on CAR T Cells Treated with IL-2 or IL-2 and ZSTK474

Figure 13:
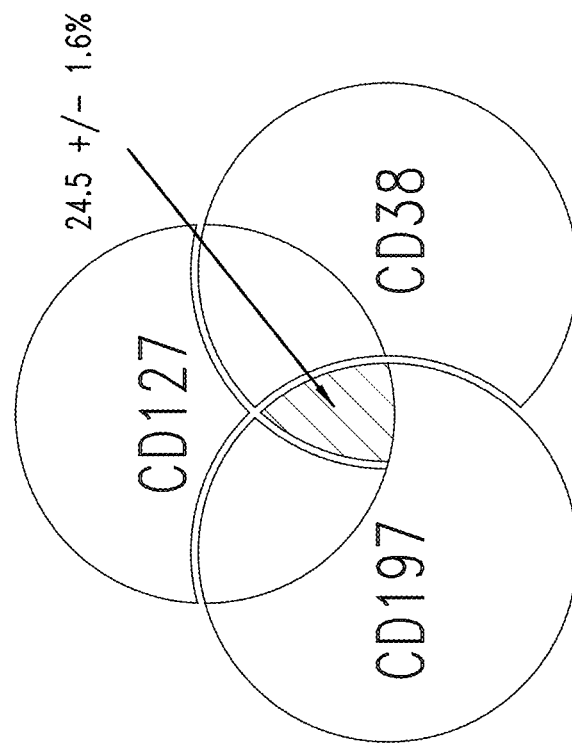
FIG. 13 shows Venn diagrams for co-expression of CD127, CD197 and CD38 in CD62L positive anti-BCMA02 T cells that have been cultured in the presence of IL-2 or IL-2 and ZSTK474 for ten days. ZSTK474-treated anti-BCMA02 CAR T cells showed an increase in the percentage of cells co-expressing CD127, CD197 and CD38 compared to anti-BCMA CAR T cells cultured with IL-2 alone.
Figure 13:
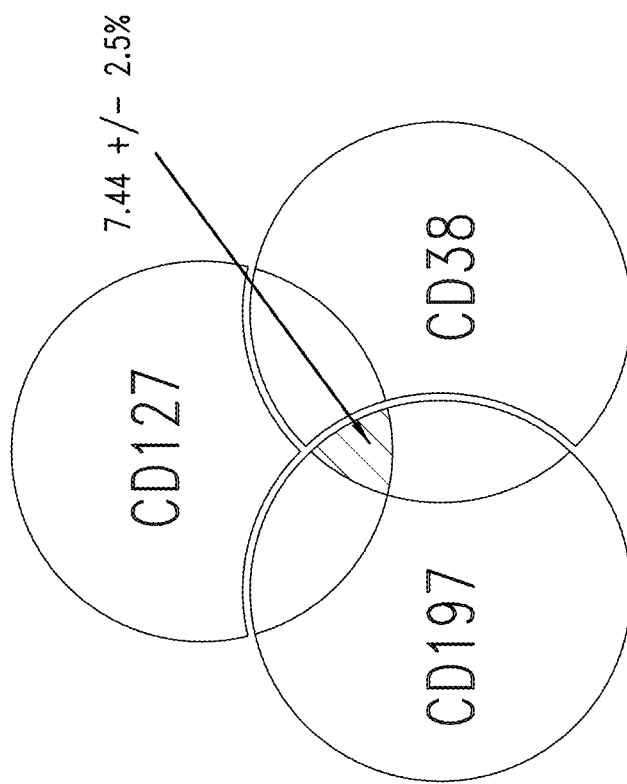

CAR T cells cultured with IL-2 and ZSTK474 show increased CD62L expression compared to CAR T cells cultured with IL-2 alone. Expression analysis of 29 additional cell surface markers on anti-BCMA02 CAR T cells cultured with IL-2 and ZSTK474 was performed using multiparameter mass cytometry (CyTOF) and compared with CAR T cells cultured in IL-2 alone. Three additional markers (CD127, CD197, and CD38) showed increased expression in the IL-2+ZSTK474 treated CAR T cells compared to CAR T cells treated with IL-2 alone. Thus, co-expression of CD62L, CD127, CD197, and CD38 further stratified ZSTK474-cultured CAR T cells. After culture in media containing IL-2, 7.44% of anti-BCMA02 CAR T co-expressed CD127, CD197 and CD38 compared to 24.5% of anti-BCMA02 CAR T cells cultured with IL-2 and ZSTK474. The Venn diagram in FIG. 13 illustrates the co-expression of CD127, CD197 and CD38 in CD62L positive anti-BCMA02 T cells.

Example 7

ZSTK474 Treatment Increases the Frequency of CD8 T Cells

Figure 14:
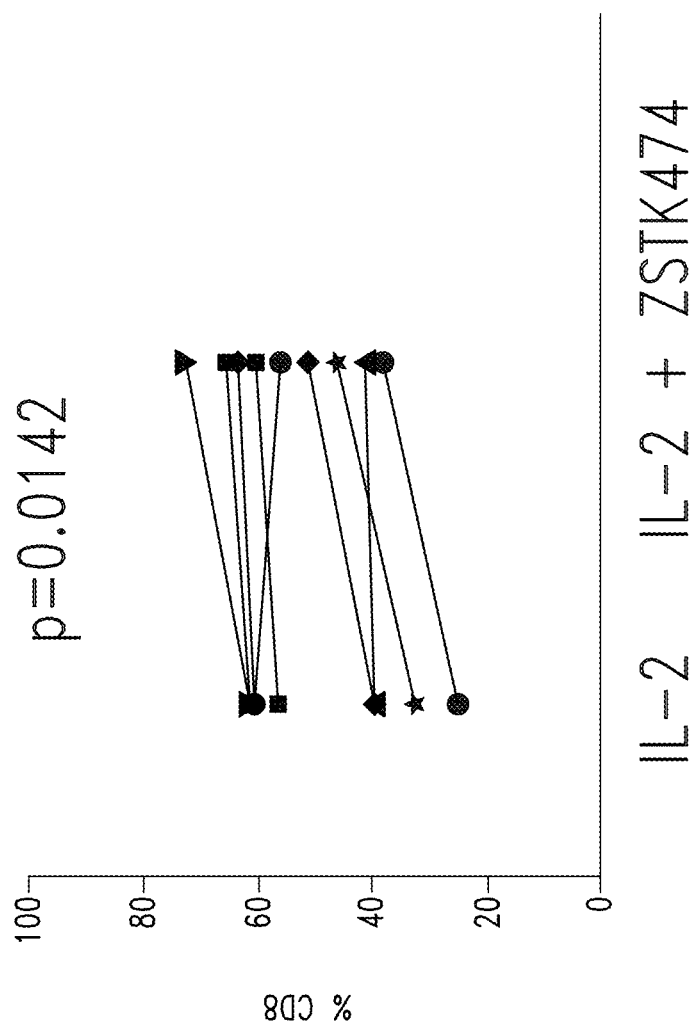
FIG. 14 shows an increased percentage of CD8 expressing anti-BCMA02 CAR T cells in cultures treated IL-2 and ZSTK474 (n=7) compared to cultures treated with IL-2 alone. CD8 expression was determined using a fluorescently-labeled anti-CD8 antibody and flow cytometry.

CD8 expression was quantified in anti-BCMA02 CAR T cells treated with IL-2 alone or IL-2 and ZSTK474. CD8 expression was determined using a fluorescently-labeled anti-CD8 antibody and flow cytometry. Anti-BCMA02 CAR T cells from seven normal donors cultured with IL-2 and ZSTK474 had significantly higher CD8 expression compared to anti-BCMA02 CAR T cells cultured with IL-2 alone. FIG. 14.

Example 8

Lack of Antigen-Independent Activity in ZSTK474 Treated Anti-BCMA CAR T Cells Tonic activity of CAR T cells in the absence of antigen has been associated with reduced biological activity. Tonic activity of anti-BCMA02 CAR T cells was assessed by quantifying interferon-γ (IFN-γ) release in the absence of antigen after culture in the presence of IL-2 and ZSTK474 compared to standard culture conditions with IL-2 alone. Anti-BCMA CAR T cells cultures were prepared using a system directly scalable to large clinical manufacturing processes. Briefly, peripheral blood mononuclear cells (PBMC) were cultured in static flasks in media containing IL-2 (CellGenix) and antibodies specific for CD3 and CD28 (Miltenyi Biotec). $2 \times 10^8$ transducing units of lentivirus encoding anti-BCMA CARs were added one day after culture initiation.

Figure 15:
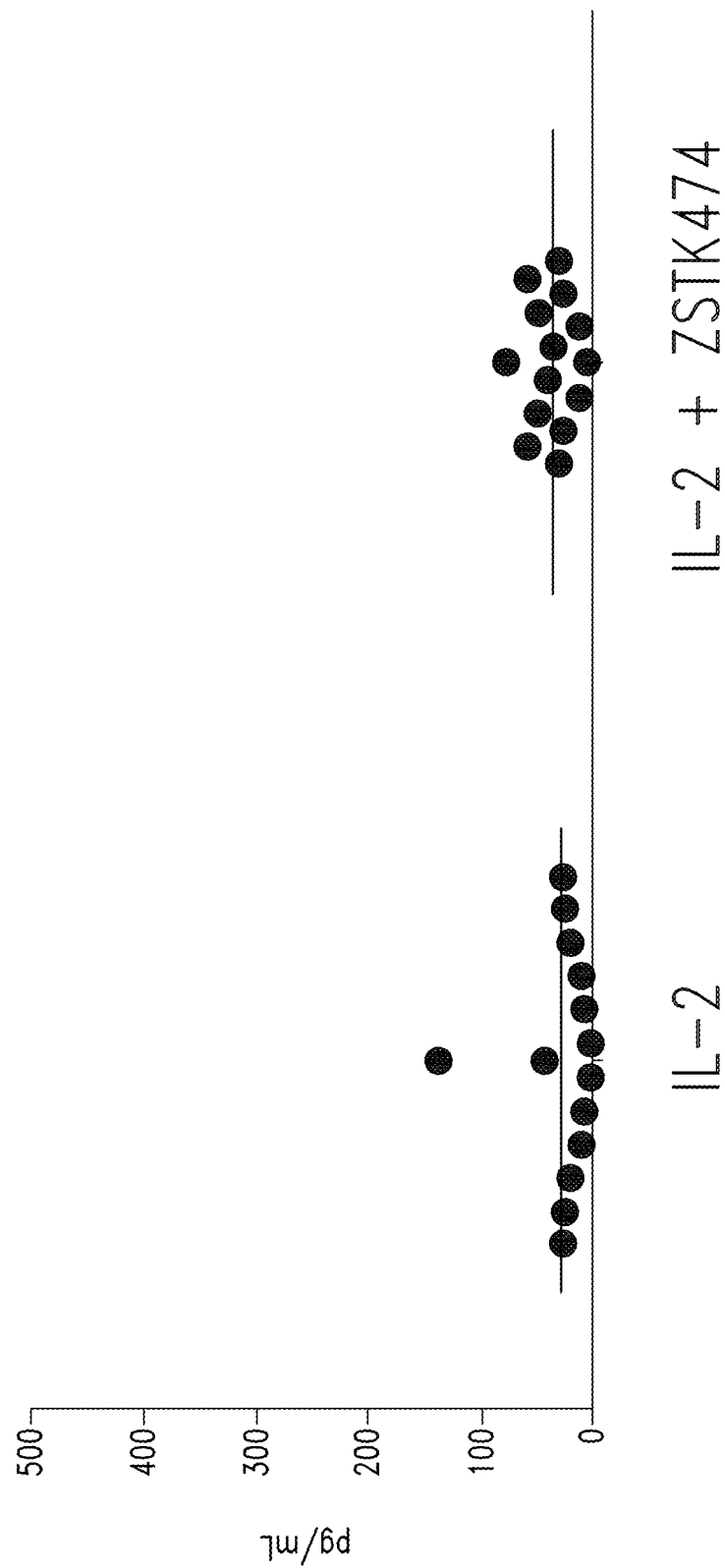
FIG. 15 shows the amount of IFN-γ released by anti-BCMA02 CAR T cells from 14 donors after culture with IL-2 alone or with IL-2 and ZSTK474. At the end of the culture period, an equivalent number of anti-BCMA02 CAR T cells were re-cultured for 24 hours in media alone. The amount of IFN-γ released in 24 hours was quantified by ELISA. Culture in ZSTK474 did not significantly increase anti-BCMA02 CAR T cell tonic cytokine release compared to anti-BCMA02 CAR T cells cultured with IL-2 alone.

Anti-BCMA02 CAR T cells were maintained in log-phase by adding fresh media containing IL-2 and an optimized dose of ZSTK474 for a total of ten days of culture. At the end of manufacture, an equivalent number of anti-BCMA02 CAR T cells were re-cultured for 24 hours in media alone. The amount of IFN-γ released in 24 hours was quantified by ELISA. In this assay IFN-γ levels below 200 pg/mL represent no tonic activity. FIG. 15 shows the amount of IFN-γ released by anti-BCMA02 CAR T cells from 14 donors is consistent with lacking tonic activity whether or not the CAR T cells are cultured with ZSTK474.

Example 9

ZSTK474 Treated Anti-BCMA02 CAR T Cells Show Therapeutic Activity in a Lymphoma Tumor Model Daudi tumors were used to interrogate the anti-tumor activity of anti-BCMA02 CAR T cells cultured with IL-2 or IL-2 and ZSTK474. Daudi cells express a low level of BCMA protein and provide an aggressive and difficult to treat lymphoma tumor model.

$2 \times 10^6$ Daudi tumor cells were labeled with a firefly luciferase gene and injected into NOD scid IL-2 receptor gamma chain knockout mice (NSG) by intravenous injection. After tumors were allowed to form, $1 \times 10^7$ CAR T cells were injected in to tumor bearing mice. Mice were injected with i) anti-BCMA02 CAR T cells treated for ten days with IL-2 or IL-2 and ZSTK474; or ii) a truncated signaling deficient anti-BCMA02 (tBCMA02) CAR T cell treated for ten days with IL-2 and ZSTK474. Tumor growth was monitored by bioluminescence using a Xenogen-IVIS Imaging system.

Figure 16:
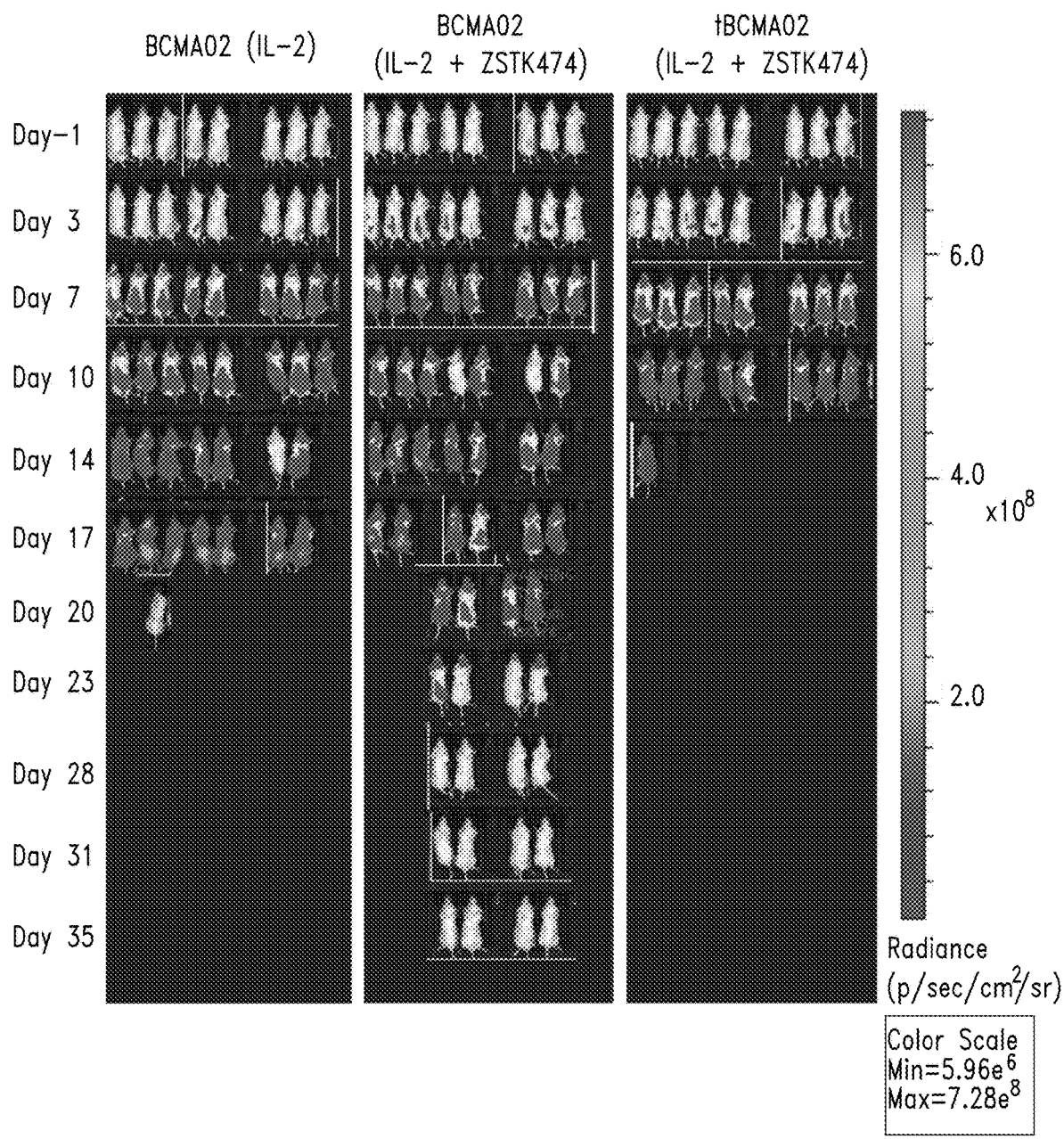
FIG. 16 shows anti-tumor activity of anti-BCMA02 CAR T cells treated with IL-2, or IL-2 and ZSTK474, or a truncated signaling deficient anti-BCMA02 (tBCMA02) CAR T cell treated with IL-2 and ZSTK474 in an aggressive Daudi tumor model. Complete tumor regression was observed in 50% of mice administered the anti-BCMA02 CAR T cells treated with IL-2 and ZSTK474.

Complete tumor regression was observed in 50% of mice administered the anti-BCMA02 CAR T cells treated with IL-2 and ZSTK474. FIG. 16.

Example 10

ZSTK474 Treated CAR T Cells Show Therapeutic Activity in a Mouse Model of Human Myeloma Animals with 100 mm³ sub cutaneous multiple myeloma tumors (RPMI-8226) were infused with equivalent CAR T cell doses ($1 \times 10^6$ anti-BCMA02 CAR-positive T cells) or unmodified T cells from a matched T cell donor (untransduced). Anti-BCMA CAR T cells were treated with IL-2 or IL-2 and ZSTK474 as described in Example 8.

Figure 17:
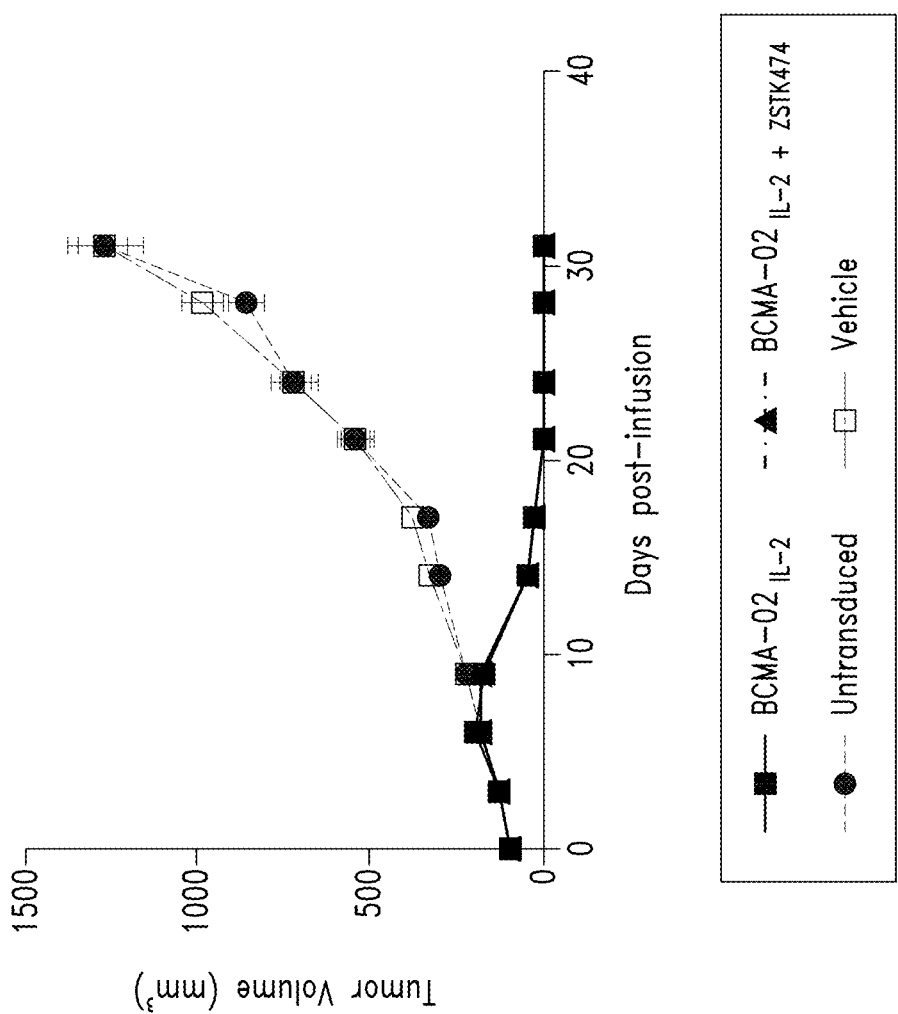
FIG. 17 shows anti-tumor activity of anti-BCMA02 CAR T cells treated with IL-2, or IL-2 and ZSTK474 in a multiple myeloma tumor (RPMI-8226) model. Animals treated with IL-2- or IL-2 and ZSTK474-cultured anti-BCMA02 CAR T cells completely prevented tumor outgrowth.

Animals treated with IL-2- or IL-2 and ZSTK474-cultured anti-BCMA02 CAR T cells completely prevented tumor outgrowth. FIG. 17. In contrast, animals treated with untransduced or vehicle were unable to control tumor growth. FIG. 17.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A population of cells comprising T cells, wherein the T cells comprise a lentiviral vector comprising a left (5') lentiviral LTR; a Psi (Ψ) packaging signal; a central polypurine tract/DNA flap (cPPT/FLAP); a retroviral export element; a promoter operably linked to a polynucleotide sequence encoding a chimeric antigen receptor (CAR), wherein the polynucleotide sequence is set forth in SEQ ID NO: 10; and a right (3') lentiviral LTR.

2. The population of cells of claim 1, wherein the lentiviral vector is selected from the group consisting essentially of: human immunodeficiency virus 1 (HIV-1); human immunodeficiency virus 2 (HIV-2); visna-maedi virus (VMV) virus; caprine arthritis-encephalitis virus (CAEV); equine infectious anemia virus (EIAV); feline immunodeficiency virus (FIV); bovine immune deficiency virus (BIV); and simian immunodeficiency virus (SIV).

3. The population of cells of claim 1, wherein the lentiviral vector further comprises a heterologous polyadenylation sequence.

4. The population of cells of claim 3, wherein the heterologous polyadenylation sequence is a bovine growth hormone polyadenylation signal or a rabbit β-globin polyadenylation sequence.

5. The vector of claim 1, wherein the promoter of the 5' LTR is replaced with a heterologous promoter.

6. The population of cells of claim 5, wherein the heterologous promoter is a cytomegalovirus (CMV) promoter, a Rous Sarcoma Virus (RSV) promoter, or a Simian Virus 40 (SV40) promoter.

7. The population of cells of claim 1, wherein the 3' LTR comprises one or more modifications.

8. The population of cells of claim 1, wherein the 3' LTR comprises one or more deletions.

9. The population of cells of claim 1, wherein the 3' LTR is a self-inactivating (SIN) LTR.

10. The population of cells of claim 1, wherein the promoter operably linked to the polynucleotide sequence encoding the CAR is selected from the group consisting of: a cytomegalovirus immediate early gene promoter (CMV), an elongation factor 1 alpha promoter (EF1-α), a phosphoglycerate kinase-1 promoter (PGK), a ubiquitin-C promoter (UBQ-C), a cytomegalovirus enhancer/chicken beta-actin promoter (CAG), polyoma enhancer/herpes simplex thymidine kinase promoter (MC1), a beta actin promoter (β-ACT), a simian virus 40 promoter (SV40), and a myeloproliferative sarcoma virus enhancer, negative control region deleted, d1587rev primer-binding site substituted (MND) promoter.

11. A composition comprising the population of cells of claim 1 and a physiologically acceptable excipient.

12. A population of cells comprising immune effector cells, wherein the immune effector cells comprise a lentiviral vector, wherein the lentiviral vector comprises a left (5') lentiviral LTR wherein the promoter of the 5' LTR is replaced with a CMV promoter; a Psi (Ψ) packaging signal; a cPPT/FLAP; a Rev response element (RRE); a myeloproliferative sarcoma virus enhancer, negative control region deleted, d1587rev primer-binding site substituted (MND) promoter operably linked to a polynucleotide sequence encoding a CAR, wherein the polynucleotide sequence is set forth in SEQ ID NO: 10; a right (3') lentiviral self-inactivating (SIN) LTR; and a heterologous polyadenylation sequence.

13. A composition comprising the population of cells of claim 12 and a physiologically acceptable excipient.

14. The population of cells of claim 12, wherein the immune effector cells comprise T cells or natural killer (NK) cells.

15. A composition comprising the population of cells of claim 14 and a physiologically acceptable excipient.

16. The population of cells of claim 12, wherein the immune effector cells comprise T cells.

17. A composition comprising the population of cells of claim 16 and a physiologically acceptable excipient.

18. The population of cells of claim 12, wherein the immune effector cells comprise NK cells.

19. A composition comprising the population of cells of claim 18 and a physiologically acceptable excipient.

20. The population of cells of claim 12, wherein the immune effector cells comprise T cells and natural killer (NK) cells.

21. A composition comprising the population of cells of claim 20 and a physiologically acceptable excipient.

* * * * *

```
                        SEQUENCE LISTING

<160> NUMBER OF SEQ ID NOS: 36

<210> SEQ ID NO 1
<211> LENGTH: 15
<212> TYPE: PRT
<213> ORGANISM: Mus musculus

<400> SEQUENCE: 1

Arg Ala Ser Glu Ser Val Thr Ile Leu Gly Ser His Leu Ile His
1               5                   10                  15

<210> SEQ ID NO 2
<211> LENGTH: 7
<212> TYPE: PRT
<213> ORGANISM: mus musculus

<400> SEQUENCE: 2

Leu Ala Ser Asn Val Gln Thr
1               5

<210> SEQ ID NO 3
<211> LENGTH: 9
<212> TYPE: PRT
<213> ORGANISM: mus musculus

<400> SEQUENCE: 3

Leu Gln Ser Arg Thr Ile Pro Arg Thr
1               5

<210> SEQ ID NO 4
<211> LENGTH: 5
<212> TYPE: PRT
<213> ORGANISM: Mus musculus

<400> SEQUENCE: 4

Asp Tyr Ser Ile Asn
1               5

<210> SEQ ID NO 5
<211> LENGTH: 17
<212> TYPE: PRT
<213> ORGANISM: Mus musculus

<400> SEQUENCE: 5

Trp Ile Asn Thr Glu Thr Arg Glu Pro Ala Tyr Ala Tyr Asp Phe Arg
1               5                   10                  15

Gly

<210> SEQ ID NO 6
<211> LENGTH: 8
<212> TYPE: PRT
<213> ORGANISM: Mus musculus

<400> SEQUENCE: 6

Asp Tyr Ser Tyr Ala Met Asp Tyr
1               5
```

<210> SEQ ID NO 7
<211> LENGTH: 111
<212> TYPE: PRT
<213> ORGANISM: Mus musculus

<400> SEQUENCE: 7

Asp Ile Val Leu Thr Gln Ser Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110

<210> SEQ ID NO 8
<211> LENGTH: 117
<212> TYPE: PRT
<213> ORGANISM: Mus musculus

<400> SEQUENCE: 8

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser
        115

<210> SEQ ID NO 9
<211> LENGTH: 493
<212> TYPE: PRT
<213> ORGANISM: Artificial Sequence
<220> FEATURE:
<223> OTHER INFORMATION: anti-BCMA02 CAR

<400> SEQUENCE: 9

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Pro Ser Leu
            20                  25                  30

Ala Met Ser Leu Gly Lys Arg Ala Thr Ile Ser Cys Arg Ala Ser Glu 35                  40                  45
Ser Val Thr Ile Leu Gly Ser His Leu Ile His Trp Tyr Gln Gln Lys
 50                  55                  60

Pro Gly Gln Pro Pro Thr Leu Leu Ile Gln Leu Ala Ser Asn Val Gln
 65                  70                  75                  80

Thr Gly Val Pro Ala Arg Phe Ser Gly Ser Gly Ser Arg Thr Asp Phe
                 85                  90                  95

Thr Leu Thr Ile Asp Pro Val Glu Glu Asp Val Ala Val Tyr Tyr
            100                 105                 110

Cys Leu Gln Ser Arg Thr Ile Pro Arg Thr Phe Gly Gly Gly Thr Lys
            115                 120                 125

Leu Glu Ile Lys Gly Ser Thr Ser Gly Ser Gly Lys Pro Gly Ser Gly
130                 135                 140

Glu Gly Ser Thr Lys Gly Gln Ile Gln Leu Val Gln Ser Gly Pro Glu
145                 150                 155                 160

Leu Lys Lys Pro Gly Glu Thr Val Lys Ile Ser Cys Lys Ala Ser Gly
                165                 170                 175

Tyr Thr Phe Thr Asp Tyr Ser Ile Asn Trp Val Lys Arg Ala Pro Gly
            180                 185                 190

Lys Gly Leu Lys Trp Met Gly Trp Ile Asn Thr Glu Thr Arg Glu Pro
            195                 200                 205

Ala Tyr Ala Tyr Asp Phe Arg Gly Arg Phe Ala Phe Ser Leu Glu Thr
210                 215                 220

Ser Ala Ser Thr Ala Tyr Leu Gln Ile Asn Asn Leu Lys Tyr Glu Asp
225                 230                 235                 240

Thr Ala Thr Tyr Phe Cys Ala Leu Asp Tyr Ser Tyr Ala Met Asp Tyr
                245                 250                 255

Trp Gly Gln Gly Thr Ser Val Thr Val Ser Ser Ala Ala Ala Thr Thr
            260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
            355                 360                 365

Cys Arg Phe Pro Glu Glu Glu Glu Gly Gly Cys Glu Leu Arg Val Lys
            370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 10
<211> LENGTH: 1485
<212> TYPE: DNA
<213> ORGANISM: Artificial Sequence
<220> FEATURE:
<223> OTHER INFORMATION: anti-BCMA02 CAR

<400> SEQUENCE: 10

```
atggcactcc ccgtcaccgc ccttctcttg cccctcgccc tgctgctgca tgctgccagg      60
cccgacattg tgctcactca gtcacctccc agcctggcca tgagcctggg aaaaagggcc    120
accatctcct gtagagccag tgagtccgtc acaatcttgg ggagccatct tattcactgg    180
tatcagcaga agcccgggca gcctccaacc cttcttattc agctcgcgtc aaacgtccag    240
acgggtgtac ctgccagatt ttctggtagc gggtcccgca ctgattttac actgaccata    300
gatccagtgg aagaagacga tgtggccgtg tattattgtc tgcagagcag aacgattcct    360
cgcacatttg gtgggggtac taagctggag attaagggaa gcacgtccgg ctcaggaaag    420
ccgggctccg cgagggaag cacgaagggg caaattcagc tggtccagag cggacctgag    480
ctgaaaaaac ccggcgagac tgttaagatc agttgtaaag catctggcta ccttcacc     540
gactacagca taaattgggt gaaacgggcc cctggaaagg gcctcaaatg gatgggttgg    600
atcaataccg aaactaggga gcctgcttat gcatatgact ccgcgggag attcgccttt    660
tcactcgaga catctgcctc tactgcttac ctccaaataa acaacctcaa gtatgaagat    720
acagccactt acttttgcgc cctcgactat agttacgcca tggactactg gggacaggga    780
acctccgtta ccgtcagttc gcggccgca accacaacac ctgctccaag gcccccaca    840
cccgctccaa ctatagccag ccaaccattg agcctcagac ctgaagcttg caggcccgca    900
gcaggaggcg ccgtccatac gcgaggcctg acttcgcgt gtgatattta tatttgggcc    960
cctttggccg gaacatgtgg ggtgttgctt ctctcccttg tgatcactct gtattgtaag   1020
cgcgggagaa agaagctcct gtacatcttc aagcagcctt ttatgcgacc tgtgcaaacc   1080
actcaggaag aagatgggtg ttcatgccgc ttccccgagg aggaagaagg agggtgtgaa   1140
ctgagggtga aatttctag aagcgccgat gctcccgcat atcagcaggg tcagaatcag   1200
ctctacaatg aattgaatct cggcaggcga gaagagtacg atgttctgga caagagacgg   1260
ggcagggatc ccgagatggg gggaaagccc cggagaaaaa atcctcagga ggggttgtac   1320
aatgagctgc agaaggacaa gatggctgaa gcctatagcg agatcggaat gaaaggcgaa   1380
agacgcagag gcaaggggca tgacggtctg taccagggtc tctctacagc caccaaggac   1440
acttatgatg cgttgcatat gcaagccttg ccaccccgct aatga                   1485
```

<210> SEQ ID NO 11
<211> LENGTH: 184
<212> TYPE: PRT
<213> ORGANISM: Homo sapiens

<400> SEQUENCE: 11

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr

```
                20                  25                  30
Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
 50                  55                  60

Ile Ile Ser Leu Ala Val Phe Val Leu Met Phe Leu Leu Arg Lys Ile
 65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
            115                 120                 125

Glu Asp Cys Ile Lys Ser Lys Pro Lys Val Asp Ser Asp His Cys Phe
            130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 12
<211> LENGTH: 5
<212> TYPE: PRT
<213> ORGANISM: Artificial Sequence
<220> FEATURE:
<223> OTHER INFORMATION: Flexible peptide linker

<400> SEQUENCE: 12

Asp Gly Gly Gly Ser
1               5

<210> SEQ ID NO 13
<211> LENGTH: 5
<212> TYPE: PRT
<213> ORGANISM: Artificial Sequence
<220> FEATURE:
<223> OTHER INFORMATION: Flexible peptide linker

<400> SEQUENCE: 13

Thr Gly Glu Lys Pro
1               5

<210> SEQ ID NO 14
<211> LENGTH: 4
<212> TYPE: PRT
<213> ORGANISM: Artificial Sequence
<220> FEATURE:
<223> OTHER INFORMATION: Flexible peptide linker

<400> SEQUENCE: 14

Gly Gly Arg Arg
1

<210> SEQ ID NO 15
<211> LENGTH: 5
<212> TYPE: PRT
<213> ORGANISM: Artificial Sequence
<220> FEATURE:
<223> OTHER INFORMATION: Flexible peptide linker
```

```
<400> SEQUENCE: 15

Gly Gly Gly Gly Ser
1               5

<210> SEQ ID NO 16
<211> LENGTH: 14
<212> TYPE: PRT
<213> ORGANISM: Artificial Sequence
<220> FEATURE:
<223> OTHER INFORMATION: Flexible peptide linker

<400> SEQUENCE: 16

Glu Gly Lys Ser Ser Gly Ser Gly Ser Glu Ser Lys Val Asp
1               5                   10

<210> SEQ ID NO 17
<211> LENGTH: 18
<212> TYPE: PRT
<213> ORGANISM: Artificial Sequence
<220> FEATURE:
<223> OTHER INFORMATION: Flexible peptide linker

<400> SEQUENCE: 17

Lys Glu Ser Gly Ser Val Ser Ser Glu Gln Leu Ala Gln Phe Arg Ser
1               5                   10                  15

Leu Asp

<210> SEQ ID NO 18
<211> LENGTH: 8
<212> TYPE: PRT
<213> ORGANISM: Artificial Sequence
<220> FEATURE:
<223> OTHER INFORMATION: Flexible peptide linker

<400> SEQUENCE: 18

Gly Gly Arg Arg Gly Gly Gly Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Flexible peptide linker

<400> SEQUENCE: 19

Leu Arg Gln Arg Asp Gly Glu Arg Pro
1               5

<210> SEQ ID NO 20
<211> LENGTH: 12
<212> TYPE: PRT
<213> ORGANISM: Artificial Sequence
<220> FEATURE:
<223> OTHER INFORMATION: Flexible peptide linker

<400> SEQUENCE: 20

Leu Arg Gln Lys Asp Gly Gly Gly Ser Glu Arg Pro
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Flexible peptide linker
```

```
<400> SEQUENCE: 21

Leu Arg Gln Lys Asp Gly Gly Gly Ser Gly Gly Gly Ser Glu Arg Pro
1               5                   10                  15

<210> SEQ ID NO 22
<211> LENGTH: 18
<212> TYPE: PRT
<213> ORGANISM: Artificial Sequence
<220> FEATURE:
<223> OTHER INFORMATION: Flexible peptide linker

<400> SEQUENCE: 22

Gly Ser Thr Ser Gly Ser Gly Lys Pro Gly Ser Gly Glu Gly Ser Thr
1               5                   10                  15

Lys Gly

<210> SEQ ID NO 23
<211> LENGTH: 7
<212> TYPE: PRT
<213> ORGANISM: Artificial Sequence
<220> FEATURE:
<223> OTHER INFORMATION: protease cleavage site
<220> FEATURE:
<221> NAME/KEY: MISC_FEATURE
<222> LOCATION: (2)..(3)
<223> OTHER INFORMATION: Xaa = Any amino acid
<220> FEATURE:
<221> NAME/KEY: MISC_FEATURE
<222> LOCATION: (5)..(5)
<223> OTHER INFORMATION: Xaa = Any amino acid
<220> FEATURE:
<221> NAME/KEY: MISC_FEATURE
<222> LOCATION: (7)..(7)
<223> OTHER INFORMATION: Xaa  is Gly or Ser

<400> SEQUENCE: 23

Glu Xaa Xaa Tyr Xaa Gln Xaa
1               5

<210> SEQ ID NO 24
<211> LENGTH: 7
<212> TYPE: PRT
<213> ORGANISM: Artificial Sequence
<220> FEATURE:
<223> OTHER INFORMATION: protease cleavage site

<400> SEQUENCE: 24

Glu Asn Leu Tyr Phe Gln Gly
1               5

<210> SEQ ID NO 25
<211> LENGTH: 7
<212> TYPE: PRT
<213> ORGANISM: Artificial Sequence
<220> FEATURE:
<223> OTHER INFORMATION: protease cleavage site

<400> SEQUENCE: 25

Glu Asn Leu Tyr Phe Gln Ser
1               5

<210> SEQ ID NO 26
<211> LENGTH: 19
<212> TYPE: PRT
<213> ORGANISM: Artificial Sequence
<220> FEATURE:
<223> OTHER INFORMATION: protease cleavage site
```

<400> SEQUENCE: 26

Leu Leu Asn Phe Asp Leu Leu Lys Leu Ala Gly Asp Val Glu Ser Asn
1               5                   10                  15

Pro Gly Pro

<210> SEQ ID NO 27
<211> LENGTH: 19
<212> TYPE: PRT
<213> ORGANISM: Artificial Sequence
<220> FEATURE:
<223> OTHER INFORMATION: protease cleavage site

<400> SEQUENCE: 27

Thr Leu Asn Phe Asp Leu Leu Lys Leu Ala Gly Asp Val Glu Ser Asn
1               5                   10                  15

Pro Gly Pro

<210> SEQ ID NO 28
<211> LENGTH: 14
<212> TYPE: PRT
<213> ORGANISM: Artificial Sequence
<220> FEATURE:
<223> OTHER INFORMATION: protease cleavage site

<400> SEQUENCE: 28

Leu Leu Lys Leu Ala Gly Asp Val Glu Ser Asn Pro Gly Pro
1               5                   10

<210> SEQ ID NO 29
<211> LENGTH: 17
<212> TYPE: PRT
<213> ORGANISM: Artificial Sequence
<220> FEATURE:
<223> OTHER INFORMATION: protease cleavage site

<400> SEQUENCE: 29

Asn Phe Asp Leu Leu Lys Leu Ala Gly Asp Val Glu Ser Asn Pro Gly
1               5                   10                  15

Pro

<210> SEQ ID NO 30
<211> LENGTH: 20
<212> TYPE: PRT
<213> ORGANISM: Artificial Sequence
<220> FEATURE:
<223> OTHER INFORMATION: protease cleavage site

<400> SEQUENCE: 30

Gln Leu Leu Asn Phe Asp Leu Leu Lys Leu Ala Gly Asp Val Glu Ser
1               5                   10                  15

Asn Pro Gly Pro
            20

<210> SEQ ID NO 31
<211> LENGTH: 24
<212> TYPE: PRT
<213> ORGANISM: Artificial Sequence
<220> FEATURE:
<223> OTHER INFORMATION: protease cleavage site

<400> SEQUENCE: 31

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 32
<211> LENGTH: 40
<212> TYPE: PRT
<213> ORGANISM: Artificial Sequence
<220> FEATURE:
<223> OTHER INFORMATION: protease cleavage site

<400> SEQUENCE: 32

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
            35                  40

<210> SEQ ID NO 33
<211> LENGTH: 18
<212> TYPE: PRT
<213> ORGANISM: Artificial Sequence
<220> FEATURE:
<223> OTHER INFORMATION: protease cleavage site

<400> SEQUENCE: 33

Leu Asn Phe Asp Leu Leu Lys Leu Ala Gly Asp Val Glu Ser Asn Pro
1               5                   10                  15

Gly Pro

<210> SEQ ID NO 34
<211> LENGTH: 40
<212> TYPE: PRT
<213> ORGANISM: Artificial Sequence
<220> FEATURE:
<223> OTHER INFORMATION: protease cleavage site

<400> SEQUENCE: 34

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
            35                  40

<210> SEQ ID NO 35
<211> LENGTH: 33
<212> TYPE: PRT
<213> ORGANISM: Artificial Sequence
<220> FEATURE:
<223> OTHER INFORMATION: protease cleavage site

<400> SEQUENCE: 35

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 36
<211> LENGTH: 7350
<212> TYPE: DNA

<213> ORGANISM: Artificial Sequence
<220> FEATURE:
<223> OTHER INFORMATION: anti-BCMA02 CAR vector

<400> SEQUENCE: 36

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatcatat gccagcctat ggtgacattg attattgact agttattaat agtaatcaat     240
tacggggtca ttagttcata gcccatatat ggagttccgc gttacataac ttacggtaaa     300
tggcccgcct ggctgaccgc ccaacgaccc ccgcccattg acgtcaataa tgacgtatgt     360
tcccatagta acgccaatag ggactttcca ttgacgtcaa tgggtggagt atttacggta     420
aactgcccac ttggcagtac atcaagtgta tcatatgcca gtacgcccc ctattgacgt      480
caatgacggt aaatggcccg cctggcatta tgcccagtac atgaccttat gggactttcc     540
tacttggcag tacatctacg tattagtcat cgctattacc atggtgatgc ggttttggca     600
gtacatcaat gggcgtggat agcggtttga ctcacgggga tttccaagtc tccaccccat     660
tgacgtcaat gggagtttgt tttggcacca aaatcaacgg gactttccaa aatgtcgtaa     720
caactccgcc ccattgacgc aaatgggcgg taggcgtgta cggtgggagg tctatataag     780
cagagctcgt ttagtgaacc gggtctctct ggttagacca gatctgagcc tgggagctct     840
ctggctaact agggaaccca ctgcttaagc ctcaataaag cttgccttga gtgctcaaag     900
tagtgtgtgc ccgtctgttg tgtgactctg gtaactagag atccctcaga cccttttagt     960
cagtgtggaa aatctctagc agtggcgccc gaacagggac ttgaaagcga aagtaaagcc    1020
agaggagatc tctcgacgca ggactcggct tgctgaagcg cgcacggcaa gaggcgaggg    1080
gcggcgactg gtgagtacgc caaaaatttt gactagcgga ggctagaagg agagagtagg    1140
gtgcgagagc gtcggtatta agcgggggag aattagataa atgggaaaaa attcggttaa    1200
ggccaggggg aaagaaacaa tataaactaa aacatatagt tagggcaagc agggagctag    1260
aacgattcgc agttaatcct ggccttttag acatcagaa ggctgtaga caaatactgg       1320
gacagctaca accatcccctt cagacaggat cagaagaact tagatcatta taatacaa      1380
tagcagtcct ctattgtgtg catcaaagga tagatgtaaa agacaccaag gaagccttag    1440
ataagataga ggaagagcaa aacaaaagta agaaaaaggc acagcaagca gcagctgaca    1500
caggaaacaa cagccaggtc agccaaaatt accctatagt gcagaacctc aggggcaaa     1560
tggtacatca ggccatatca cctagaactt taaattaaga cagcagtaca aatggcagta    1620
ttcatccaca atttttaaaag aaaagggggg attgggggt acagtgcagg ggaaagaata    1680
gtagacataa tagcaacaga catacaaact aaagaattac aaaaacaaat tacaaaaatt    1740
caaaattttc gggtttatta cagggacagc agagatccag tttggaaagg accagcaaag    1800
ctcctctgga aaggtgaagg ggcagtagta atacaagata atagtgacat aaaagtagtg    1860
ccaagaagaa aagcaaagat catcagggat tatggaaaac agatggcagg tgatgattgt    1920
gtggcaagta gacaggatga ggattaacac atggaaagat tagtaaaac accatagctc      1980
tagagcgatc ccgatcttca gacctggagg aggagatatg agggacaatt ggagaagtga    2040
attatataaa tataaagtag taaaattga accattagga gtagcaccca ccaaggcaaa     2100
gagaagagtg gtgcagagag aaaaagagc agtgggaata ggagctttgt tccttgggtt    2160
cttgggagca gcaggaagca ctatgggcgc agcgtcaatg acgctgacgg tacaggccag    2220
```

```
acaattattg tctggtatag tgcagcagca gaacaatttg ctgagggcta ttgaggcgca   2280
acagcatctg ttgcaactca cagtctgggg catcaagcag ctccaggcaa gaatcctggc   2340
tgtggaaaga tacctaaagg atcaacagct cctggggatt tggggttgct ctggaaaact   2400
catttgcacc actgctgtgc cttggaatgc tagttggagt aataaatctc tggaacagat   2460
ttggaatcac acgacctgga tggagtggga cagagaaatt aacaattaca caagcttggt   2520
aggtttaaga atagttttg ctgtactttc tatagtgaat agagttaggc agggatattc    2580
accattatcg tttcagaccc acctcccaac cccaggggga cccgacaggc ccgaaggaat   2640
agaagaagaa ggtggagaga gagacagaga cagatccatt cgattagtga acggatccat   2700
ctcgacggaa tgaaagaccc cacctgtagg tttggcaagc taggatcaag gttaggaaca   2760
gagagacagc agaatatggg ccaaacagga tatctgtggt aagcagttcc tgccccggct   2820
cagggccaag aacagttgga acagcagaat atgggccaaa caggatatct gtggtaagca   2880
gttcctgccc cggctcaggg ccaagaacag atggtcccca gatgcggtcc cgccctcagc   2940
agtttctaga gaaccatcag atgtttccag ggtgccccaa ggacctgaaa tgaccctgtg   3000
ccttatttga actaaccaat cagttcgctt ctcgcttctg ttcgcgcgct tctgctcccc   3060
gagctcaata aaagagccca aaccccctca ctcggcgcga ttcacctgac gcgtctacgc   3120
caccatggca ctccccgtca ccgcccttct cttgcccctc gcctgctgc tgcatgctgc    3180 caggcccgac attgtgctca ctcagtcacc tcccagcctg gccatgagcc tgggaaaaag   3240
ggccaccatc tcctgtagag ccagtgagtc cgtcacaatc ttggggagcc atcttattca   3300
ctggtatcag cagaagcccg gcagcctcc aaccttctt attcagctcg cgtcaaacgt      3360
ccagacgggt gtacctgcca gattttctgg tagcgggtcc cgcactgatt ttacactgac   3420
catagatcca gtggaagaag acgatgtggc cgtgtattat tgtctgcaga gcagaacgat   3480
tcctcgcaca tttggtgggg gtactaagct ggagattaag gaagcacgt ccggctcagg     3540 gaagccgggc tccggcgagg gaagcacgaa ggggcaaatt cagctggtcc agagcggacc   3600
tgagctgaaa aaacccggcg agactgttaa gatcagttgt aaagcatctg gctatacctt   3660
caccgactac agcataaatt gggtgaaacg ggcccctgga aagggcctca atggatggg    3720 ttggatcaat accgaaacta gggagcctgc ttatgcatat gacttccgcg ggagattcgc   3780
cttttcactc gagacatctg cctctactgc ttacctccaa ataaacaacc tcaagtatga   3840
agatacagcc acttactttt gcgccctcga ctatagttac gccatggact actggggaca   3900
gggaacctcc gttaccgtca gttccgcggc cgcaaccaca acacctgctc caaggccccc   3960
cacacccgct ccaactatag ccagccaacc attgagcctc agacctgaag cttgcaggcc   4020
cgcagcagga ggcgccgtcc atacgcgagg cctggacttc gcgtgtgata tttatattttg   4080 ggccccttg gccggaacat gtggggtgtt gcttctctcc cttgtgatca ctctgtattg     4140 taagcgcgg agaagaagc tcctgtacat cttcaagcag cctttatgc gacctgtgca       4200 aaccactcag gaagaagatg ggtgttcatg ccgcttcccc gaggaggaag aaggagggtg   4260
tgaactgagg gtgaaatttt ctagaagcgc cgatgctccc gcatatcagc agggtcagaa    4320
tcagctctac aatgaattga atctcggcag gcgagaagag tacgatgttc tggacaagag   4380
acggggcagg gatcccgaga tggggggaaa gccccggaga aaaatcctc aggagggtt      4440 gtacaatgag ctgcagaagg acaagatggc tgaagcctat agcgagatcg gaatgaaagg   4500
cgaaagacgc agaggcaagg ggcatgacgg tctgtaccag ggtctctcta cagccaccaa   4560
```

```
ggacacttat gatgcgttgc atatgcaagc cttgccaccc cgctaatgac aggtaccttt    4620
aagaccaatg acttacaagg cagctgtaga tcttagccac ttttaaaag aaaagggggg     4680 actggaaggg ctaattcact cccaaagaag acaagatctg cttttgcct gtactgggtc     4740 tctctggtta gaccagatct gagcctggga gctctctggc taactaggga acccactgct    4800
taagcctcaa taaagcttgc cttgagtgct tcaatgtgtg tgttggtttt ttgtgtgtcg    4860
aaattctagc gattctagct tggcgtaatc atggtcatag ctgtttcctg tgtgaaattg    4920
ttatccgctc acaattccac acaacatacg agccggaagc ataaagtgta aagcctgggg    4980
tgcctaatga gtgagctaac tcacattaat tgcgttgcgc tcactgcccg ctttccagtc    5040
gggaaacctg tcgtgccagc tgcattaatg aatcggccaa cgcgcgggga gaggcggttt    5100
gcgtattggg cgctcttccg cttcctcgct cactgactcg ctgcgctcgg tcgttcggct    5160
gcggcgagcg gtatcagctc actcaaaggc ggtaatacgg ttatccacag aatcagggga    5220
taacgcagga aagaacatgt gagcaaaagg ccagcaaaag gccaggaacc gtaaaaaggc    5280
cgcgttgctg gcgtttttcc ataggctccg ccccctgac gagcatcaca aaaatcgacg     5340
ctcaagtcag aggtggcgaa acccgacagg actataaaga taccaggcgt ttccccctgg    5400
aagctccctc gtgcgctctc ctgttccgac cctgccgctt accggatacc tgtccgcctt    5460
tctcccttcg ggaagcgtgg cgctttctca tagctcacgc tgtaggtatc tcagttcggt    5520
gtaggtcgtt cgctccaagc tgggctgtgt gcacgaaccc cccgttcagc ccgaccgctg    5580
cgccttatcc ggtaactatc gtcttgagtc aacccggta agacacgact tatcgccact     5640
ggcagcagcc actggtaaca ggattagcag agcgaggtat gtaggcggtg ctacagagtt    5700
cttgaagtgg tggcctaact acggctacac tagaagaaca gtatttggta tctgcgctct    5760
gctgaagcca gttaccttcg gaaaaagagt tggtagctct tgatccggca acaaaccac     5820 cgctggtagc ggtggttttt ttgtttgcaa gcagcagatt acgcgcagaa aaaaggatc     5880 tcaagaagat cctttgatct tttctacggg gtctgacgct cagtggaacg aaaactcacg    5940
ttaagggatt ttggtcatga gattatcaaa aaggatcttc acctagatcc ttttaaatta    6000
aaaatgaagt tttaaatcaa tctaaagtat atatgagtaa acttggtctg acagttacca    6060
atgcttaatc agtgaggcac ctatctcagc gatctgtcta tttcgttcat ccatagttgc    6120
ctgactcccc gtcgtgtaga taactacgat acgggagggc ttaccatctg gccccagtgc    6180
tgcaatgata ccgcgagacc cacgctcacc ggctccagat ttatcagcaa taaaccagcc    6240
agccggaagg gccgagcgca gaagtggtcc tgcaacttta tccgcctcca tccagtctat    6300
taattgttgc cgggaagcta gagtaagtag ttcgccagtt aatagtttgc gcaacgttgt    6360
tgccattgct acaggcatcg tggtgtcacg ctcgtcgttt ggtatggctt cattcagctc    6420
cggttcccaa cgatcaaggc gagttacatg atccccatg ttgtgcaaaa aagcggttag     6480
ctccttcggt cctccgatcg ttgtcagaag taagttggcc gcagtgttat cactcatggt    6540
tatggcagca ctgcataatt ctcttactgt catgccatcc gtaagatgct tttctgtgac    6600
tggtgagtac tcaaccaagt cattctgaga atagtgtatg cggcgaccga gttgctcttg    6660
cccggcgtca atacgggata ataccgcgcc acatagcaga actttaaaag tgctcatcat    6720
tggaaaacgt tcttcggggc gaaaactctc aaggatctta ccgctgttga tccagttc     6780 gatgtaaccc actcgtgcac ccaactgatc ttcagcatct tttactttca ccagcgtttc    6840
tgggtgagca aaaacaggaa ggcaaaatgc cgcaaaaaag gaataagggg cgacacggaa    6900
atgttgaata ctcatactct tccttttttca atattattga agcatttatc agggttattg    6960
```

```
tctcatgagc ggatacatat ttgaatgtat ttagaaaaat aaacaaatag gggttccgcg    7020
cacatttccc cgaaaagtgc cacctgggac tagcttttttg caaaagccta ggcctccaaa    7080
aaagcctcct cactacttct ggaatagctc agaggccgag gcggcctcgg cctctgcata    7140
aataaaaaaa attagtcagc catggggcgg agaatgggcg gaactgggcg gagttagggg    7200
cgggatgggc ggagttaggg gcgggactat ggttgctgac taattgagat gagcttgcat    7260
gccgacattg attattgact agtccctaag aaaccattct tatcatgaca ttaacctata    7320
aaaataggcg tatcacgagg ccctttcgtc                                    7350
```